US012760254B2

United States Patent
(12) United States Patent
Fang et al.

(10) Patent No.: US 12,760,254 B2
(45) Date of Patent: Oct. 13, 2026

(54) DEVICES AND METHODS FOR GENERATION AND CULTURE OF 3D CELL AGGREGATES

(71) Applicant: Corning Incorporated, Corning, NY (US)

(72) Inventors: Ye Fang, Painted Post, NY (US); Ann MeeJin Ferrie, Painted Post, NY (US); Vasiliy Nikolaevich Goral, Painted Post, NY (US); Gregory Roger Martin, Acton, ME (US); Kaitlyn Mary Matias, Corning, NY (US); Michael Kurt Schaefer, Gorham, NC (US); Allison Jean Tanner, Portsmouth, NH (US)

(73) Assignee: CORNING INCORPORATED, Corning, NY (US)

(*) Notice: Subject to any disclaimer, the term of this patent is extended or adjusted under 35 U.S.C. 154(b) by 1338 days.

(21) Appl. No.: 16/447,453

(22) Filed: Jun. 20, 2019

(65) Prior Publication Data

US 2019/0322969 A1 Oct. 24, 2019

Related U.S. Application Data

(63) Continuation of application No. 15/492,690, filed on Apr. 20, 2017, now abandoned, which is a continuation of application No. PCT/US2015/058048, filed on Oct. 29, 2015.

(60) Provisional application No. 62/072,015, filed on Oct. 29, 2014.

(51) Int. Cl.

*C12M 1/00* (2006.01)
*C12M 1/04* (2006.01)
*C12M 1/26* (2006.01)
*C12M 1/32* (2006.01)
(Continued)

(52) U.S. Cl.

CPC ............ *C12M 23/12* (2013.01); *C12M 1/268* (2013.01); *C12M 3/065* (2013.01); *C12M 23/02* (2013.01); *C12M 23/24* (2013.01); *C12M 23/00* (2013.01)

(58) Field of Classification Search

CPC .............................. C12M 23/12; C12M 23/24
See application file for complete search history.

(56) References Cited

U.S. PATENT DOCUMENTS

| | | | |
|---|---|---|---|
| 2,947,116 | A | 8/1960 | Earle et al. |
| 3,630,849 | A | 12/1971 | Land et al. |
| 4,670,396 | A | 6/1987 | Bear et al. |

(Continued)

FOREIGN PATENT DOCUMENTS

| | | | |
|---|---|---|---|
| AU | 2004256209 | A1 | 1/2005 |
| CA | 2558946 | A1 | 1/2005 |

(Continued)

OTHER PUBLICATIONS

Tung et al. "High-throughput 3D spheroid culture and drug testing using 384 hanging drop array." Analyst, 2011, 136, 473-478.

(Continued)

*Primary Examiner* — Nathan A Bowers
(74) *Attorney, Agent, or Firm* — Chandra J. Duncan

(57) ABSTRACT

The present disclosure relates to apparatuses, systems and methods for culturing cells. In particular, devices and methods are provided for generation and culture of 3d cell aggregates.

19 Claims, 21 Drawing Sheets

(51) Int. Cl.
*C12M 3/00* (2006.01)
*C12M 3/06* (2006.01)

(56) References Cited

U.S. PATENT DOCUMENTS

| | | | |
|---|---|---|---|
| 4,927,764 | A | 5/1990 | Lyman et al. |
| 5,047,347 | A | 9/1991 | Cline |
| 5,151,366 | A | 9/1992 | Serkes et al. |
| 5,171,994 | A | 12/1992 | Bahraman |
| 5,171,995 | A | 12/1992 | Gast et al. |
| 5,240,854 | A | 8/1993 | Berry et al. |
| 5,272,084 | A | 12/1993 | O'Connell et al. |
| 5,374,557 | A | 12/1994 | Verma |
| 5,487,872 | A | 1/1996 | Hafeman et al. |
| 5,554,536 | A | 9/1996 | Rising |
| 5,665,562 | A | 9/1997 | Cook |
| 5,693,537 | A | 12/1997 | Wilson et al. |
| 5,707,869 | A | 1/1998 | Wolf et al. |
| 5,710,043 | A | 1/1998 | Pay |
| 5,759,494 | A | 6/1998 | Szlosek |
| 5,772,905 | A | 6/1998 | Chou |
| 5,783,440 | A | 7/1998 | Stevens |
| 5,792,653 | A | 8/1998 | Weibezahn et al. |
| 5,858,309 | A | 1/1999 | Mathus et al. |
| 5,972,694 | A | 10/1999 | Mathus |
| 6,030,829 | A | 2/2000 | Dannoux et al. |
| 6,039,972 | A | 3/2000 | Barlow et al. |
| 6,306,646 | B1 | 10/2001 | Saad et al. |
| 6,348,999 | B1 | 2/2002 | Summersgill et al. |
| 6,514,464 | B1 | 2/2003 | Knebel |
| 6,521,451 | B2 | 2/2003 | Potter |
| 6,767,607 | B2 | 7/2004 | Tanner et al. |
| 6,811,752 | B2 | 11/2004 | Barbera-Guillem |
| 6,908,767 | B2 | 6/2005 | Bader |
| 7,470,424 | B2 | 12/2008 | Kataoka et al. |
| 7,547,547 | B2 | 6/2009 | Dang et al. |
| 7,674,346 | B2 | 3/2010 | Clements et al. |
| 7,687,262 | B2 | 3/2010 | Cattadoris |
| 7,691,369 | B2 | 4/2010 | Kataoka et al. |
| 7,727,759 | B2 | 6/2010 | Ozawa et al. |
| 7,745,209 | B2 | 6/2010 | Martin et al. |
| 7,745,210 | B2 | 6/2010 | Martin |
| 7,897,379 | B2 | 3/2011 | Kenney et al. |
| 7,919,319 | B2 | 4/2011 | Jervis et al. |
| 8,053,230 | B2 | 11/2011 | Whittlinger |
| 8,143,053 | B2 | 3/2012 | Yerbic |
| 8,148,152 | B2 | 4/2012 | Kolossov et al. |
| 8,158,426 | B2 | 4/2012 | Wilson et al. |
| 8,158,427 | B2 | 4/2012 | Wilson et al. |
| 8,163,537 | B2 | 4/2012 | Martin et al. |
| 8,168,432 | B2 | 5/2012 | Wilson et al. |
| 8,178,345 | B2 | 5/2012 | Bennett et al. |
| 8,273,572 | B2 | 9/2012 | Martin et al. |
| 8,318,479 | B2 | 11/2012 | Domansky et al. |
| 8,415,144 | B2 | 4/2013 | Wilson et al. |
| 8,470,589 | B2 | 6/2013 | Martin et al. |
| D685,497 | S | 7/2013 | Kenney et al. |
| 8,486,692 | B2 | 7/2013 | Simon |
| 8,597,597 | B2 | 12/2013 | Deutsch et al. |
| 8,617,879 | B2 | 12/2013 | Yu et al. |
| 8,697,443 | B2 | 4/2014 | Wilson et al. |
| 8,759,017 | B2 | 6/2014 | Owen et al. |
| 8,778,669 | B2 | 7/2014 | Lacey et al. |
| 8,846,399 | B2 | 9/2014 | Martin et al. |
| 8,906,685 | B2 | 12/2014 | Takayama et al. |
| 8,932,544 | B2 | 1/2015 | Mueller et al. |
| 9,039,883 | B2 | 5/2015 | Guerrieri et al. |
| 9,040,293 | B2 | 5/2015 | Gulzow et al. |
| 9,045,721 | B2 | 6/2015 | Martin et al. |
| 9,068,281 | B2 | 6/2015 | Wu et al. |
| 9,126,199 | B2 | 9/2015 | Moritz et al. |
| 9,169,460 | B2 | 10/2015 | Cecchi |
| D748,812 | S | 2/2016 | Kenney et al. |
| 9,260,684 | B1 | 2/2016 | Egeler et al. |
| 9,260,695 | B2 | 2/2016 | Crowley et al. |
| 9,493,733 | B2 | 11/2016 | Giles |
| 9,494,577 | B2 | 11/2016 | McGarr et al. |
| 9,573,128 | B1 | 2/2017 | Mcclelland |
| 9,587,213 | B2 | 3/2017 | Morgan et al. |
| 9,732,317 | B2 | 8/2017 | Wilson |
| 9,790,465 | B2 | 10/2017 | Bennett et al. |
| 9,845,451 | B2 | 12/2017 | Martin et al. |
| 9,862,918 | B2 | 1/2018 | Ito |
| 10,254,274 | B2 | 4/2019 | Miklas et al. |
| 2002/0022219 | A1 | 2/2002 | Clements et al. |
| 2003/0031829 | A1 | 2/2003 | Tanner et al. |
| 2003/0104494 | A1 | 6/2003 | Ravkin et al. |
| 2003/0183958 | A1 | 10/2003 | Goff et al. |
| 2003/0186217 | A1 | 10/2003 | Bader |
| 2003/0215941 | A1 | 11/2003 | Campbell et al. |
| 2004/0091397 | A1 | 5/2004 | Picard |
| 2004/0101955 | A1 | 5/2004 | Whitley |
| 2004/0125266 | A1 | 7/2004 | Miyauchi et al. |
| 2004/0216835 | A1 | 11/2004 | Tanner et al. |
| 2004/0259242 | A1 | 12/2004 | Malinge et al. |
| 2005/0032208 | A1 | 2/2005 | Oh et al. |
| 2005/0047971 | A1 | 3/2005 | Clements et al. |
| 2005/0112030 | A1 | 5/2005 | Gaus |
| 2005/0116717 | A1 | 6/2005 | Dransfield et al. |
| 2005/0147959 | A1 | 7/2005 | Frondoza et al. |
| 2006/0110822 | A1 | 5/2006 | Robbins et al. |
| 2006/0234370 | A1 | 10/2006 | Korpinen et al. |
| 2006/0252044 | A1 | 11/2006 | Okumura et al. |
| 2006/0292654 | A1 | 12/2006 | Reardon |
| 2007/0178441 | A1 | 8/2007 | Li |
| 2008/0118974 | A1 | 5/2008 | Martin et al. |
| 2008/0206857 | A1 | 8/2008 | Kenney et al. |
| 2008/0268515 | A1* | 10/2008 | Cullimore .............. C12M 35/02 435/174 |
| 2008/0300278 | A1 | 12/2008 | Torrens Jover et al. |
| 2009/0017540 | A1* | 1/2009 | Nishio .................. C12M 25/06 435/395 |
| 2009/0018033 | A1 | 1/2009 | Morgan et al. |
| 2009/0029462 | A1 | 1/2009 | Beardsley et al. |
| 2009/0170190 | A1 | 7/2009 | Nishi et al. |
| 2009/0191620 | A1 | 7/2009 | Martin et al. |
| 2009/0288963 | A1 | 11/2009 | Guerrieri et al. |
| 2009/0298116 | A1* | 12/2009 | Fang .................... B01L 3/5085 430/320 |
| 2009/0298164 | A1 | 12/2009 | Cattadoris et al. |
| 2009/0298166 | A1 | 12/2009 | Fang et al. |
| 2010/0068793 | A1 | 3/2010 | Ungrin et al. |
| 2010/0093075 | A1 | 4/2010 | Muller |
| 2010/0112684 | A1 | 5/2010 | Lee et al. |
| 2010/0119418 | A1 | 5/2010 | Clements et al. |
| 2010/0170790 | A1 | 7/2010 | Takahashi et al. |
| 2010/0190197 | A1 | 7/2010 | Martin et al. |
| 2010/0197013 | A1 | 8/2010 | Kamp et al. |
| 2010/0247386 | A1 | 9/2010 | Deutsch et al. |
| 2010/0273258 | A1 | 10/2010 | Lannutti et al. |
| 2010/0297600 | A1 | 11/2010 | Cecchi |
| 2010/0331216 | A1* | 12/2010 | Sokabe ................ C12N 5/0062 506/26 |
| 2011/0086375 | A1 | 4/2011 | Ungrin et al. |
| 2011/0097790 | A1 | 4/2011 | Yerbic |
| 2011/0129923 | A1 | 6/2011 | Wilson et al. |
| 2012/0064627 | A1 | 3/2012 | Khine et al. |
| 2012/0129208 | A1 | 5/2012 | Khine et al. |
| 2012/0129257 | A1 | 5/2012 | Yu et al. |
| 2012/0219572 | A1 | 8/2012 | Prockop et al. |
| 2013/0122539 | A1 | 5/2013 | Li et al. |
| 2013/0122580 | A1 | 5/2013 | Tsukada et al. |
| 2013/0143254 | A1 | 6/2013 | Thomas et al. |
| 2013/0164848 | A1 | 6/2013 | Munaka et al. |
| 2013/0203159 | A1 | 8/2013 | Itoh et al. |
| 2013/0344598 | A1 | 12/2013 | Nistor |
| 2014/0004557 | A1* | 1/2014 | Ma ........................ C12M 23/12 435/283.1 |
| 2014/0099717 | A1 | 4/2014 | Fraker et al. |
| 2014/0106394 | A1 | 4/2014 | Ko et al. |
| 2014/0106452 | A1 | 4/2014 | Vukasinovic |
| 2014/0120573 | A1 | 5/2014 | Tavana et al. |
| 2014/0221225 | A1 | 8/2014 | Danen et al. |
| 2014/0227784 | A1 | 8/2014 | Ejiri et al. |

(56) References Cited

U.S. PATENT DOCUMENTS

| | | | | |
|---|---|---|---|---|
| 2014/0315296 | A1 | 10/2014 | Wilson | |
| 2014/0322806 | A1 | 10/2014 | Bennett et al. | |
| 2015/0004686 | A1 | 1/2015 | Goral et al. | |
| 2015/0050722 | A1 * | 2/2015 | Simmons | C12M 23/12 435/305.2 |
| 2015/0064738 | A1 | 3/2015 | Tsukada et al. | |
| 2015/0072405 | A1 | 3/2015 | Ito | |
| 2015/0184119 | A1 | 7/2015 | Tsukada et al. | |
| 2015/0247112 | A1 | 9/2015 | Orr et al. | |
| 2016/0003796 | A1 | 1/2016 | Kranbuehl | |
| 2016/0017267 | A1 | 1/2016 | Hansen et al. | |
| 2016/0137962 | A1 | 5/2016 | Ejiri et al. | |
| 2016/0194588 | A1 | 7/2016 | Guenat et al. | |
| 2016/0216250 | A1 | 7/2016 | Ritter et al. | |
| 2017/0073625 | A1 | 3/2017 | Kasuto et al. | |
| 2017/0226455 | A1 | 8/2017 | Fang et al. | |
| 2017/0283757 | A1 | 10/2017 | Carter et al. | |
| 2017/0306281 | A1 | 10/2017 | Martin et al. | |
| 2017/0342363 | A1 | 11/2017 | Fang et al. | |
| 2018/0201888 | A1 | 7/2018 | Miwa et al. | |

FOREIGN PATENT DOCUMENTS

| | | | |
|---|---|---|---|
| CA | 2679011 | A1 | 9/2008 |
| CA | 2848875 | A1 | 3/2013 |
| CN | 2186755 | Y | 1/1995 |
| CN | 1234112 | A | 11/1999 |
| CN | 1875093 | A | 12/2006 |
| CN | 201626959 | U | 11/2010 |
| CN | 101978041 | A | 2/2011 |
| CN | 102105578 | A | 6/2011 |
| CN | 102257123 | A | 11/2011 |
| CN | 102449135 | A | 5/2012 |
| CN | 202450098 | U | 9/2012 |
| CN | 202849407 | U | 4/2013 |
| CN | 103080294 | A | 5/2013 |
| CN | 103119151 | A | 5/2013 |
| CN | 203513696 | U | 4/2014 |
| CN | 103814125 | A | 5/2014 |
| CN | 204608026 | U | 9/2015 |
| CN | 204702760 | U | 10/2015 |
| CN | 204714819 | U | 10/2015 |
| CN | 204752742 | U | 11/2015 |
| CN | 204803327 | U | 11/2015 |
| CN | 205170866 | U | 4/2016 |
| CN | 205669029 | U | 11/2016 |
| CN | 205839030 | U | 12/2016 |
| CN | 205990396 | U | 3/2017 |
| DE | 10019862 | A1 | 11/2001 |
| DE | 202006017853 | U1 | 2/2007 |
| DE | 102009005526 | A1 | 7/2010 |
| DE | 102014214077 | A1 | 1/2016 |
| DE | 102014017728 | A1 | 6/2016 |
| EP | 307048 | A2 | 3/1989 |
| EP | 0605527 | A1 | 7/1994 |
| EP | 0681846 | A2 | 11/1995 |
| EP | 0800571 | A2 | 10/1997 |
| EP | 834552 | A1 | 4/1998 |
| EP | 965633 | A1 | 12/1999 |
| EP | 1181349 | A1 | 2/2002 |
| EP | 1348533 | A2 | 10/2003 |
| EP | 1445022 | A2 | 8/2004 |
| EP | 1988152 | A1 | 11/2008 |
| EP | 2032262 | A2 | 3/2009 |
| EP | 2617807 | A1 | 7/2013 |
| EP | 2653531 | A1 | 10/2013 |
| EP | 2759592 | A1 | 7/2014 |
| EP | 2896684 | A1 | 7/2015 |
| EP | 3081627 | A1 | 10/2016 |
| EP | 3351615 | A1 | 7/2018 |
| EP | 3372666 | A1 | 9/2018 |
| GB | 2147100 | A | 5/1985 |
| JP | 06327462 | A | 11/1994 |
| JP | 09173049 | A | 7/1997 |
| JP | 10210866 | A | 8/1998 |
| JP | 10210966 | A | 8/1998 |
| JP | 2003135056 | A | 5/2003 |
| JP | 2003180335 | A | 7/2003 |
| JP | 2004129558 | A | 4/2004 |
| JP | 2006-191809 | A | 7/2006 |
| JP | 2007-510429 | A | 4/2007 |
| JP | 3139350 | U | 2/2008 |
| JP | 2009-017810 | A | 1/2009 |
| JP | 2009050194 | A | 3/2009 |
| JP | 2010088347 | A | 4/2010 |
| JP | 2010104327 | A | 5/2010 |
| JP | 2010-518879 | A | 6/2010 |
| JP | 2010158214 | A | 7/2010 |
| JP | 2011-509686 | A | 3/2011 |
| JP | 2011-521642 | A | 7/2011 |
| JP | 2011172533 | A | 9/2011 |
| JP | 2012249547 | A | 12/2012 |
| JP | 2013055911 | A | 3/2013 |
| JP | 2014132869 | A | 7/2014 |
| JP | 2015012827 | A | 1/2015 |
| JP | 2015073520 | A | 4/2015 |
| JP | 5845185 | B2 | 1/2016 |
| JP | 2016136921 | A | 8/2016 |
| JP | 2017-532970 | A | 11/2017 |
| KR | 1020140113139 | A | 9/2014 |
| KR | 10-2014-0125662 | A | 10/2014 |
| WO | 1992007063 | A2 | 4/1992 |
| WO | 93/07258 | A1 | 4/1993 |
| WO | 96/21851 | A2 | 7/1996 |
| WO | 9815355 | A2 | 4/1998 |
| WO | 1998031466 | A1 | 7/1998 |
| WO | 2001080997 | A1 | 11/2001 |
| WO | 2001092462 | A1 | 12/2001 |
| WO | 2004/044120 | A2 | 5/2004 |
| WO | 2004/094060 | A1 | 11/2004 |
| WO | 2005047464 | A2 | 5/2005 |
| WO | 2006043267 | A1 | 4/2006 |
| WO | 2007/015770 | A1 | 2/2007 |
| WO | 2007097120 | A1 | 8/2007 |
| WO | 2008/008149 | A2 | 1/2008 |
| WO | 2008/106771 | A1 | 9/2008 |
| WO | 2008118500 | A1 | 10/2008 |
| WO | 2008153783 | A1 | 12/2008 |
| WO | 2009094125 | A2 | 7/2009 |
| WO | 2009148509 | A1 | 12/2009 |
| WO | 2009148512 | A2 | 12/2009 |
| WO | 2010008566 | A2 | 1/2010 |
| WO | 2012036011 | A1 | 3/2012 |
| WO | 2012170232 | A1 | 12/2012 |
| WO | 2013042360 | A1 | 3/2013 |
| WO | 2013/108293 | A1 | 7/2013 |
| WO | 2013/116449 | A1 | 8/2013 |
| WO | 2014/042162 | A1 | 3/2014 |
| WO | 2014072432 | A1 | 5/2014 |
| WO | 2014/140181 | A1 | 9/2014 |
| WO | 2014156455 | A1 | 10/2014 |
| WO | 2014165273 | A1 | 10/2014 |
| WO | 2014171782 | A1 | 10/2014 |
| WO | 2014/179196 | A1 | 11/2014 |
| WO | 2014196204 | A1 | 12/2014 |
| WO | 2015033507 | A1 | 3/2015 |
| WO | 2015/061907 | A1 | 5/2015 |
| WO | 2016064757 | A1 | 4/2016 |
| WO | 2016069885 | A1 | 5/2016 |
| WO | 2016069892 | A1 | 5/2016 |
| WO | 2016069895 | A1 | 5/2016 |
| WO | 2016069917 | A1 | 5/2016 |
| WO | 2016069930 | A1 | 5/2016 |
| WO | 2017025584 | A1 | 2/2017 |
| WO | 2017/047735 | A1 | 3/2017 |
| WO | 2017/077163 | A1 | 5/2017 |
| WO | 2017142410 | A1 | 8/2017 |
| WO | 2018200893 | A1 | 11/2018 |
| WO | 2019014621 | A1 | 1/2019 |
| WO | 2019014627 | A1 | 1/2019 |
| WO | 2019014635 | A1 | 1/2019 |

(56) References Cited

FOREIGN PATENT DOCUMENTS

| | | | |
|---|---|---|---|
| WO | 2019014636 | A1 | 1/2019 |
| WO | 2019178039 | A1 | 9/2019 |

OTHER PUBLICATIONS

Uchida et al; "An Injectable Spheroid System With Genetic Modification for Cell Transplantation Therapy"; Biomaterials, 35 (2014) 2499-2506.
Vinci et al. Advances in establishment and analysis of three-dimensional tumor spheroid-based functional assays for target validation and drug evaluation, BMC Biology 2012, 10:29.
Weegman et al; "Nutrient Regulation By Continuous Feeding Removes Limitation On Cell Yeild in the Large-Scale Expansion of Mamalian Cell Spheroids"; PLOS ONE; Oct. 2013, vol. 8, Issue 10, 10 Pages.
Xu et al. "Characterization of some cytotoxic endpoints using rat liver and HepG2 spheroids as in vitro models and their application in hepatotoxicity studies. I. Glucose metabolism and enzyme release as cytotoxic markers." Toxicol Appl Pharmacol 2003; 189:10011.
Yamada et al. "Efficient induction of hepatocyte spheroids in a suspension culture using a water-soluble synthetic polymer as an artificial matrix." J Biochem 1998; 123: 101723.
SG11201703494P Search Report Dated Apr. 27, 18, Singapore Patent Office, 9 pgs.
Stemcell Technologies, Reproducible and Uniform Embryoid Bodies Using AggreWell Plates, StemCell Technologies, Version 3.0.0, Mar. 2011, Catalog #29146, pp1-28.
International Search Report and Written Opinion of the International Searching Authority; PCT/US15/58048; Mailed Feb. 11, 2016; 11 Pages; European Patent Office.
Labusca, "Scaffold free 3D culture of mesenchymal stem cells; implications for regenerative medicine", J Transplant Stem Cel Biol 2015 2(1): 8.
Lovett et al. "Vascularization Strategies for Tissue Engineering" Tissue Engineering Part B, 2009, vol. 15, No. 3, pp. 353-370.
Chinese Patent Application No. 201580071527.6; English Translation of the Office Action Mailed Oct. 9, 2019; China Patent Office; 11 Pgs.
Japanese Patent Application No. 2017523816; Machine Translation of the Office Action Mailed Oct. 2, 2019; Japan Patent Office; 6 Pgs.
Aline; "We Engineer Microfluidic Products" ; 7 Pages; (2020) https://alineinc.com/.
Bioivt Elevating Science ®; 6 Pages; (2020); http://www.hepregen.com/.
Cheng et al., "MICRORNA-34a Targets Forkhead Box J2 To Modulate Differentiation of Endothelial Progenitor Cells in Response To Shear Stress", J Mol Cell Cardiol. 74 (2014) 4-12.
CN-Bio, "Transforming Drug Discovery and the Lives of Patients"; 5 Pages; (2020) http://cn-bio.com/.
Colazzo et al, "Shear Stress and Vegf Enhance Endothelial Differentiation of Human Adipose-Derived Stem Cells", Growth Factors, 2014, 32(5):139-149.
Corning@ HTS TRANSWELL®-96 Tissue Culture Systems, Permeable Supports for High Throughput Screening Applications; 2 Pages (2004).
Tissue Dynamics; "Disruptive Drug Development"; 3 Pages; (Downloaded Mar. 9, 20); https://www.issuedynamics.com/.
Domansky et al., "Perfused Multiwell Plate for 3D Liver Tissue Engineering", Lab Chip, 2010, 10:51-58.
Emulate; 6 Pages; (2019) https://emulatebio.com/.
Tissuse; "Emulating Human Biology, Pioneering Human-On-A-Chip Developments"; 1 Page; (Downloaded Mar. 9, 2020) https://www.tissuse.com/en/.
GeoCHEM Incorporated, Product Line; https://www.geocheminc.com, 4 Pages; (2020).
HμREL ® Corporation, Bioanalytic Tools Company; 2 Pages; (2013); http://hurelcorp.com/.
Jeon et al, "Combined Effects of Flow-Induced Shear Stress and Micropatterned Surface Morphology On Neuronal Differentiation of Human Mesenchymal Stem Cells" J Biosci Bioeng, 2014, 117(2):242-247.
Jiang et al, "Shear Enhances Thrombopoiesis and Formation of Microparticles That Induce Megakaryocytic Differentiation of Stem Cells", Blood, Sep. 25, 2014; 124(13):2094-2103.
Kim et al, "Shear Stress Induced By an Interstitial Level of Slow Flow Increases the Osteogenic Differentiation of Mesenchymal Stem Cells Through Taz Activation" PLoS ONE, Mar. 21, 2014; 9(3), e92427, 9 pages.
Liquid Surge Control, LLC; "The Latest in Drop-In Baffle Technology"; 2 Pages; (2019).
Elveflow; "Microfluidics Innovation Center"; 6 Pages; (Downloaded Mar. 9, 2020); https://www.elveflow.com/.
Nortis; "Bridging the Gap Between in Vitro and in Vivo Research" ; 16 Pages; (2015); https://www.hortisbio.com/.
Mimetas the Organ-On-A-Chip Company; "Organ-On-A-Chip Models for Science and Pharma"; 4 Pages; (Downloaded Mar. 9, 2020); https://mimetas.com/.
Organovo; "Pioneering Bioprinted Tissues To Treat Disease "; 2 Pages; (Downloaded Mar. 9, 20) http://organovo.com/.
Satoh et al., "A Pneumatic Pressure-Driven Multi-Throughput Microfluidic Circulation Culture System" Lab Chip, 2016, 16, 2339-2348.
Tara; "Innovating Predictive Cardiac Physiology"; 4 Pages; (2019) http://tarabiosystems.com/.
The Lab Depot® Products for Discovery Lab Supplies; Shake Flasks, 3 AND 4 Baffles Product Information; 5 Pages (2019).
Wikipedia; "Antiroll Tanks"; 3 Pages; Page Last Edited May 23, 2019.
Wrighton et al, "Forces of Change: Mechanics Underlying Formation of Functional 3D Organ Buds" Cell Stem Cell, May 7, 2015; 16(5):453-454.
AxoSIM, Nerve-On-A-Chip Mini-Brain About Team; 6 Pages; (Downloaded Mar. 9, 2020); http://axosim.com/.
Corning Life Sciences Product Portfolio; 5 Pages Saved Mar. 6, 2020.
Achilli; "Advances in the Formation, Use and Understanding of Muli-Cellular Spheroids" , Expert Opin. Biol. Ther. (2012) 12 (10) 1347-1360.
Alepee et al. "State of the art 3D cultures (organs-on-a-chip) in safety testing and pathophysiology" Trnasatlantic Think Tank for Toxicology, t4 Workshop Report, Altex 31 4/14, pp. 441-477, retrieved from: http://dx.doi.org/10.14573/altex1406111 (Jul. 14, 2014.
G-Plate: Accelerate your cell cultures to the next dimension, "An original cell culture model allowing for inland shaped 3D cell aggregates" 1 page, retrieved Sep. 8, 2015.
Anada et al; "An Oxygen-Permeable Spheroid Culture System for the Prevention of Central Hypoxia and Necrosis of Spheroids"; Biomterials, 33, (2012) 8430-8441.
Bartosh et al; "Aggregation of Human Mesenchymal Stromal Cells (MSCS) Into 3D Spheroid Enhances Their Antiinflammatory Properties" ; Pnas, Aug. 3, 2010, vol. 107, No. 31 pp. 13724-13729.
Madoux et al; "Building Phenotypic 3D Spheroid Hts Assays To Identify Synthetic Lethal Small Molecule Inhibitors of Kras "; The Scripps Research Institute Molecular Screening Center and Department of Cancer Biology, Scripps Florida, Jupiter, Florida, Department of Pathology, Jupiter Medical Center, Jupiter, Florida.
Carver et al.; "Multicellular Tumor Spheroids as a Model for Assessing Delivery of Oligonucleotides in Three Dimensions"; Molecular Therapy-Nucleic Acids (2014) 3, E153; 8 Pages.
Chen et al. "Microfluidic array for 3-dimensional perfusion culture of human mammary epithelial cells" , Biomedical Microdevices (2011) vol. 13, issue 4. p. 753-758.
Choi et al., "Feasibility of a simple double-layered coculture system incorporating metabolic processes of the intestine and liver tissue: application to the analysis of benzo[a]pyrene toxicity" Toxicology in Vitro, vol. 18, pp. 393-402, 2004.
Dolznig and Walzl, "Organotypic spheroid cultures to study tumor-stroma interactions during cancer development." Drug discovery today, V 8., No. 2-3, 2011, 113-118.

(56) References Cited

OTHER PUBLICATIONS

Endo et al., "Gene transfection to spheroid culture system on micropatterned culture plate by polyplex nanomicelle: a novel platform of genetically-modified cell transplantation", Drug Deliv. and Transl. Res., 2012, vol. 2, p. 398-405.
Engelberg and Ropella, "Essential operating principles for tumor spheroid growth." BMC Systems Biology 2008, 2, 110.
Friedrich et al "Experimental anti-tumor therapy in 3-D: spheroidsold hat or new challenge?" Int J Radiat Biol 2007, 83:849-871.
Friedrich et al. "Spheroid based drug screen: considerations and practical approach." Nature protocols, 2009, vol. 4 No. 3, 309-323.
Frith et al. "Dynamic three-dimensional culture methods enhance mesenchymal stem cell properties and increase therapeutic potential." Tissue engineering, 2010, 16, No. 4, 735-749.
Fukuda et al. "Efficacy of a polyurethane foam/spheroid artificial liver using human hepatoblastoma cell line (HepG2)." Cell Transplant 2003; 12:518.
Haycock. "3D cell culture: a review of current approaches and techniques." Methods Mol Biol. 2011;695:1-15.
Hirschhaeuser et al., "Mulicellular tumor spheroids: An underestimated tool is catching up again." Journal of Biotechnology, 2010, 148, 3-15.
Howes et al; "3-Dimensional Culture Systems for Anit-Cancer Compound Profiling and High-Throughput Screening Reveal Increases in EGFR Inhibitor-Mediated Cytotoxicity Compared To Monolayer Culture Systems"; PLOS ONE; Sep. 2004, vol. 9, Issue 9, 11 Pages.
Hribar et al; "Nonlinear 3D Projection Printing of Concave Hydrogel Microstructures for Long-Term Multicellular Spheroid and Embryoid Body Culture"; Lab Chip, 2015, 15, 2412-2418.
Hwang et al; "Microwell-Mediated Control of Embryoid Body Size Regulates Embryonic Stem Cell Fate Via Differential Expression of WNT5A and WNT11"; PNAS; Oct. 6, 2009, vol. 106, No. 40, pp. 16978-16983.
Kelm et al. "Method for generation of homogeneous multicellular tumor spheroids applicable to a wide variety of cell types." Biotechnol Bioeng 2003;83:17380.
Koide et al. "Formation of multicellular spheroids composed of adult rat hepatocytes in dish with positively charged surfaces and under other nonadherent environments." Exp Cell Res 1990; 186: 22735.
Kunz-Schughart et al "The use of 3-D cultures for high-throughput screening: the multicellular spheroid model." J Biomol Screen 2004, 9:273-285.
Kutsuzawa et al; "Highly Robust Protein Production By Co-Culture of Cho Spheroids Layared On Feeder Cells in Serum-Free Medium"; Colloid Polym Sci (2014) 292; 839-848.
Labusca et al. "Scaffold-free culture of mesenchymal stem cell spheroids in suspension preserves multilineage potential", Cell Tissue Res. Mar. 2012 ; 347(3): 701711.
Landry et al. "Spheroidal aggregate culture of rat liver cell: histotypic reorganization, biomatrix deposition, and maintenance of functional activities." J Cell Biol 1985;101:91423.
Lau et al., "Evaluation of a Novel in Vitro CACO-2 Hepatocyte Hybrid System for Predicting in Vivo Oral Bioavailability" Drug Metabolism and Disposition, vol. 32, No. 9, pp. 937-942, 2004.
Liu et al. "Quasi-spherical microwells on superhydrophobic substrates for long term culture of multicellular spheroids and high throughput assays" Biomaterials and Cancer 35 (2014) pp. 6060-6068.
Liu et al; "Advanced Micromachining of Concave Microwells for Long Term On-Chip Culture of Multicellular Tumour Spheroids", ACS Appl. Mater. Interfaces, 2014, 35 Pages.
Lu et al. "Galactosylated PVDF membrane promotes hepatocyte attachment and functional maintenance." Biomaterials 2003;24:4893903.
Markovitz-Bishitz, "A polymer microstructure array for the formation, culturing, and high throughput drug screening of breast cancer spheroids" Biomaterials and Biotechnology 31 (2010) pp. 8436-8444.
Messner et al., Multi-cell type human liver microtissues for hepatotoxicity testing. Archives of Toxicology Nov. 11, 2012.
Mironov et al; "Organ Printing: Tissue Spheroids as Buliding Blocks" Biomaterials, 2009; 30 (12) 2164-2174.
Moon et al; "Optimizing Human Embryonic Stem Cells Differentiation Efficiency By Screening Size-Tunable Homogenous Embryoid Bodies"; Biomaterials; 35 (2014) 5987-5997.
Urich et al; "Multicellular Self-Assembled Spheroidal Model of the Blood Brain Barrier"; Scientific Reports, 3, 1500, 8 Pages.
Murphy et al; "3D Bioprinting of Tissues and Organs"; Nature Biotechnology, vol. 32, No. 8, Aug. 2014, pp. 773-785.
Otsuka et al. "Two-dimensional multiarray formation of hepatocyte spheroids on a microfabricated PEG-brush surface." Chembiochem 2004;5:8505.
Peshwa et al. "Mechanistics of formation and ultrastructural evaluation of hepatocyte spheroids." In Vitro Cell Dev Biol Anim 1996;32:197203.
Rezende et al; Scalable Biofabrication of Tissue Spheroids for Organ Printing; Sciverse Science Direct, Porcedia Cirp 5, (2013) 276-281.
Sa et al. "Round-bottomed Honeycomb Microwells: Embryoid body shape correlates with stem cell fate" Journal of Developmental Biology and Tissue Engineering vol. 4(2), pp. 12-22, May 2012.
Sakai et al. "Large-scale preparation and function of porcine hepatocyte spheroids." Int J Artif Organs 1996;19:294301.
Sakai et al; "Detachably Assembled Microfluidic Device for Perfusion Culture and Post-Culture Analysis of Spheroid Array"; Biotechnol. J. 2014, 9, 971-979.
Sakai et al; "Technique for the Control of Spheroid Diameter Using Microfabricated Chips"; Sciencedirect, Acta Biomaterials 3 (2007) 1033-1040.
Sart et al. "Three-dimensional aggregates of mesenchymal stem cells: cellular mechanisms, biological properties and applications." Tissue engineering, 2013, Part B, 00, No. 00, 1-16.
Seldon et al; "Evaluation of Encapsulated Liver Cell Spheroids in a Fluidised-Bed Bioartificial Liver for Treatment of Ischaemic Acute Liver Failure in Pigs in the Translational Setting"; PLOS ONE; Dec. 2013, vol. 8, Issue 12, 12 Pages.
Takezawa et al. "Morphological and immunocytochemical characterization of a heterospheroid composed of fibroblasts and hepatocytes." J Cell Sci 1992; 101:495501.
Tobe et al. "Receptor-mediated formation of multilayer aggregation of primary rat hepatocytes on lactose- substituted polystyrene." Biochem Biophys Res Commun 1992; 184:22530.
Tong et al. "Long-term culture of adult rat hepatocyte spheroids." Exp Cell Res 1992;200:32632.
Truckemller, et al., Thermoforming of Film-Based Biomedical Microdevices, Adv. Mater. 2011, 23, pp. 1311-1329.

* cited by examiner

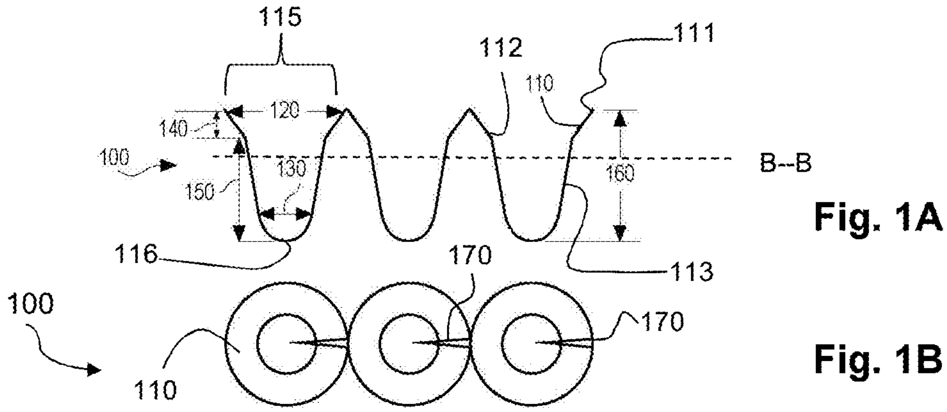
Fig. 1A
Fig. 1B
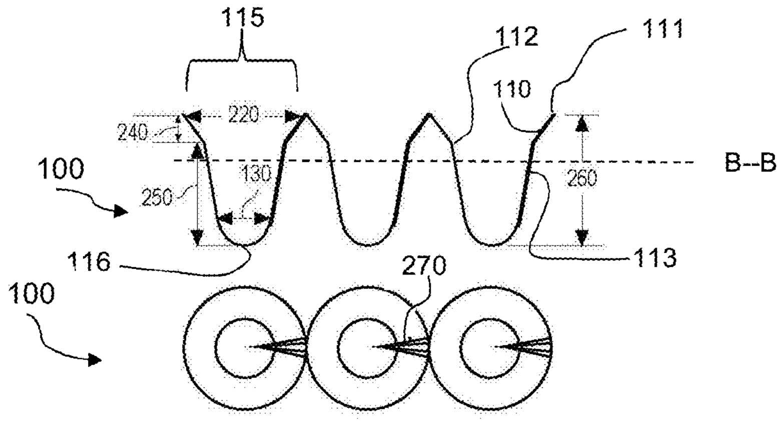
Fig. 2A
Fig. 2B

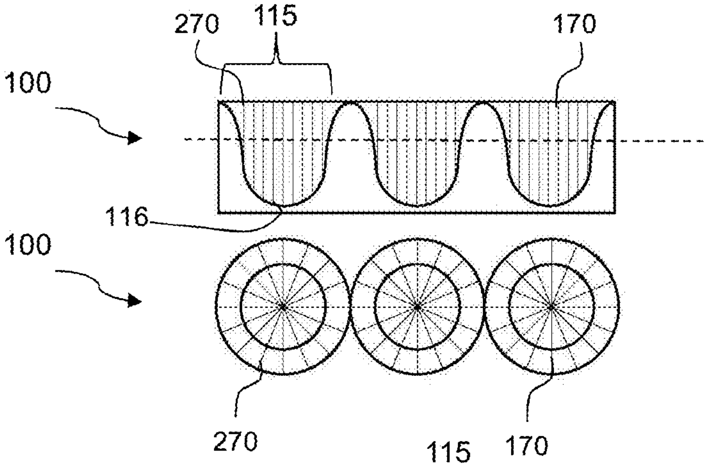
Fig. 3A
Fig. 3B
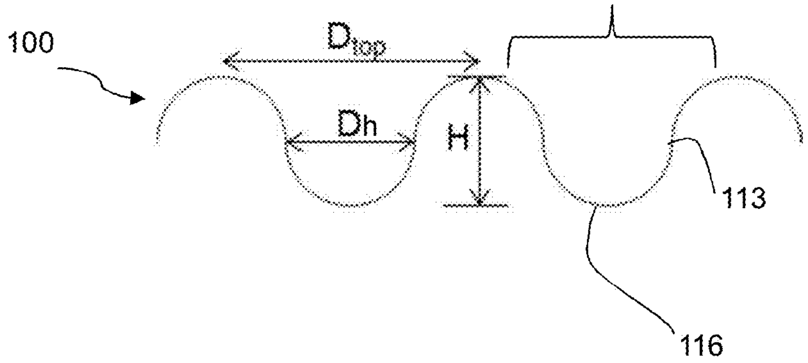
Fig. 3C
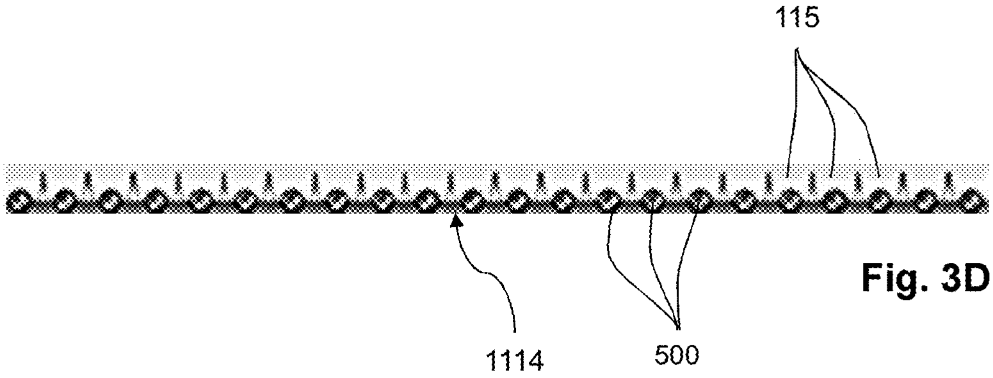
Fig. 3D

Fig. 8
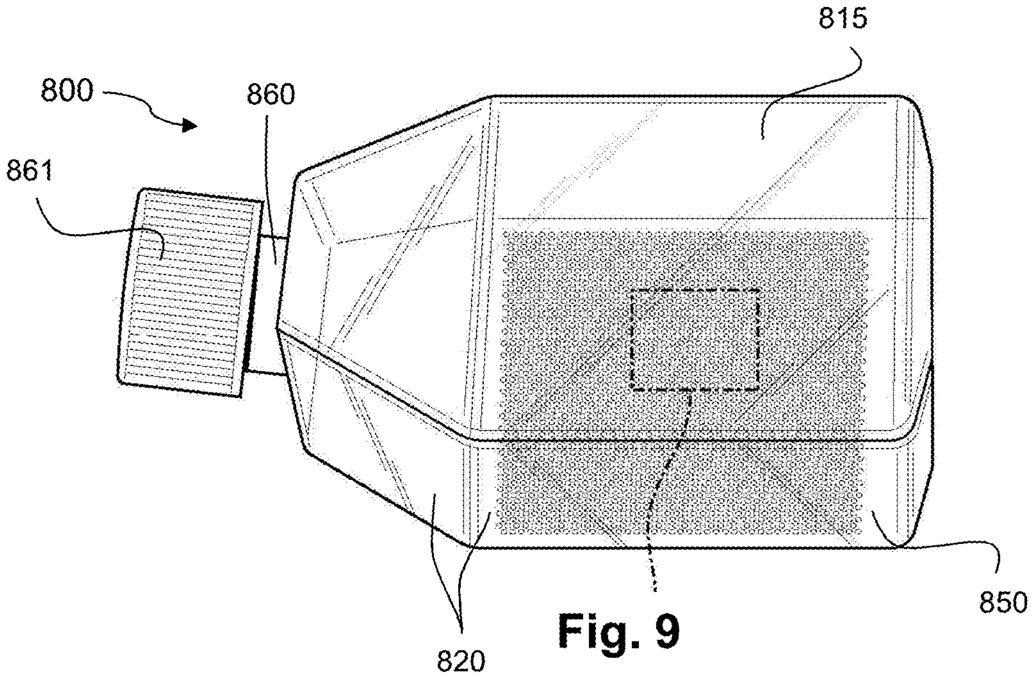
Fig. 9
Fig. 9
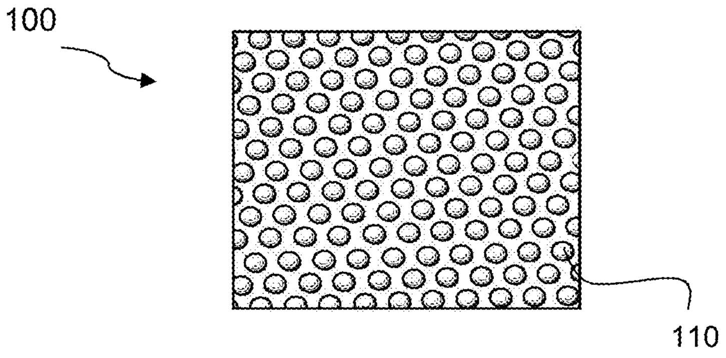

DEVICES AND METHODS FOR GENERATION AND CULTURE OF 3D CELL AGGREGATES

CROSS-REFERENCE TO RELATED APPLICATIONS

This is a continuation application of U.S. patent application Ser. No. 15/492,690 filed on Apr. 20, 2017, which claims the benefit of priority to International Patent Application Serial No. PCT/US15/58048 filed on Oct. 29, 2015, which claims the benefit of priority to U.S. Provisional Application Ser. No. 62/072,015, filed on Oct. 29, 2014, the contents of which are relied upon and incorporated herein by reference in their entirety, and the benefit of priority under 35 U.S.C. § 120 is hereby claimed.

FIELD

The present disclosure relates to apparatus, systems and methods for culturing cells. In particular, devices and methods are provided for generation and culture of 3d cell aggregates.

BACKGROUND

Three dimensional (3D) cell culture is the growth of cells in an artificially-created environment that allows the cells to grow and/or interact primarily with each other in all three dimensions. 3D cell culture represents an improvement over methods of growing cells in 2D (e.g., on a petri dish) for at least the reason that the 3D conditions more accurately model the in vivo environment.

Cells cultured in three dimensions, such as spheroids, can exhibit more in-vivo like functionality than their counterparts cultured in two dimensions as monolayers. In two dimensional cell culture systems, cells can attach to a substrate on which they are cultured. However, when cells are grown in three dimensions, such as spheroids, the cells interact with each other rather than attaching to the substrate. One issue with spheroid based assays is that the assay results typically vary with the size of the spheroid. For example, variations in variables, such as seeding density and growth time, from system to system may affect assay repeatability from system to system or from well to well within a given system. Accordingly, maintaining a consistent spheroid size between spheroids grown in separate wells can present challenges.

As the density of cells grown in cell culture apparatus increases, larger volumes of cell culture media or more frequent exchange of cell culture media may be needed to maintain the cells. However, increased frequency of media exchange can be inconvenient. In addition, increased volumes of cell culture media can lead to undesirably increased height of media above the cultured cells. As the media height increases, gas exchange rate for the cells through the media decreases.

Cells have been grown in high density as spheroid clusters in wave bags, spinners and shakers. However, the size of spheroids grown in such apparatuses is inconsistent and the shear inherent in such apparatuses tends to break spheroids into smaller clusters. Further, such apparatuses may not been able to achieve cell densities sufficiently high to satisfy current demands.

SUMMARY

The present disclosure relates to apparatus, systems and methods for culturing cells. In particular, devices and methods are provided for generation and culture of 3d cell aggregates. For example, devices and methods are provided to address issues known or unknown to the field to be detrimental to the 3D culturing of cells.

Cells cultured in three dimensions, such as spheroids, can exhibit more in vivo like functionality than their counterparts cultured in two dimensions as monolayers. In two dimensional cell culture systems, cells can attach to a substrate on which they are cultured. However, when cells are grown in three dimensions, such as spheroids, the cells interact with each other rather than attaching to the substrate. Cells cultured in three dimensions more closely resemble in vivo tissue in terms of cellular communication and the development of extracellular matrices. Spheroids thus provide a superior model for cell migration, differentiation, survival, and growth and therefore provide better systems for research, diagnostics, and drug efficacy, pharmacology, and toxicity testing.

In some embodiments, a substrate is provided that contains or comprises an array of microwells or wells. The substrate can form a part of a cell culture apparatus or device. For example, the substrate can form a part of a multiwell plate, a flask, a dish, a tube, a multi-layer cell culture flask, a bioreactor, or any other laboratory container intended to grow cells or spheroids. The microwells or wells (the term "microwell" and "well" are used interchangeably in this disclosure) are structured and arranged to provide an environment that is conducive to the formation of spheroids in culture. That is, in embodiments, the microwells have spheroid-inducing geometry. In addition, the wells are structured and arranged to provide for the movement of liquid into and out of the wells without trapping air between the substrate and liquid or liquid droplets that are introduced into the wells That is, in embodiments, the microwells have capillary structures. For example, the wells in which cells are grown can be non-adherent to cells to cause the cells in the wells to associate with each other and form spheres. The spheroids expand to size limits imposed by the geometry of the wells. In some embodiments, the wells are coated with an ultra-low binding material to make the wells non-adherent to cells.

In some embodiments, the cell culture devices have frames comprising the footprint of the device, the substrate of which is configured such that cells cultured in the devices form spheroids. For example, the cell culture substrate in the devices is non-adherent to cells to cause the cells to associate with each other instead of the substrate. The cell culture substrate is further comprised of a plurality of microwells (or wells), the geometry of which enable cells grown in the wells to form similar-sized cell aggregates or spheroids. The spheroids expand to size limits imposed by the geometry of the microwells. In some embodiments, the wells are have a low-binding treatment or are coated with an ultra-low binding material to make the wells non-adherent to cells.

Examples of non-adherent material include perfluorinated polymers, olefins, or like polymers or mixtures thereof. Other examples include agarose, non-ionic hydrogels such as polyacrylamides, polyethers such as polyethylene oxide and polyols such as polyvinyl alcohol, or like materials or mixtures thereof. The combination of, for example, non-adherent wells, well geometry (e.g., size and shape), and/or gravity induce cells cultured in the wells to self-assemble into spheroids. Some spheroids maintain differentiated cell function indicative of a more in vivo-like, response relative to cells grown in a monolayer. Other cells types, such as mesenchymal stromal cells, when cultured as spheroids retain their pluripotency, In some embodiments, the systems, devices, and methods herein comprise one or more cells. In some embodiments, the cells are cryopreserved. In some embodiments, the cells are in three dimensional culture. In some such embodiments, the systems, devices, and methods comprise one or more spheroids. In some embodiments, one or more of the cells are actively dividing. In some embodiments, the systems, devices, and methods comprise culture media (e.g., comprising nutrients (e.g., proteins, peptides, amino acids), energy (e.g., carbohydrates), essential metals and minerals (e.g., calcium, magnesium, iron, phosphates, sulphates), buffering agents (e.g., phosphates, acetates), indicators for pH change (e.g., phenol red, bromo-cresol purple), selective agents (e.g., chemicals, antimicrobial agents), etc.). In some embodiments, one or more test compounds (e.g., drug) are included in the systems, devices, and methods.

A wide variety of cell types may be cultured. In some embodiments, a spheroid contains a single cell type. In some embodiments, a spheroid contains more than one cell type. In some embodiments, where more than one spheroid is grown, each spheroid is of the same type, while in other embodiments, two or more different types of spheroids are grown. Cells grown in spheroids may be natural cells or altered cells (e.g., cell comprising one or more non-natural genetic alterations). In some embodiments, the cell is a somatic cell. In some embodiments, the cell is a stem cell or progenitor cell (e.g., embryonic stem cell, induced pluripotent stem cell) in any desired state of differentiation (e.g., pluripotent, multi-potent, fate determined, immortalized, etc.). In some embodiments, the cell is a disease cell or disease model cell. For example, in some embodiments, the spheroid comprises one or more types of cancer cells or cells that can be induced into a hyper-proliferative state (e.g., transformed cells). Cells may be from or derived from any desired tissue or organ type, including but not limited to, adrenal, bladder, blood vessel, bone, bone marrow, brain, cartilage, cervical, corneal, endometrial, esophageal, gastrointestinal, immune system (e.g., T lymphocytes, B lymphocytes, leukocytes, macrophages, and dendritic cells), liver, lung, lymphatic, muscle (e.g., cardiac muscle), neural, ovarian, pancreatic (e.g., islet cells), pituitary, prostate, renal, salivary, skin, tendon, testicular, and thyroid. In some embodiments, the cells are mammalian cells (e.g., human, mice, rat, rabbit, dog, cat, cow, pig, chicken, goat, horse, etc.).

The cultured cells find use in a wide variety of research, diagnostic, drug screening and testing, therapeutic, and industrial applications.

In some embodiments, the cells are used for production of proteins or viruses. Systems, devices, and methods that culture large numbers of spheroids in parallel are particularly effective for protein production. Three-dimensional culture allows for increased cell density, and higher protein yield per square centimeter of cell growth surface area. Any desired protein or viruses for vaccine production may be grown in the cells and isolated or purified for use as desired. In some embodiments, the protein is a native protein to the cells. In some embodiments, the protein is non-native. In some embodiments, the protein is expressed recombinantly. Preferably, the protein is overexpressed using a non-native promoter. The protein may be expressed as a fusion protein. In some embodiments, a purification or detection tag is expressed as a fusion partner to a protein of interest to facilitate its purification and/or detection. In some embodiments, fusions are expressed with a cleavable linker to allow separation of the fusion partners after purification.

In some embodiments, the protein is a therapeutic protein. Such proteins include, but are not limited to, proteins and peptides that replace a protein that is deficient or abnormal (e.g., insulin), augment an existing pathway (e.g., inhibitors or agonists), provide a novel function or activity, interfere with a molecule or organism, or deliver other compounds or proteins (e.g., radionuclides, cytotoxic drugs, effector proteins, etc.). In some embodiments, the protein is an immunoglobulin such as an antibody (e.g., monoclonal antibody) of any type (e.g., humanized, bi-specific, multi-specific, etc.). Therapeutic protein categories include, but are not limited to, antibody-based drugs, Fc fusion proteins, anticoagulants, antigens, blood factor, bone morphogenetic proteins, engineered protein scaffolds, enzymes, growth factors, hormones, interferons, interleukins, and thrombolytics. Therapeutic proteins may be used to prevent or treat cancers, immune disorders, metabolic disorders, inherited genetic disorders, infections, and other diseases and conditions.

In some embodiments, the protein is a diagnostic protein. Diagnostic proteins include, but are not limited to, antibodies, affinity binding partners (e.g., receptor-binding ligands), inhibitors, antagonists, and the like. In some embodiments, the diagnostic protein is expressed with or is a detectable moiety (e.g., fluorescent moiety, luminescent moiety (e.g., luciferase), colorimetric moiety, etc.).

In some embodiments, the protein is an industrial protein. Industrial proteins include, but are not limited to, food components, industrial enzymes, agricultural proteins, analytical enzymes, etc.

In some embodiments, the cells are used drug discovery, characterization, efficacy testing, and toxicity testing. Such testing includes, but is not limited to, pharmacological effect assessment, carcinogenicity assessment, medical imaging agent characteristic assessment, half-life assessment, radiation safety assessment, genotoxicity testing, immunotoxicity testing, reproductive and developmental testing, drug interaction assessment, dose assessment, adsorption assessment, disposition assessment, metabolism assessment, elimination studies, etc. Specific cells types may be employed for specific tests (e.g., hepatocytes for liver toxicity, renal proximal tubule epithelial cells for nephrotoxicity, vascular endothelial cells for vascular toxicity, neuronal and glial cells for neurotoxicity, cardiomyocytes for cardiotoxicity, skeletal myocytes for rhabdomyolysis, etc.). Treated cells may be assessed for any number of desired parameters including, but not limited to, membrane integrity, cellular metabolite content, mitochondrial functions, lysosomal functions, apoptosis, genetic alterations, gene expression differences, and the like.

In some embodiments, the cell culture devices are a component of a larger system. In some embodiments, the system comprises a plurality (e.g., 2, 3, 4, 5, . . . , 10, . . . , 20, . . . , 50, . . . , 100, . . . , 1000, etc.) of such cell culture devices. In some embodiments, the system comprises an incubator for maintaining the culture devices at optimal culture conditions (e.g., temperature, atmosphere, humidity, etc.). In some embodiments, the system comprises detectors for imaging or otherwise analyzing cells. Such detectors include, but are not limited to, fluorimeters, luminometers, cameras, microscopes, plate readers (e.g., PERKIN ELMER ENVISION plate reader; PERKIN ELMER VIEWLUX plate reader), cell analyzers (e.g., GE IN Cell Analyzer 2000 and 2200; THERMO/CELLOMICS CELLNSIGHT High Content Screening Platform), and confocal imaging systems (e.g., PERKIN ELMER OPERAPHENIX high throughput content screening system; GE INCELL 6000 Cell Imaging System). In some embodiments, the system comprises perfusion systems or other components for supplying, re-supplying, and circulating culture media or other components to cultured cells. In some embodiments, the system comprises robotic components (e.g., pipettes, arms, plate movers, etc.) for automating the handing, use, and/or analysis of culture devices.

In the handling of microwell format microplates or other vessels with microwells, and in particular during the addition of liquid to the microwells, care must be taken to ensure the complete displacement of air from the microwells upon introduction of aqueous liquid. Upon addition of liquid to the vessel containing wells, air may be trapped beneath the liquid but within the well (e.g., microwell), particularly if the wells have a circular cross section. The surface tension of the aqueous liquid added to the well is strong, such that drops tend to remain spherical. A spherical drop can easily block a circular hole of similar size, causing air trapping within the hole (e.g., the microwell).

In some embodiments, well geometries are provided herein that reduce the likelihood that air will become trapped in the microwell, while maintaining the cell culture characteristics of the well (e.g., utility in 3D cell culture). In some embodiments, well geometries (e.g., microwell geometries) allow for the efficient displacement of air upon introduction of liquid to the well. In some embodiments, well geometries provide pathways for the flow of liquid into the well without blocking the escape of air from the well. In some embodiments, well geometries provide pathways for trapped air to escape. In some embodiments, provided herein are a variety of well geometries that facilitate air displacement in microwells and permit the entrance of liquid into the microwells, while maintaining confinement dimensions for cell aggregation.

In embodiments, the disclosure provides devices (e.g., multiwell plates, petri dishes, flasks, multi-layer flasks, or HyperStacks) for culturing and assaying, for example, spheroidal cell masses or other aggregate cell colonies. In some embodiments, devices comprise at least one chamber (e.g., well (e.g., macrowell), flask, etc.) comprising an opening (e.g., aperture), a side wall or plurality of side walls, and a bottom surface having one or more microwells. In some embodiments, the geometry of the opening, the side wall(s), and the bottom allow for: 3D culturing of cells (e.g., cell aggregates, spheroids, etc.) within the chamber, as well as one or more (e.g., all) of: (1) displacement of air from the chamber upon dispensing of reagents (e.g., liquid reagents) into the chamber (e.g., without air becoming trapped beneath or within the liquid), (2) routes for flow of liquid into the microwell that reduce the likelihood of trapping air beneath the surface of the liquid in the microwell, (3) pathways for the escape of air upon introduction of liquid to the microwell, and/or (4) pathways for the escape of air trapped beneath the liquid surface.

In some embodiments, devices are prepared with a surface comprising one or more well (e.g., microwells) where the wells (e.g., microwells) and the surface do not have any polygonal angles (e.g., 90 degree angles).

In some embodiments, wells (e.g., microwells) have a cross-sectional shape approximating a sine wave. In such embodiments, the bottom of the well is rounded (e.g., hemispherically round), the side walls increase in diameter from the bottom of the well to the top and the boundary between wells is rounded. As such the top of the wells does not terminate at a right angle. In some embodiments, a well has a diameter D at the half-way point (also termed $D_{half\text{-}way}$) between the bottom and top, a diameter $D_{top}$ at the top of the well and a height H from bottom to top of the well. In these embodiments, $D_{top}$ is greater than D. Both the relative and absolute dimensions of the wells may be selected for the desired culturing conditions. For spheroid growth, the diameter D is preferably one to three times the desired diameter of the 3D cellular aggregate to be cultured in the well. The height H is 0.7 to 1.3 times D. The diameter $D_{top}$ is 1.5 to 2.5 times D. D is preferably 100 micrometers (μm) to about 2000 micrometers (e.g., 100, 150, 200, 250, 300, 350, 400, 450, 500, 600, 700, 800, 900, 1000, 1200, 1400, 1600, 1800, or 2000 micrometers, including ranges between any two of the foregoing values (e.g., 200-1000 μm, 200-750 μm, 300-750 μm, 400-600 μm, etc.)). However, alternative relative or absolute dimensions may be employed. For example, D may be from 1 to 10 times (e.g., 2, 3, 4, 5, 6, 7, 8, 9) the desired diameter of the cellular aggregate or any value or range therein between (e.g., 1, 1 to 1.5, 1 to 2, 2, 1 to 2.5, 1 to 3, 2 to 3, 1 to 5, 3 to 5, 2 to 7, etc.). D may be from 100 μm to 10,000 μm or any value (e.g., 100, 200, 500, 1000, 2000, 5000) or range therein between (e.g., 100-2000, 200-1000, 300-700, 400-600, 500, etc.). H may be from 0.5 to 10 times D (e.g., 0.5, 0.6, 0.7, 0.8, 0.9, 1, 1.5, 2, 2.5, 3, 4, 5, 6, 7, 8, 9, 10 or any values or ranges therein between). $D_{top}$ may be from 1.1 to 5 times D (e.g., 1.1, 1.2, 1.3, 1.4, 1.5, 1.6, 1.7, 1.8, 1.9, 2, 3, 4, 5 or any values or ranges therein between).

The barrier between contiguous wells (e.g., microwells) may have an inverse identical shape to the neighboring well, may have a larger or smaller diameter DB or may otherwise differ in shape (e.g., the shape of the well bottom may differ from the shape of the well/barriervtop, see e.g., FIG. 2A and FIG. 2B). To maximize the number of wells in a given surface, DB isvpreferably less than D. DB may be from 1.1 to 5 times larger or smaller than D (e.g., 1.1, 1.2, 1.3, 1.4, 1.5, 1.6, 1.7, 1.8, 1.9, 2, 3, 4, 5 or any values or ranges therein between).

In certain embodiments, cell culture apparatuses herein comprise a plurality of wells, each configured to cause cells cultured in the wells to form spheroids of a specified diameter. The cell culture apparatus can include a structure that defines a plurality of wells. In some embodiments, each of the plurality of wells defines a top aperture, a well-bottom, and a sidewall surface extending from the top aperture to the well-bottom. The sidewall surface defines a pen tip area between the top aperture and the well-bottom. A cell culture volume is defined by the bottom surface, a portion of the sidewall surface, and the pen tip area. In some embodiments, the pen tip area is defined by a diametric dimension in a range from 100 micrometers to 700 micrometers (e.g., 100 μm, 200 μm, 300 μm, 400 μm, 500 μm, 600 μm, 700 μm, and any ranges there between) at a height in a range from 50 micrometers to 700 micrometers (e.g., 50 μm, 75 μm, 100 μm, 200 μm, 300 μm, 400 μm, 500 μm, 600 μm, 700 μm, and any ranges there between) from the well-bottom. The sidewall surface or cell culture volume is dimensioned to control the size of a spheroid growing in each well. The pen tip area is a spheroid inducing geometry.

Embodiments provide a number of features, including, for example: no air bubble entrapment during cell seeding or media exchange, high retention of 3D cellular aggregates during media exchanges, ease of spheroid harvesting from large area surfaces, gas permeability, a media reservoir above a plurality of wells, spheroid-confining wells, and/or the ability to generate spheroids in large quantities and of uniform size.

In some embodiments, wells described herein comprise one or more capillary structures (e.g., ridge, fissure, corner, acute angle, corrugation, pillar, etc.) that extend from the top opening inside the well, and which may extend from the top opening to the wellbottom or from the top opening to the bottom of mouth, that provides a route for air to escape upon an influx of liquid into the well. Suitable well geometries within the scope of the embodiments described herein include: (a) wells having a square cross-section top opening, a rounded (e.g., concave) well-bottom, and side walls that transition from a square crosssection at the top of the well to a circular cross-section at the well-bottom; (b) wells having a one or more protruding ridgelines extending from the top opening (e.g., circular cross-section top opening) to the well-bottom (e.g., rounded (e.g., concave) well-bottom) (See, e.g., FIG. 1B); (c) wells having one or more fissures extending from the top opening (e.g., circular cross-section top opening) to the well-bottom (e.g., rounded (e.g., concave) well-bottom) (See, e.g., FIG. 2B); (d) wells having an upper portion defined by first and second sidewalls that fail to completely enclose the well, and a lower portion of the well with a rounded bottom and wherein the sidewalls completely circumscribe the well (See, e.g., FIG. 27 or FIG. 28); (e) wells in which one or more sidewalls have a convex cross-section thereby creating an acute angle between two sidewalls which may be formed by pillars (See, e.g., FIG. 5D). In some embodiments, wells comprise variations and/or combinations of the above geometries.

In embodiments, provided herein are methods for making cell culture devices comprising the wells described herein.

In embodiments, provided herein are methods for using the cell culture devices comprising the wells described herein in, for example, spheroid cell culture or in cellular assays.

In some embodiments, provided herein are cell culture devices comprising a frame having a well disposed therein, the well comprising: (a) a top opening; (b) a well-bottom having a rounded cross-sectional geometry; (c) a sidewall or sidewalls extending from the well-bottom to the top opening; (d) optionally a mouth; and (e) optionally a capillary structure that facilitates the introduction of liquid into the well and the escape of air from the well without the formation of persistent air pockets beneath the surface of the liquid.

In some embodiments, the well-bottom has a circular cross-sectional geometry, wherein the top opening has a polygonal cross-sectional geometry, and wherein the sidewalls transition from circular to polygonal cross-sectional geometry, thereby creating corners between sidewalls that serve as the capillary structures that facilitates the introduction of liquid into the well and the escape of air from the well. In some embodiments, the transition of the sidewall cross-sectional geometry does not present obstructions to the flow of fluid into or out of the well. In some embodiments, the top opening has a square or hexagonal cross-sectional geometry.

In some embodiments, the structural feature that facilitates the introduction of liquid into the well and the escape of air from the well is a ridge protruding from the sidewall or sidewalls and extending from well-bottom to the top opening. In some embodiments, wells comprise 1-20 ridges (e.g., 1, 2, 3, 4, 5, 6, 7, 8, 9, 10, 11, 12, 13, 14, 15, 16, 17, 18, 19, 20) protruding from the sidewall or sidewalls and extending from well-bottom to the top opening, or substantially so. In some embodiments, the well-bottom has a circular cross-sectional geometry and the top opening has a circular or polygonal cross-sectional geometry. In some embodiments, the ridges are symmetrically spaced around the perimeter of the well. In some embodiments, the ridges are asymmetrically spaced around the perimeter of the well. In some embodiments, the ridges do not span the entire distance from top opening to well-bottom.

In some embodiments, the structural feature that facilitates the introduction of liquid into the well and the escape of air from the well is a fissure within the sidewall or sidewalls and extending from well-bottom to the top opening. In some embodiments, wells comprise 1-20 fissures (e.g., 1, 2, 3, 4, 5, 6, 7, 8, 9, 10, 11, 12, 13, 14, 15, 16, 17, 18, 19, 20) within the sidewall or sidewalls and extending from well-bottom to the top opening. In some embodiments, the well-bottom has a circular cross-sectional geometry and the top opening has a circular or polygonal cross-sectional geometry. In some embodiments, the fissures are symmetrically spaced around the perimeter of the well. In some embodiments, the fissures are asymmetrically spaced around the perimeter of the well. In some embodiments, the fissures do not span the entire distance from top opening to well-bottom.

In some embodiments, the well is defined by 3 or more adjacent pillars (e.g., 3, 4, 5, 6, 7, 8, 9, 10), a portion of the side of each pillar forming the sidewalls of the well; and wherein a confined space between adjacent pillars forms the structural feature that facilitates the introduction of liquid into the well and the escape of air from the well. In some embodiments, the well-bottom has a circular cross-sectional geometry and extends below the pillars.

In some embodiments, provided herein are cell culture devices comprising a frame comprising a plurality of wells disposed therein; wherein the wells are arranged in at least one row; wherein the row is defined by two corrugated sidewalls aligned to such that the gap between the sidewalls widens and narrows with each corrugation; wherein an upper portion of each well defined by a widened gap between two narrowed gaps of the sidewalls, such that the upper portion of adjacent wells are in fluid communication; and wherein a lower portion of each well extends below the corrugated sidewalls and forms a circular well-bottom. In some embodiments, devices comprise multiple rows of wells.

In some embodiments, the sidewall, sidewalls, and/or well-bottom is gas permeable and liquid impermeable. That is, in some embodiments, the substrate from which the wells are formed is gas permeable and liquid impermeable.

In some embodiments, the sidewall or sidewalls is opaque and the well-bottom is transparent.

In some embodiments, the well-bottom comprises a concave arcuate surface.

In some embodiments, the sidewall, sidewalls, and/or well-bottom comprises a low-adhesion or no-adhesion material and/or is coated with a low-adhesion or no-adhesion material.

In some embodiments, a cell culture device comprises from 8 to about 10,000 wells (8, 16, 24, 32, 48, 64, 96, 128, 256, 384, 500, 600, 700, 800, 1000, 1536, 2000, 2400, 3200, 4000, 10000, or any ranges therein).

In some embodiments, surfaces with microwell patterns are incorporated into a wide range of cell culture products. In some embodiments, the bottoms of wells (e.g., macrowells) in, for example, 12-, 24-, and 6-well plates are patterned with microwell surfaces. In some embodiments, microwell surfaces are incorporated into large surface area cell culture vessels, such as T25, T75, T125, T175 and T250 flasks as well as CellSTACK and HYPERStack lines of products. In some embodiments, culture of cells in large surface area vessels having a number of said microwells yields large quantities of 3D cellular aggregates applicable in cell therapy applications, clonogenic culture, stem cell niches, or niche cells co-culture.

In some embodiments, cell culture devices herein comprise a bottom plate defining a major surface, one or more sidewalls extending from the bottom plate defining a reservoir, and a plurality of wells formed in the major surface. Each well defines an upper aperture co-planar with the major surface and open to the reservoir, and a well-bottom nadir positioned below the major surface. In contrast to conventional well plates, the plates described herein define a reservoir above the surface of the wells, which allows for increased volumes of cell culture media to be used and thus provides for less frequent media exchange. See, for example, FIG. 28.

In various embodiments, cell culture apparatuses having one or more cell culture compartments are described. In some embodiments, cell culture compartments are stacked. In some embodiments, each cell culture compartment includes a substrate defining a structured surface defining a plurality of gas permeable wells. In some embodiments, the wells are in gaseous communication with an exterior of the apparatus, either directly, via gas permeable materials, or via a vent or tracheal space. In some embodiments, cell culture apparatuses having, at least in part, a substrate having an array of microwells which wells are made from gas permeable materials are described. Accordingly, in some embodiments, the apparatuses are used to culture cells within the wells while having a height of cell culture media above the cultured cells that would be too high in existing cell culture apparatuses for efficient metabolic gas exchange. Because the cells are cultured in gas permeable wells that are in gaseous communication with the exterior of the apparatus, gas exchange occurs through the wells to overcome deficiency in gas exchange through the cell culture media due to the height of media above the cells.

In certain embodiments, a cell culture apparatus includes one or more cell culture compartments. In some embodiments, each cell culture compartment has an interior and includes a substrate having a first major surface and an opposing second major surface; the first major surface defines a structured surface within the interior of the compartment. In some embodiments, the structured surface defines a plurality of gas permeable wells. In some embodiments, wells are in gaseous communication with an exterior of the apparatus.

In some embodiments, provided herein are methods of culturing spheroids, comprising: charging a cell culture device described herein with culture media; and adding spheroid forming cells to the culture media. In some embodiments, methods further comprise replacing/exchanging media (e.g., daily, continuously, etc.).

In some embodiments, provided herein is the use of a cell culture device described herein for the culturing of spheroids.

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE DRAWINGS

FIG. 1A and FIG. 1B are schematic drawings of an exemplary embodiment of an array of wells 100. FIG. 1A is an illustration in cross-section. FIG. 1B is a top-down drawing of the exemplary embodiment of an array of wells, taken at line B-B of FIG. 1A.

FIG. 2A and FIG. 2B are schematic drawings of another exemplary embodiment of an array of wells 100. FIG. 2A is an illustration in cross-section. FIG. 2B is a top-down drawing of the exemplary embodiment of an array of wells, taken at line B-B of FIG. 2A.

FIGS. 3A, 3B, 3C and 3D are schematic drawings of another exemplary embodiment of an array of wells 100. FIG. 3A is an illustration in cross-section. FIG. 3B is a top-down drawing of the exemplary embodiment of an array of wells, taken at line B-B of FIG. 3A. FIG. 3C is a drawing of an array of wells having a sinusoidal or parabolic shape. FIG. 3D is a side view of an array of wells containing spheroids, in an embodiment.

FIG. 4A and FIG. 4C are a top-down views of a corrugated embodiment of a substrate having an array of wells, and FIG. 4B and FIG. 4D are partial cutaway views of the same embodiment.

FIGS. 5A and 5B are top-down views and FIGS. 5C, 5D and 5E are partial cut-away perspective views of exemplary embodiments.

FIG. 8 shows a culture flask having a bottom surface micropatterned with an array of microwells.

FIG. 9 shows a magnified view of the substrate, micropatterned with an array of microwells, forming the bottom surface of the flask shown in FIG. 9.

FIG. 11A shows human ESC cells and FIG. 11B shows mouse ESC cells.

DETAILED DESCRIPTION

Figure 4A:
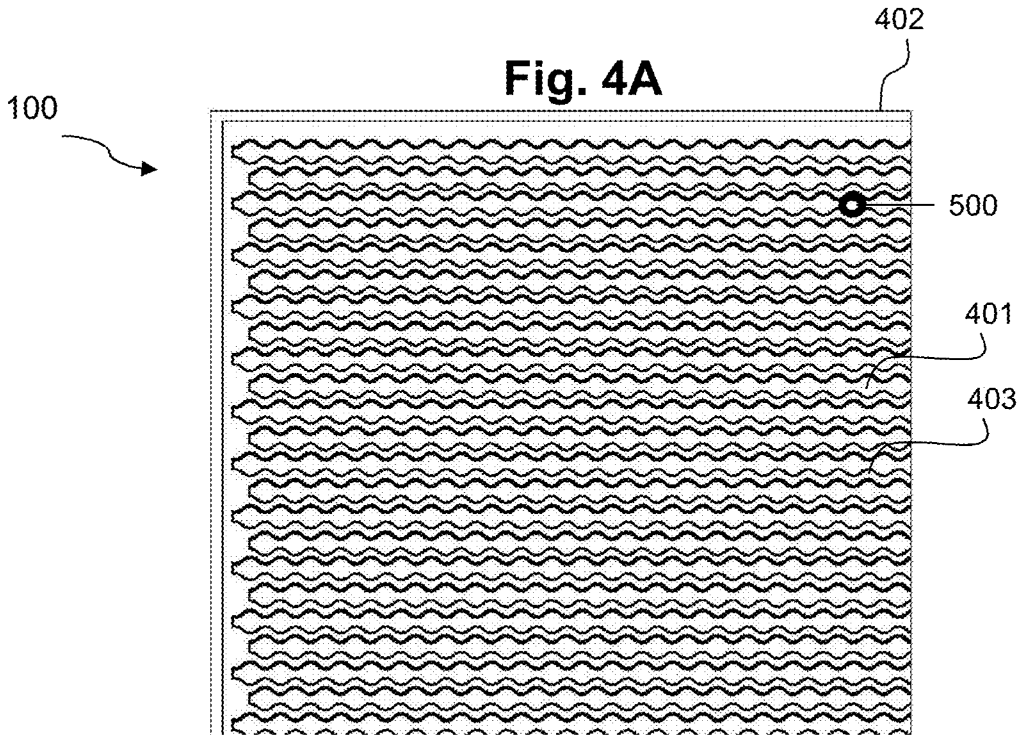
FIGS. 4A, 4B, 4C and 4D are schematic drawings showing another exemplary embodiment of an array of spheroid-containing cell culture compartments, or wells, a corrugated embodiment.

Various embodiments of the disclosure will be described in detail with reference to drawings. Reference to various embodiments does not limit the scope of the invention. Additionally, any examples set forth in this specification are not limiting and merely set forth some of the many possible embodiments of the claimed invention. Like numbers used in the figures refer to like components, steps and the like. However, it will be understood that the use of a number to refer to a component in a given figure is not intended to limit the component in another figure labelled with the same number. In addition, the use of different numbers to refer to components is not intended to indicate that the different numbered components cannot be the same or similar to other numbered components.

All scientific and technical terms used herein have meanings commonly used in the art unless otherwise specified. The definitions provided herein are to facilitate understanding of certain terms used frequently herein and are not meant to limit the scope of the present disclosure.

In certain embodiments, the apparatuses herein and the methods of making and using such apparatuses provide one or more advantageous features or aspects, including for example as discussed below. Features or aspects recited in any of the claims are generally applicable to all facets of the invention. Any recited single or multiple feature or aspect in any one claim can be combined or permuted with any other recited feature or aspect in any other claim or claims.

"Include," "includes," or like terms means encompassing but not limited to, that is, inclusive and not exclusive.

"About" modifying, for example, the quantity of an ingredient in a composition, concentrations, volumes, process temperature, process time, yields, flow rates, pressures, viscosities, and like values, and ranges thereof, or a dimension of a component, and like values, and ranges thereof, employed in describing the embodiments of the disclosure, refers to variation in the numerical quantity that can occur, for example: through typical measuring and handling procedures used for preparing materials, compositions, composites, concentrates, component parts, articles of manufacture, or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture.

"Optional" or "optionally" means that the subsequently described step, feature, condition, characteristic, or structure, occurs/is present or does not occur/is not present, while still being within the scope described.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the inventive technology.

The devices, the methods of making the devices, and the method of using the devices, described herein may include components or steps described herein, plus other components or steps not described herein.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "has", "having", "include", "includes", "including", "comprise", "comprises", "comprising" or the like are used in their open ended inclusive sense, and generally mean "include, but not limited to", "includes, but not limited to", or "including, but not limited to".

Ranges can be expressed herein as from "about" one particular value, and/or to "about" another particular value. When such a range is expressed, examples include from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The indefinite article "a" or "an" and its corresponding definite article "the" as used herein means at least one, or one or more, unless specified otherwise.

Abbreviations, which are well known to one of ordinary skill in the art, may be used (e.g., "h" or "hrs" for hour or hours, "g" or "gm" for gram(s), "mL" for milliliters, and "rt" for room temperature, "nm" for nanometers, and like abbreviations).

Specific and preferred values disclosed for components, ingredients, additives, dimensions, conditions, and like aspects, and ranges thereof, are for illustration only; they do not exclude other defined values or other values within defined ranges, unless otherwise noted. The apparatus and methods of the disclosure include any value or any combination of the values, specific values, more specific values, and preferred values described herein, including explicit or implicit intermediate values and ranges there between.

Also herein, the recitations of numerical ranges by endpoints include all numbers subsumed within that range (e.g., 1 to 5 includes 1, 1.5, 2, 2.75, 3, 3.80, 4, 5, etc.). Where a range of values is "greater than", "less than", etc. a particular value, that value is included within the range.

Any direction referred to herein, such as "top," "bottom," "left," "right," "upper," "lower," "above," below," and other directions and orientations are described herein for clarity in reference to the figures and are not to be limiting of an actual device or system or use of the device or system. Many of the devices, articles or systems described herein may be used in a number of directions and orientations. Directional descriptors used herein with regard to cell culture apparatuses often refer to directions when the apparatus is oriented for purposes of culturing cells in the apparatus.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. Any recited single or multiple feature or aspect in any one claim can be combined or permuted with any other recited feature or aspect in any other claim or claims.

It is also noted that recitations herein refer to a component being "configured" or "adapted to" function in a particular way. In this respect, such a component is "configured" or "adapted to" embody a particular property, or function in a particular manner, where such recitations are structural recitations as opposed to recitations of intended use. More specifically, the references herein to the manner in which a component is "configured" or "adapted to" denotes an existing physical condition of the component and, as such, is to be taken as a definite recitation of the structural characteristics of the component.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a cell culture apparatus comprising a structure defining a plurality of wells include embodiments where cell culture apparatus consists of a structure defining a plurality of wells and embodiments where a cell culture apparatus consists essentially of a structure defining a plurality of wells.

In various embodiments, the disclosure describes devices, such as cell culture apparatuses, including a substrate defining a well (e.g., a microwell). The well comprises a sidewall (or sidewalls), well-bottom (or nadir), and an open top (e.g., upper aperture). In embodiments, the well is configured to contain an aqueous liquid composition, for example, a composition employed in cell culture or cell assays. For example, an aqueous liquid composition may include a cell culture medium, buffers or other solutions or mixtures employed in cell assays.

The embodiments described herein find use, for example, with any device that comprises small (e.g., microscale) wells or other vessels or chambers that are configured to contain liquid. In particular embodiments, wells of devices described herein find use in the culture of cells. More particularly, the devices and microwells therein find use in the 3D cell culture of cell aggregates or spheroids.

There are some different geometries that have been used for the culture of cells as aggregates. In some embodiments, cell aggregates are clusters of cells, embryoid bodies, or spheroids. A common geometry to form cell aggregates are hemispheres found on rounded well-bottom microplates. In some embodiments, a non-adhesive surface is used to prevent the cells from attaching to the surface. A non-adhesive material may be applied after a well or chamber (e.g., in a microplate) is manufactured, or the well or chamber material may have inherent non-attachment characteristics.

Figure 27:
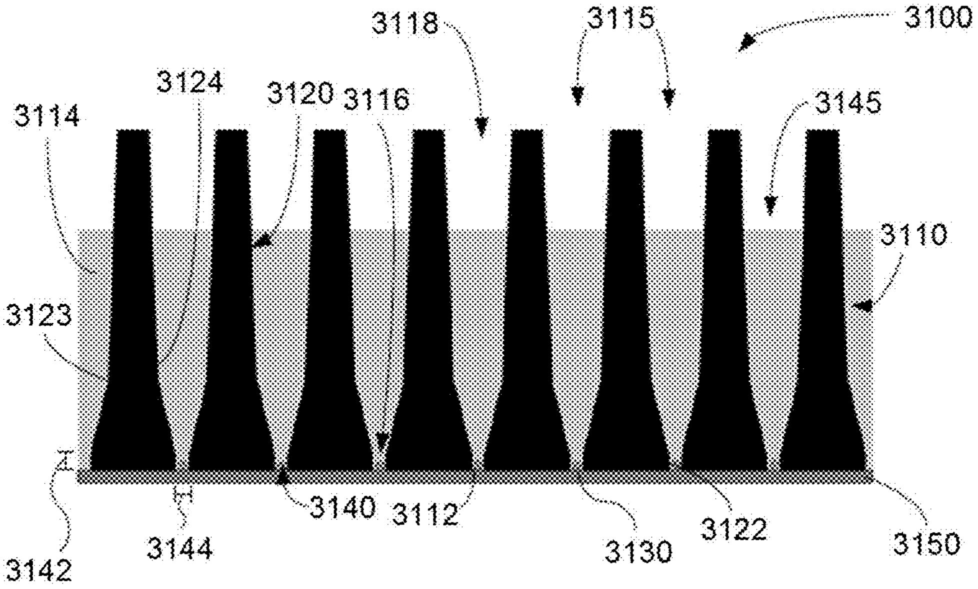
FIG. 27 is a schematic cross-sectional view of an embodiment of a plurality of wells.
Figure 28:
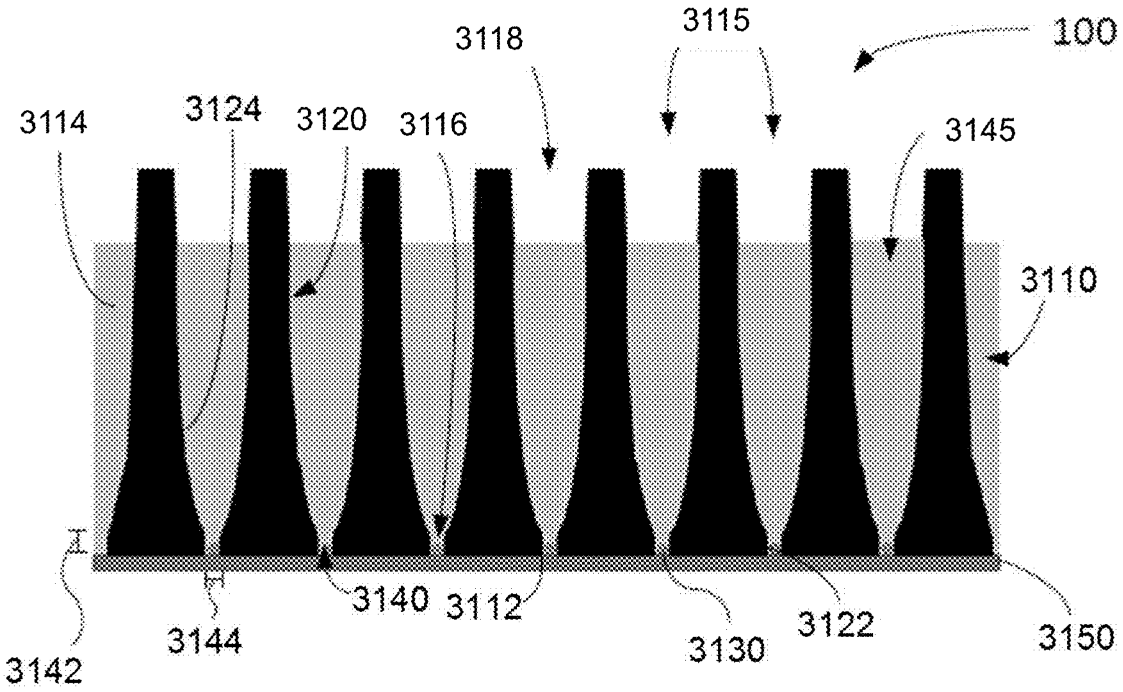
FIG. 28 is a schematic cross-sectional view of an embodiment of a plurality of wells.

FIG. 1A and FIG. 1B are is a schematic drawings of an exemplary embodiment of an array of wells 100, showing individual wells 115. In the embodiment illustrated in FIGS. 1A and 1B, well 115 has a mouth 110. Mouth 110 is a region at the top part of the well, adjacent the top opening 111 of the well 115, which provides a more open area, before the well constricts to form a well-bottom where cells settle to form spheroids. In embodiments, mouth 110 can be conical (wider at the top of the mouth than at the bottom of the mouth) and annular in shape (as shown in FIG. 1A and FIG. 2A, where the well is round). In additional embodiments, as shown in, for example, FIG. 3A, where the well has a round opening, but is parabolic in shape, mouth 110 may be parabolic or as shown in FIG. 27 and FIG. 28, mouth may extend into each well 115. In embodiments, mouth is absent. The presence of a mouth structure can provide two functions. First, the mouth widens the opening of the well, and allows liquid introduced into the opening of the well to flow down to the bottom of the well. This promotes the aggregation of cells at the bottom of the well and promotes the formation of spheroids in culture. In addition, mouth creates a transition between the annular internal surface of mouth to the internal surface of the well, thereby providing a geometric feature that may prevent the entrapment of air in the well. The presence of a 90 degree angle between the top of a well and the sidewall of a well may provide a location for formation of an air bubble. The mouth provides a transition between the top of a well and a sidewall that is not a 90 degree angle, thereby reducing the formation of air bubbles in a well having a mouth structure.

Well dimensions for use in aggregate cell culture techniques may be on the order of micrometers to millimeters (e.g., 100 μm to 50 mm). Well-containing devices for cell culture are sold by many different manufacturers (e.g., Corning, Nunc, Greiner, etc). "Microwells" are wells generally having dimensions on the order of micrometers (e.g., ≤1 mm, ≤500 μm, ≤400 μm, ≤200 μm) or a few millimeters (e.g., ≤10 mm, ≤5 mm, ≤3 mm, etc.), and are also used to grow cells as aggregates. In some embodiments, microwells provide confinements for 3D cell culture. In any suitable embodiments herein, the term "well" encompasses the use of microwells, except where described or indicated otherwise by context (e.g., where a well is described as having a well-bottom comprising a plurality of microwells). Wells intended to be outside the microwell dimensions may be referred to as "macrowells" or simply as "wells." In some embodiments, well height or well-depth (e.g., from top aperture to well-bottom) is equal to 100% or greater the well-diameter at top aperture (e.g., 100%, 110%, 120%, 130%, 140%, 150%, 160%, 170%, 180%, 190%, 200%, 225%, 250%, 275%, 300%, 325%, 350%, 375%, 400%, or any ranges there between. In some embodiments, well-depth (e.g., from top aperture to well-bottom) is equal to 100% or greater the well-diameter at the midpoint between the top aperture and well-bottom (e.g., 100%, 110%, 120%, 130%, 140%, 150%, 160%, 170%, 180%, 190%, 200%, 225%, 250%, 275%, 300%, 325%, 350%, 375%, 400%, or any ranges there between.

One of the most commonly used microwell products is the commercially available "Aggrewell" plate (sold by Stem Cell technologies), which offers a geometry that is an inverse pyramidal shape 400 or 800 micrometers in diameter arrayed in the bottom of standard format microplate wells. Another geometry for growing cells as aggregates is the "Elplasia" microplate with "microspace cell culture" (Kuraray); these plates have square microwells 200 micrometers in diameter arrayed at the bottom of standard format microplate wells that allow cells to aggregate. Various parameters, dimensions, and methods of making microwells for culturing cells as aggregates are understood in the field (U.S. Pub. No. 2004/0125266; U.S. Pub. No. 2012/0064627; U.S. Pub. No. 2014/0227784; WO2008/106771; WO2014/165273; herein incorporated by reference in their entireties). U.S. Pat. No. 6,348,999 describes micro relief elements, and how they are constructed, without stating the purpose of these constructs other than as a polymer lens array. U.S. Pat. Nos. 5,151,366, 5,272,084, and 6,306,646 describe vessels with various types of micro relief patterns to increase the surface area for cell attachment on a substrate, and the method of making the culture patterns, but the patterns themselves would not be conducive to the formation of cell aggregates. Other devices, compositions, reagents and methods have been described in the art, for example, U.S. Pub. No. 2014/0322806; U.S. Pat. No. 8,906,685; Haycock. Methods Mol Biol. 2011; 695:1-15.; U.S. Pub. No. 2014/0221225; WO 2014/165273; U.S. Pub. No. 2009/0018033; herein incorporated by reference in their entireties.

Some commercially available well geometries are conducive to the formation of cell aggregates, but not necessarily conducive to "confinement". When aggregated cells are not confined, they will usually grow as large as their surroundings will allow. Cell aggregates greater than 150 to 400 micrometers in diameter (depending on the cell type) may form necrotic cores. Necrosis occurs, for example, because the cell mass is so large that the diffusion of nutrients into the center of the aggregate and the metabolic waste out of the center of the aggregate is limited. In some embodiments, in order to create confinement, a microwell geometry is used that is very similar (e.g., within 50%, 40%, 30%, 20%, 15%, 10%, 5%, 2%, 1%, or suitable ranges therein) to the size of the maximum desired cell aggregate in diameter, but at least 1.5 to 2 times the diameter in depth (e.g., 1.5, 1.6, 1.7, 1.8, 1.9, 2.0, 2.1, 2.2, 2.3, 2.4, 2.5 2.6, 2.6, 2.8, 3.0, 3.5, 4.0, or suitable ranges therein). In some embodiments, confinement well geometry also allows for exchange of liquid culture medium through perfusion or manual pipetting without lifting the cell spheroids out of the confinement wells.

Existing devices (e.g., microwell format microplates or other vessels with microwells) exhibit a design flaw that negatively impacts the use of such devices for the formation of 3D cell aggregate structures. Although handling of microwell format microplates is fairly straightforward, failure of air to be displaced from microwells upon introduction of liquid (e.g., media) often poses problems. Air entrapment is a common problem in microplate wells with geometry as large as 384-well formats, particularly if the wells are circular. The surface tension of the aqueous liquid is strong so drops remain spherical. A spherical drop is capable of blocking a circular hole (e.g., well cross-sectional geometry) of similar size. The presence of air within the well will negatively impact and/or inhibit the culture of cells within that well.

Growing spheroids in cell culture vessels at high density on substrates with arrays of spheroid formation wells having non-adherent surfaces requires culture surfaces that balance many variables. A design that can balance, for example, maximum achievable spheroid density, ability to maintain spheroids in location during fluid exchange activities while being able to remove them when desired, and avoiding the entrapment of air in the spheroid formation wells when the vessel is filled is highly desirable to avoid difficulty in working with such vessels. Embodiments herein address the air entrapment problem of traditional wells by providing well geometries that will help displace air in microwells and permit the entrance of liquid into the microwells, while maintaining confinement dimensions. For example, square top wells with rounded well-bottom geometry are significantly less likely to entrap air when liquid is added, since the air is able to rise up the corners of the well around the aqueous droplet. In some embodiments, the inclusion of various structures (e.g., pillars, corrugations, corners, ridges, fissures, etc.) extending from the opening of the well to the well-bottom provides pathways for air escape upon introduction of liquid into the wells. In some embodiments, in addition to the features described herein, also comprise geometries, materials, etc. that are described in the art and/or understood in the field.

To avoid the issue of air entrapment in high density spheroid growth substrates, one design feature that has commonly been utilized is the avoidance of sharp corners or step changes in the substrate geometry, particularly ones that run orthogonal to the flow path of liquid across the surface. For example, the Aggrewell plate has walls that drop off at near 90 degree angles. This promotes liquid breaking from the surface as the vessel is filled leaving wells that are filled with air.

Provided herein are surface geometries that address the problem of air entrapment during liquid introduction, maintaining well features that promote growth and maintenance of high densities of discrete spheroids (e.g., rounded well-bottoms).

In some embodiments, well-shape transitioning is utilized to alleviate issues with air-escape upon introduction of liquid into the wells. For example, in some embodiments, a circular cross-section well-bottom (or bottom portion of the well) is utilized for spheroid formation. However, the circular cross-section can be particularly problematic for air escape without pocket formation. To alleviate this issue, wells are formed with a circular well-bottom cross-section and a non-circular (e.g., triangular, square, rectangular, pentagonal, hexagonal, etc.) top opening. In such embodiments, the sidewalls transition from the non-circular (e.g., polygonal) top opening to the circular well-bottom. In some embodiments, the transition is a gradual one, so as to not introduce any interfering, jagged, or horizontal-presenting sidewall features that could result in the 'hanging up' of air bubbles escaping the well upon introduction of liquid to the well. In some embodiments, the corners in the sidewalls created by the non-circular (e.g., polygonal) shape of the transitioning walls and top opening provide pathways for the entry of liquid and/or the escape of air.

In some embodiments, well geometries comprise capillary structures (including, for example, a mouth, ridge fissure, rounded or parabolic top opening, etc.) in the well walls to facilitate the escape of air upon introduction of liquid into the well. FIG. 1B is a top-down view, taken at line B-B of FIG. 1A, illustrating a ridge 170. As shown in FIG. 1B, the ridge is a bump or a protuberance from the mouth 110 or the sidewall 113 of the well. In embodiments, the ridge extends the length of the microwell from the top opening 111 to the well bottom 116. In additional embodiments, the ridge extends from the top of the mouth 111 to the bottom of the mouth 112. The sharp angles formed on either side of the ridge 170 create a capillary force on the aqueous fluid to provide for fluid entry to the microwell without air entrapment. FIG. 2B is a top-down view of an array of wells 100 shown in cross section in FIG. 2A. FIG. 2B illustrates a fissure 270. As shown in FIG. 2B, the fissure is an indentation in the sidewall 113 of the well 115. The sharp angles formed on either side of the fissure 270 create a capillary force to allow aqueous fluid flow into the microwell.

FIG. 3A, FIG. 3B, and FIG. 3C are schematic drawings of another exemplary embodiment of an array of wells 100. FIG. 3A is an illustration in cross-section. FIG. 3B is a top-down drawing of the exemplary embodiment of an array of wells, taken at line B-B of FIG. 3A. FIG. 3A and FIG. 3B illustrate that each well 115 may have more than one ridge 170 or fissure 270, and that ridges 170 or fissures 270 may be arranged in an array within the well 115. As shown in FIG. 3A and FIG. 3B, in embodiments, a radial distribution of ridges and/or fissures is envisioned. The number of capillary structures is not limited to one per microwell. In some embodiments, greater numbers of capillaries increase the rate of fluid entry into the microwell.

FIGS. 3A, 3B, 3C and 3D demonstrates inclusion of multiple (e.g., 2, 3, 4, 5, 6, 7, 8, 9, 10, 12, 16, 20, 24, 28, 32, or any ranges therein) vertically-oriented capillary structures within a single well. Features may be regularly-spaced (as depicted in FIGS. 3A, 3B, 3C and 3D), irregularly spaced, grouped/bunched, etc. In some embodiments, capillary structures extend from the top opening of the well to the well bottom. When multiple capillary structures are present in a single well, the multiple features may be of different types (e.g., ridgelines and/or fissures) and may comprise different shapes (e.g., square, rounded, etc.).

FIG. 3C illustrates that the array of wells 100 may have a sinusoidal or parabolic shape. This shape creates a rounded top edge or well edge which, in embodiments, reduces the entrapment of air at a sharp corner or 90 degree angle at the top of a well. This sinusoidal or parabolic well shape, or rounded top well edge, is also a capillary structure. As shown in FIG. 3C, the well 115 has a top opening having a top diameter $D_{top}$, a height from the bottom of the well 116 to the top of the well H, and a diameter of the well at a height half-way between the top of the well and the bottom 116 of the well $D_{half\text{-}way}$.

FIG. 3D is a schematic drawing of an array of wells, as described above in FIGS. 1A, 1B, 2A, 2B, 3A, 3B, 3C and 3D, and in embodiments. FIG. 3D illustrates a plurality of microwells 115 arranged in an array in a substrate 1114. Also shown in FIG. 3D are a plurality of spheroids 500 residing in the plurality of microwells 115.

Figure 4B:
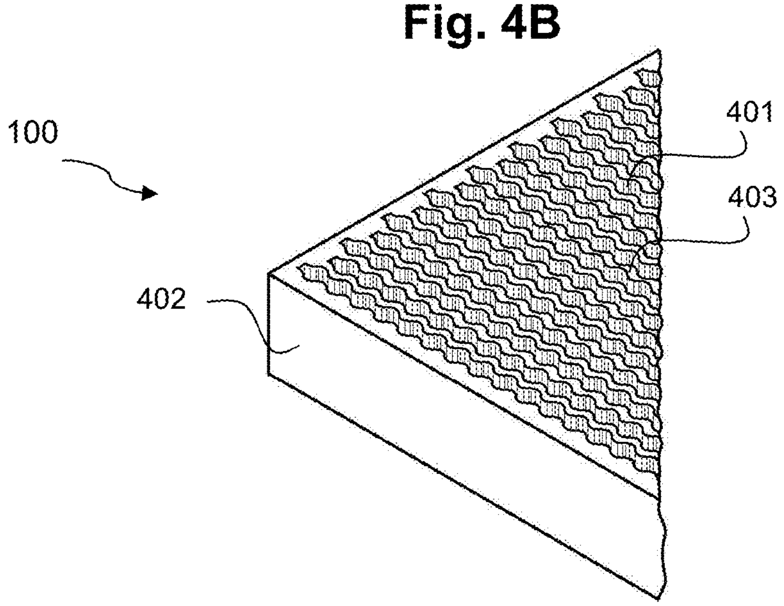
Figure 4C:
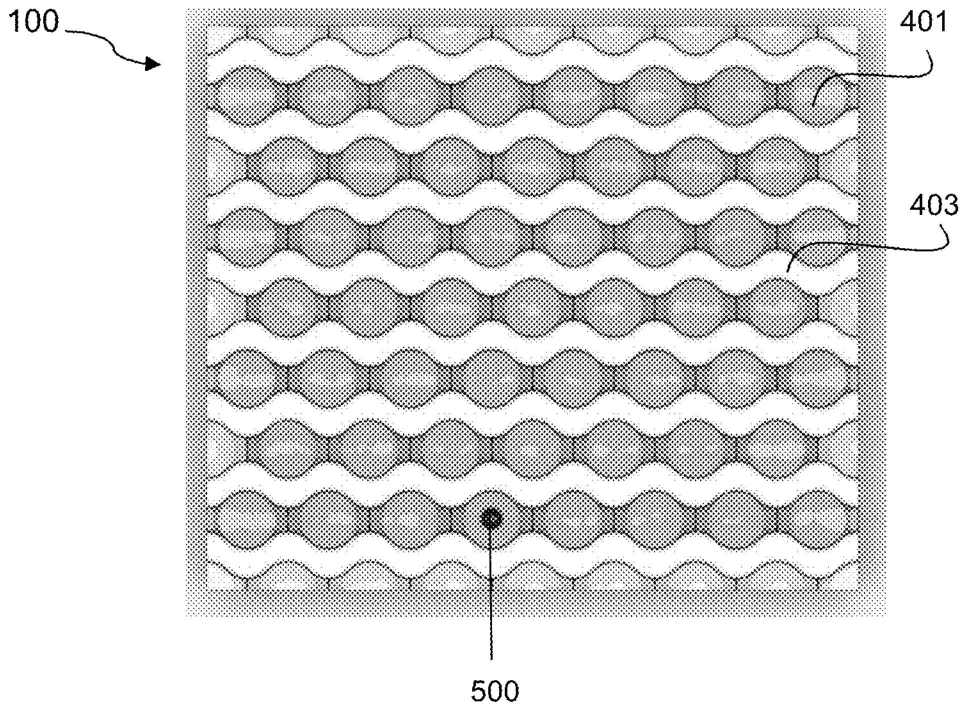
Figure 4D:
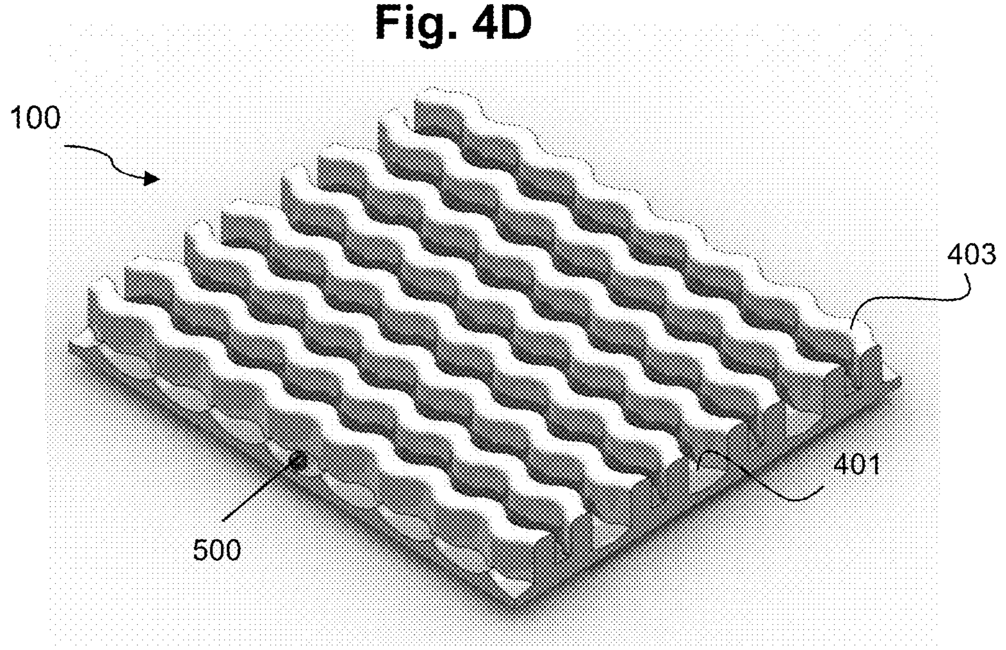

FIG. 4A and FIG. 4B are schematic drawings showing another exemplary embodiment of an array of spheroid-containing cell culture compartments, or wells. FIG. 4A is a top-down view of a corrugated embodiment of an array of wells, and FIG. 4B is a partial cut-away view of the same embodiment. In the embodiment shown in FIG. 4A and FIG. 4B, the wells are not isolated, but allow for the flow of liquid between wells. As shown in FIGS. 4A and 4B an exemplary embodiment is illustrated in which corrugated sidewalls 403 are aligned to produce microwells 401 in the gaps between the corrugated sidewalls 403. The corrugated sidewalls, shown in FIG. 4A and FIG. 4B are enclosed by a frame 402, have regions where they are far apart and then come closer together (e.g., with or without contact) in a periodicity that creates rows of microwells 401. In some embodiments, a microwell depression lies at the base of each segment that is defined by the walls being farther apart (e.g., to house a spheroid 500). FIG. 4C and FIG. 4D are additional schematic drawings of the corrugated microwell array embodiment. FIG. 4C is a top down drawing, and FIG. 4D is perspective view of the embodiment. As shown in FIG. 4D, in embodiments, no frame is present. FIG. 4C and FIG. 4D illustrate corrugated or wavy sidewalls 403 which form spaces having geometry suitable for inducing spheroid formation, 401. Also shown in FIG. 4C and FIG. 4D are spheroids 500 residing in the wells. When liquid is introduced into the embodiment shown in FIG. 4A and FIG. 4B, displaced air can move out of the local area through the areas where the walls are closer together. Movement of fluid and air to and from the wider well areas is promoted by the narrow sections, to avoid air entrapment. These corrugations also promote the formation of spheroids by providing constricted growth areas. That is corrugations are both capillary structures and spheroid inducing geometry.

Figure 5A:
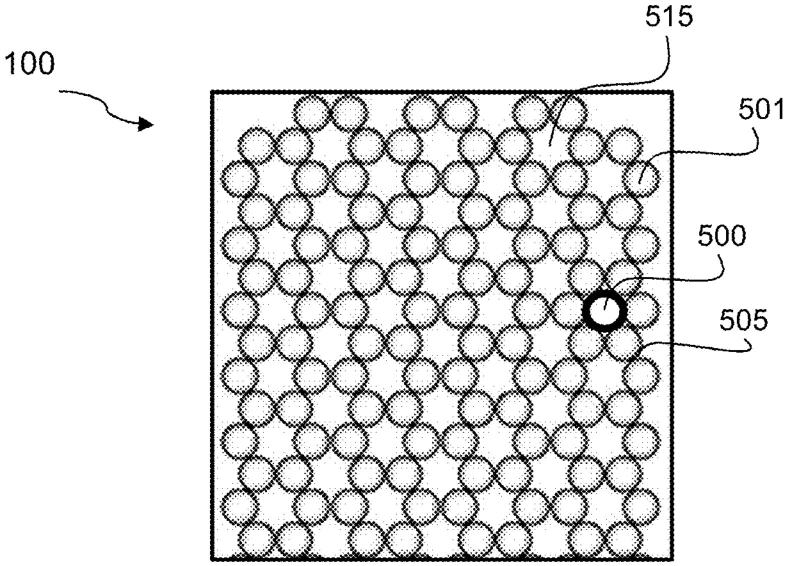
FIGS. 5A, 5B, 5C, 5D and 5E show schematic drawings of an additional exemplary embodiment in which a series of pillars define a well.
Figure 5B:
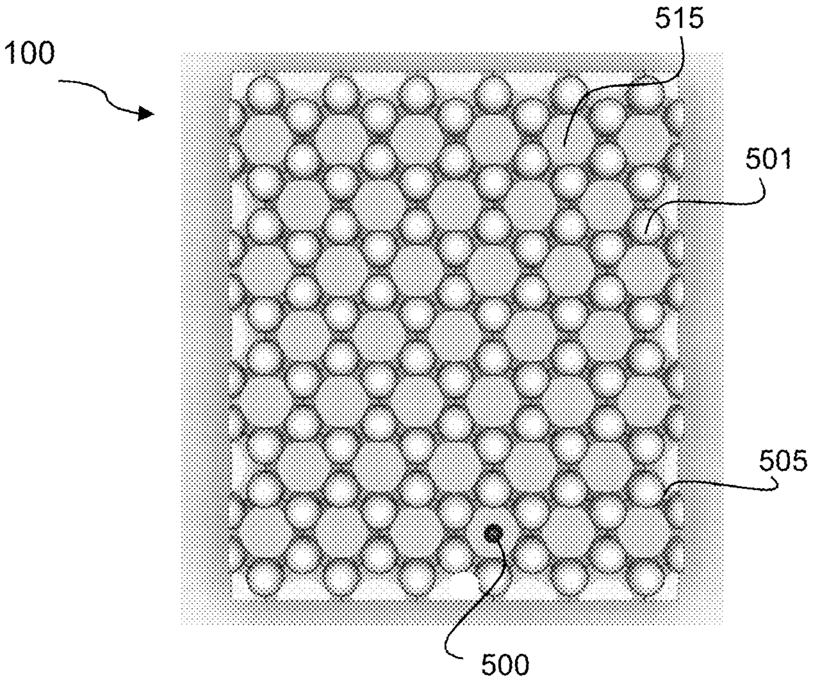
Figure 5C:
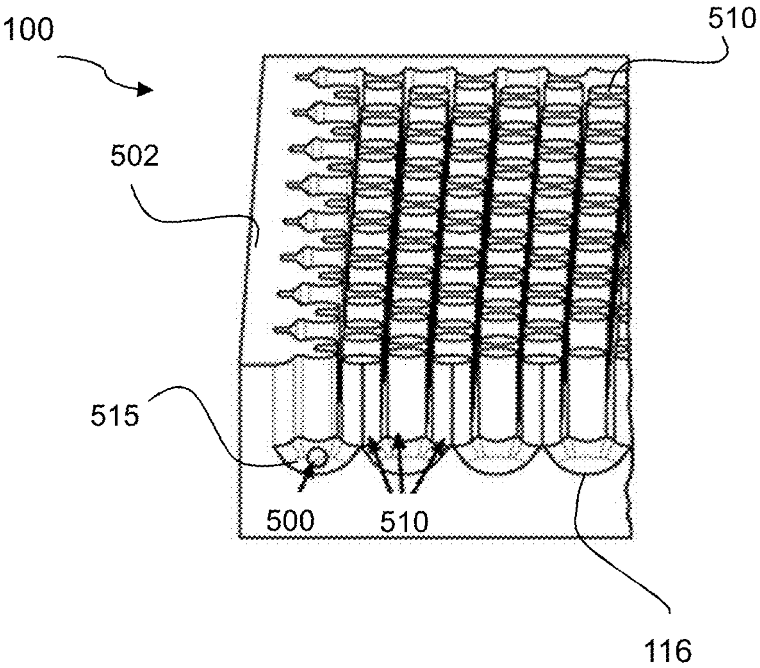
Figure 5D:
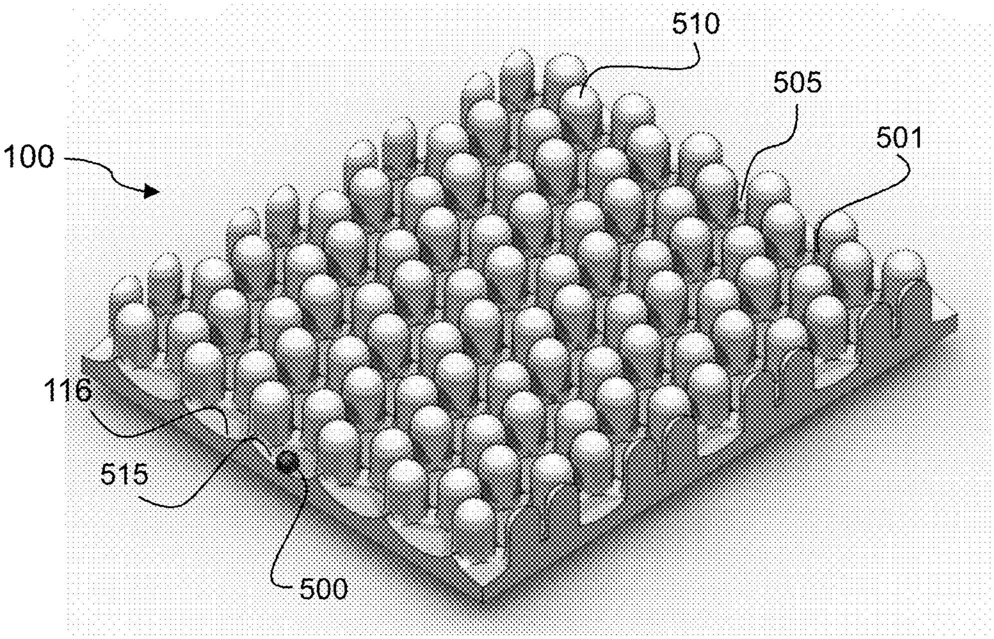
Figure 5E:
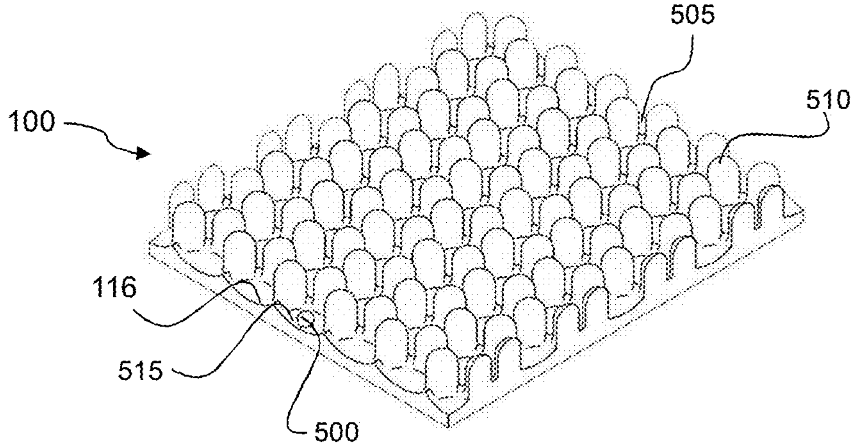
Figure 6A:
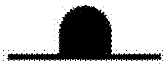
FIGS. 6A, 6B, 6C, 6D and 6E show exemplary, non-limiting examples of cross-sectional geometrics for ridges protruding from sidewalls.
Figure 6B:
Figure 6C:
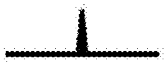
Figure 6D:
Figure 6E:
Figure 7A:
FIGS. 7A, 7B, 7C, 7D and 7E show exemplary, non-limiting examples of cross-sectional geometrics for fissures within sidewalls.
Figure 7B:
Figure 7C:
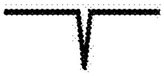
Figure 7D:
Figure 7E:

FIG. 5A and FIG. 5B show top-down schematic drawings of exemplary embodiments of an array of wells 100 in which a series of pillars define a well. FIGS. 5C, 5D and 5E are perspective drawings of embodiments of an array of microwells showing pillars 501 arranged in arrays to form wells 515. In embodiments, the tops 510 of the pillars 501 may be flat (as shown in FIG. 5A). In this embodiment, convex walls created by the pillars 501 create very acute angles or discontinuities at the junction between the pillar-formed sidewalls. FIG. 5B depicts the microwell depressions surrounded by pillars to create a confinement geometry suitable to induce the formation of spheroids 500 in culture. Air escapes and fluid enters through spaces 505 between the pillars 501. The pillars 501 have tops 510. In embodiments, the pillar tops 510 may be rounded, as shown in FIG. 5B, FIG. 5D and FIG. 5E, which would result in wells having the parabolic or sinusoidal shape shown in FIG. 3A. Pillars also promote the formation of spheroids by providing constricted growth areas. That is, pillars are both capillary structures and spheroid inducing geometry.

These structures, including, for example, ridges, fissures, bumps, divots, open ring structures at the top aperture or mouth structure, pillars, discontinuous walls, mouth structures, parabolic or sinusoidal well shape, rounded well opening, or interruptions in the smooth internal surface of a sidewall of a well, or a combination of any of these features, are capillary structures. Capillary structures also provide routes of escape for any air that might become trapped following addition of liquid. In some embodiments, discontinuous walls, walls that contain ridges or fissures or other features that interrupt the smoothness of the sidewall of a well, are used to avoid air entrapment by providing venting locations within the wells during the fill.

In some embodiments, capillary structures extend along the vertical length of walls of the wells. In some embodiments, capillary structures extend up to or above the top opening of a well. In other embodiments, capillary structures extend near the top opening of a well (e.g., <0.1, 0.1 μm, 0.2 μm, 0.5 μm, 1 μm, 2 μm, 3 μm, 4 μm, 5 μm, 10 μm, or 20 μm from the top opening (or ranges there between)). In some embodiments, capillary structures extend to the well-bottom. In other embodiments, capillary structures extend near the well-bottom (e.g., <0.1, 0.1 μm, 0.2 μm, 0.5 μm, 1 μm, 2 μm, 3 μm, 4 μm, 5 μm, 10 μm, or 20 μm from the well-bottom (or ranges there between)).

In some embodiments, capillary features provide the benefit of providing pathways for liquid entering the well to travel without entrapping air within the well. In some embodiments, capillary structures provide pathways for air to exit the well in response to the introduction of liquid entering the well. The technology is not limited to any particular mechanism of action for prevention of air entrapment, and an understanding of the mechanism is not necessary to practice the present invention.

In the event that rapid vessel fill or another fluid-introduction event leads to air entrapment, despite well geometry configured to prevent such entrapment, capillary features allow transfer of liquid under the entrapped air, thereby releasing the air from the well. For example, in the corrugated embodiment shown in FIGS. 4A, 4B, 4C and 4D, liquid and air can flow through the open well structure from one well area to the next well area through the narrowed sections of the array. Or, in the pillar embodiment shown in FIGS. 5A, 5B, 5C, 5D and 5E, liquid or entrapped air can leave a well through the spaces between pillars. In some embodiments, the downward force of liquid through the capillary structures serves to separate the air from the well wall, surrounding the air with liquid, so the air pocket rises out of the well as a bubble.

A variety of different vertically-oriented structures find use as capillary features. For example, in certain embodiments, features are raised ridges (e.g., as depicted in FIG. 1A and FIG. 1B), or sunken grooves or fissures (e.g., as depicted in FIG. 2A and FIG. 2B). Ridgelines and fissures that find use in embodiments herein are not limited to the physical geometries depicted in the figures. In some embodiments, features extend vertically along the sidewall of the well, without traversing horizontally. In most situations, horizontal structural features promote air entrapment within the wells in a similar fashion to the steep angles used in existing well geometries. Suitable cross-sectional geometries for ridges are depicted in FIGS. 6A, 6B, 6C, 6D and 6E and include: rounded (FIG. 6A), angular (FIG. 6B), needle (FIG. 6C), hemi-hexagonal (FIG. 6D and FIG. 6E), etc. Suitable cross-sectional geometries for fissures are depicted in FIGS. 7A, 7B, 7C, 7D and 7E and include: rounded (FIG. 7A), angular (FIG. 7B), needle (FIG. 7C), hemi-hexagonal (FIG. 7D and FIG. 7E), etc. Ridges and/or fissures may be of any suitable cross-sectional dimensions (e.g., having widths, lengths, etc. of 0.1-20 micrometers (e.g., 0.1, 0.2, 0.5, 1, 2, 5, 10, 15, 20, or any suitable ranges there between). Engineering and microfluidic principles may be used in combination with embodiments herein to optimize ridge and/or fissure shape and dimensions to facilitate the introduction of liquid and the exit of air without the formation of air pockets beneath the liquid surface and/or to facilitate the removal trapped air pockets.

In some embodiments, transfer of liquid into and air out of a well is mediated by discontinuous sidewall geometry. Discontinuous well geometries take the form of discontinuities in sidewalls of the wells. Examples of discontinuous sidewall geometries are as depicted in the "wave wall" or "corrugated" geometry of FIGS. 4A, 4B, 4C and 4D and the "pin wall" or "pillar wall" geometry of FIGS. 5A, 5B, 5C, 5D and 5E. These geometries are only exemplary; other sidewall orientations that introduce a gap or other discontinuity into a portion (e.g., upper portion) of the sidewall(s) may find use in embodiments herein. In these geometries, the interruption(s) in the wall allow air, with its low viscosity, to rapidly move out of the wells as the fluid enters the vessel. In some embodiments, discontinuous geometries maintain the avoidance of sharp angle changes in the substrate wall features (e.g., avoidance of features that create horizontal obstructions). In some embodiments, discontinuous sidewall geometries are used in conjunction with well-shape transitioning and/or capillary wall structure to aid bubble release and/or air exit upon liquid introduction.

In some embodiments, one or more wells have a concave surface, such as a hemi-spherical surface or a conical surface having a rounded bottom, and like surface geometries or a combination thereof. The well and well bottom can ultimately terminate, end, or bottom-out in a rounded or curved surface, such as a dimple or a well, and like concave frusto-conical relief surfaces, or combinations thereof. Other shapes and construction of spheroid-conducive wells are described in commonly-assigned U.S. patent application Ser. No. 14/087,906, which application is hereby incorporated herein by reference in its entirety to the extent that it does not conflict with the present disclosure. In embodiments, well bottoms are flat or come to a point. Well bottoms may have any other suitable shape or dimension. For example, in embodiments, well bottoms have rounded or curved surfaces, or well bottoms may have structures such as a dimple, a pit, and like, concave frusto-conical relief surfaces, dimples, or pen-tip areas or combinations thereof which promote the formation of spheroids by providing constricted growth areas. That is, rounded or curved or dimpled well bottoms, or pen tip areas or corrugations or pillars are spheroid inducing geometry.

Exemplary well geometry and size is depicted, for example, in FIG. 1A, FIG. 1B, FIG. 2A and FIG. 2B. In some embodiments, the wells 100 described herein have well-bottom diameters 130/230 ranging from about 100 micrometers to about 2000 micrometers, e.g., 100, 150, 200, 250, 300, 350, 400, 450, 500, 600, 700, 800, 900, 1000, 1200, 1400, 1600, 1800, or 2000 micrometers, including ranges between any two of the foregoing values (e.g., 200-1000 μm, 200-750 μm, 300-750 μm, 400-600 μm, etc).

Such diametric dimensions control the size of a spheroid grown therein such that cells at the interior of the spheroid are maintained in a healthy state. That is, these dimensions promote the formation of spheroids by providing constricted growth areas. That is, these dimensions are spheroid inducing geometry.

In some embodiments, the wells 100/200 described herein have top-opening cross-sectional dimensions 120/220 (e.g., diameter or width(s)) in a range from about 100 micrometers to about 2000 micrometers, e.g., 100, 150, 200, 250, 300, 350, 400, 450, 500, 600, 700, 800, 900, 1000, 1200, 1400, 1600, 1800, or 2000 micrometers, including ranges between any two of the foregoing values. In some embodiments, the wells 100 have a depth 160/260 from top opening to well-bottom in a range from about 500 micrometers to about 1500 micrometers, e.g., 100, 200, 300, 400, 500, 600, 700, 800, 900, or 1000 micrometers, including ranges between any two of the foregoing values. In some embodiments, the wells 100/200 have an upper portion with a depth 140/240 in a range from about 50 micrometers to about 500 micrometers, e.g., 50, 60, 70, 80, 90, 100, 200, 300, 400, or 500 micrometers, including ranges between any two of the foregoing values. In some embodiments, the wells 100 have a lower portion with a depth 150/250 in a range from about 100 micrometers to about 1400 micrometers, e.g., 100, 150, 200, 250, 300, 350, 400, 450, 500, 600, 700, 800, 900, 1000, 1200, or 1400 micrometers, including ranges between any two of the foregoing values. Of course, other suitable dimensions may also be employed.

In some embodiments, in addition to transition well structures and characteristics, as well as one or more design elements and/or physical features configured to allow escape of air upon introduction of liquid to a well, the devices and wells (e.g., microwells) described herein may comprise additional features to provide specialized functionality, for example, related to the 3D culture of cells within the microwells. The following paragraphs address such features that may find use in combination with the embodiments discussed above.

In some embodiments, all or a portion of the sidewalls and or well-bottom of a well is gas permeable. In some embodiments, gas permeability allows for transfer of oxygen and other gases into the well to be dissolved into the liquid or media contained within the well. The permeable sidewalls, well-bottoms, or portions thereof do not allow for the formation of air pockets or bubbles in the well liquid.

In some embodiments, cell culture apparatuses are provided having a structured surface defining a plurality of gas permeable wells. In some embodiments, the wells can comprise an exterior surface that defines an external surface of the apparatus. In some embodiments, the wells can comprise an exterior or non-culture surface that is in communication with an exterior of the apparatus. In some embodiments, provided herein are, among other things, cell culture apparatuses having a plurality of stacked cell culture compartments, each having a structured surface defining a plurality of gas permeable wells. In some embodiments, the wells in various embodiments are in gaseous communication with an exterior of the apparatus, such as indirectly through a vent or through a tracheal space, or directly through an exterior wall.

In some embodiments, wells are configured such that cells cultured in the wells form spheroids. For example, in some embodiments, the wells are non-adherent to cells to cause the cells in the wells to associate with each other (e.g., to form spheroids). The spheroids expand to size limits imposed by the geometry of the wells. In some embodiments, the wells are coated with an ultra-low binding material to make the wells non-adherent to cells.

The formation of three-dimensional (3D) cell agglomerates such as spheroids, as opposed to two-dimensional cell culture in which the cells form a monolayer on a surface, increases the density of cells grown in a cell culture apparatus, which can in turn increase nutrient demands of the cells cultured in the apparatus. Because metabolic gas exchange can occur through the gas permeable wells in which the cells are cultured, media volume in the cell culture apparatus can be greater than is possible with apparatuses in which metabolic gas exchange is essentially limited to diffusion through the cell culture medium. Accordingly, a larger cell culture medium height, and thus volume, can be used with cell culture apparatuses described herein.

In some embodiments, cells are cultured in wells of apparatuses described herein where the cell culture medium is at a height of 2 mm or more above the cells. In some embodiments, cell culture medium is at a height of 5 mm or more above the cells. A maximum cell culture medium height of 2 mm to 5 mm is generally considered an upper limit of medium height when metabolic gas exchange is essentially limited to through the medium, such as when the substrate or surface on which, or near which, the cells are cultured is impermeable or relatively impermeable (e.g., as compared to the cell culture medium) to metabolic gases.

For purposes of efficient metabolic gas exchange, in some embodiments, cells are maintained in culture in wells of apparatuses described herein when the cell culture medium in the apparatus is at any height above the cells, such as 2 mm or more above the cells, 5 mm or more above the cells or 10 mm or more above the cells. However, one of skill in the art will understand that as the height of cell culture medium in an apparatus increases above the cells, hydrostatic pressure exerted on the cells increases. Accordingly, there may be practical limitations to the height of cell culture medium above the cells. In some embodiments, the height of cell culture medium above cells cultured in wells of articles described herein is in a range from 5 mm to 20 mm, such as 5 mm to 15 mm, 6 mm to 15 mm, 5 mm to 10 mm or 6 mm to 10 mm, such as 5, 6, 7, 8, 9, 10, 15 or 20 mm, including ranges between any two of the foregoing.

In certain embodiments, a cell culture substrate or layer that has a non-culture surface in gaseous communication with an exterior of the apparatus can be adapted to have a structured surface defining gas permeable wells as described herein. Examples of such cell culture apparatuses include T-flasks, TRIPLE-FLASK cell culture vessels (Nunc., Intl.), HYPERFLASK cell culture vessels (Corning, Inc.), CELLSTACK culture chambers (Corning, Inc.), CELLCUBE modules (Corning, Inc.), CELL FACTORY culture apparatuses (Nunc, Intl.), and cell culture articles as described in WO 2007/015770, U.S. Patent Application Publication No. 2014/0315296, U.S. Pat. Nos. 8,846,399, 8,178,345, and 7,745,209, which patents and published patent applications are hereby incorporated herein by reference in their respective entireties to the extent that they do not conflict with the disclosure presented herein.

In some embodiments, gas-permeable/liquid impermeable materials are used in construction of cell culture devices herein, or portions thereof (e.g., wells, microstructures, etc.) Any suitable gas-permeable/liquid impermeable materials may find use, such as polystyrene, polycarbonate, ethylene vinyl acetate, polysulfone, polymethyl pentene (PMP), polytetrafluoroethylene (PTFE) or compatible fluoropolymer, a silicone rubber or copolymer, poly(styrene-butadiene-styrene), or polyolefin, such as polyethylene or polypropylene, or combinations of these materials. Substrate may be formed of any suitable material having a suitable gas permeability over at least a portion of the well. Examples of suitable substrates include polydimethylsiloxane (PDMS), (poly)4-methylpentene (PMP), polyethylene (PE), and polystyrene (PS). PDMS can have a high degree of gas permeability and can be achieve sufficient gas permeability at thicknesses up to 40 mm. PMP can achieve sufficient gas permeability at thicknesses up to about 01 mm. In some embodiments, PMP having a thickness in a range of about 0.02 to 1 mm. PE or PS can achieve sufficient gas permeabilities at thicknesses up to 0.2 mm, though thinner substrates may not have sufficient structural integrity. To compensate for poor structural integrity, an open frame, standoffs, or the like can be used to support the substrate from the bottom. In embodiments, a well thickness may be 0.02, 0.05, 0.1, 0.2, 0.5, 1, 2, 5, 10, 20 or 40 mm, including ranges between any two of the foregoing. In embodiments, the wells have an oxygen transmission rate through the gas permeable polymeric material of 2000 cc/m$^2$/day or greater. In some embodiments, the wells have a gas permeability through the substrate of 3000 cc/m$^2$/day or greater. In some embodiments, the wells have a gas permeability through the substrate of 5000 cc/m$^2$/day or greater.

Such materials allow effective gas exchange between outside and the internal compartments, to allow the ingress of the oxygen and other gases, while preventing the passage of liquid or contaminants.

In some embodiments, the thickness of well substrate material is adjusted to allow for optimized gas exchange. In some embodiments, well-thickness is between 10 and 100 μm (e.g., 10 μm, 15 μm, 20 μm, 25 μm, 30 μm, 35 μm, 40 μm, 45 μm, 50 μm, 60 μm, 70 μm, 80 μm, 90 μm, 100 μm, and any ranges there between). Experiments conducted during development of embodiments herein demonstrated higher numbers of viable cells produced with the thinner well-thickness (e.g., 17 μm>30 μm>57 μm).

FIG. 8 is an illustration of an embodiment of the inclusion of a substrate having an array of microwells, included as a surface of a cell culture device. In FIG. 8, the cell culture device is a flask 800. However, it should be understood that, in embodiments, the substrate may form a part of any sort of cell culture device including, without limitation, a multiwell plate, a flask, a dish, a tube, a multi-layer cell culture flask, a bioreactor, or any other laboratory container intended to grow cells or spheroids. The substrate having an array of microwells may be gas permeable material. FIG. 9 shows a magnified view of the substrate, shown at 9, micropatterned with an array of microwells, forming the bottom surface of the flask shown in FIG. 8.

With reference to the embodiments illustrated in FIG. 8 and FIG. 9, The illustrated apparatus is a flask or housing comprising a cell culture chamber 850. The housing includes a substrate having an array of microwells (shown in FIG. 9). Housing also has a top surface 815, one or more side walls 820 extending from the structured surface 110 to the top surface 815. In some embodiments, the housing 850 includes a single enclosing sidewall, such as a cylindrical wall or the like. Additional examples of such apparatuses are described in, for example, commonly-assigned U.S. provisional patent application Ser. No. 62/072,015, which provisional patent application is incorporated herein by reference in its entirety to the extent that it does not conflict with the present disclosure.

The housing includes a port 860. Shown in FIG. 8 is an opening having a screw top 861. However, in embodiments, the housing may have any type of port to allow liquid and cells to enter and exit the housing. The port 860 may be in a side wall, in the top surface 815 or in the cell culture surface 110. Port 860 may connect to tubing or other connections to introduce or remove cells and cell culture medium into the cell culture chamber 850.

While the housing depicted in FIG. 8 illustrates fixed sidewalls 820, in embodiments, the sidewalls may be flexible or expandable and collapsible to allow a variable volume of cell culture medium into the cell culture chamber 850. As additional cell culture medium is introduced into the cell culture chamber 850, via port 860, flexible sidewalls 820 may extend, and as cell culture medium is removed from the cell culture chamber 850, via port 860, flexible sidewall 820 may collapse. In some embodiments, sidewall 820 and top 815 are formed from a bag. In addition, cell culture chamber 850 can be filled with any volume of cell culture medium up to the fixed volume of the housing. In some embodiments (not shown) the entire or nearly the entire interior volume is filled with cell culture medium.

In the embodiment depicted in FIG. 8, the volume of cell culture medium in the cell culture chamber 850 is present at a height H. of medium above the cells. As described above, the height H. of medium in a housing as described herein above cultured cells can be higher than would be possible if the wells were not gas permeable. In some embodiments, the cell culture chamber 850 is filled to its capacity for purposes of culturing cells within the apparatus.

Figure 10A:
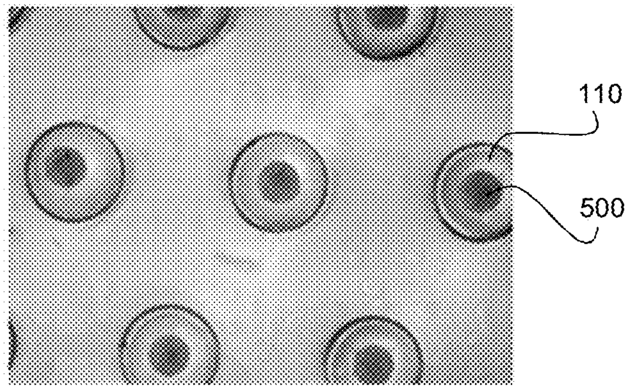
FIG. 10A shows HT29 cellular spheroids inside the microwells of a micropatterned T25 spheroid forming flask, as shown in FIG. 9.
Figure 10B:
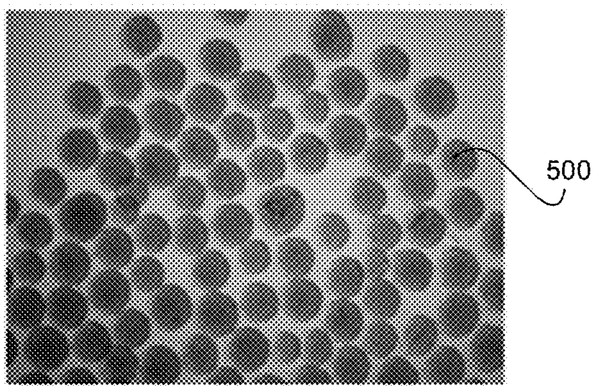
FIG. 10B shows harvested spheroids from a micropatterned T25 spheroid forming flask.
Figure 11A:
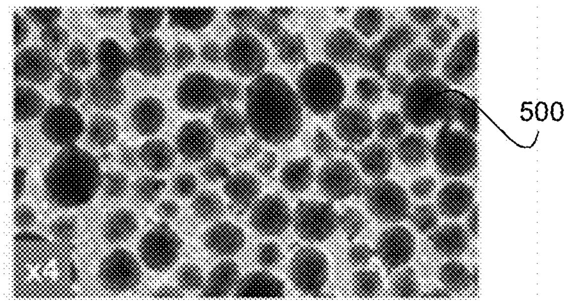
FIG. 11A and FIG. 11B show micrographs of spheroids or 3D aggregates formed on a NUNCLON SPHERA™ low binding surface, available from Nunc/ThermoFisher.
Figure 11B:
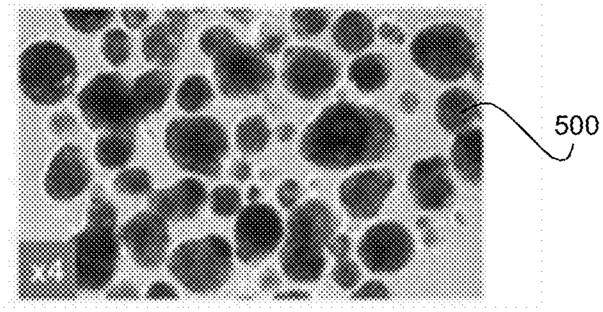

FIG. 10A shows HT29 cellular spheroids 500 inside the microwells 110 of a micropatterned T25 spheroid forming flask, as shown in FIG. 9. FIG. 10B shows harvested spheroids 500 from a micropatterned T25 spheroid forming flask, both according to Example 2 described below. FIG. 11A and FIG. 11B are micrographs illustrating the wide range size distribution of 3D aggregates (human ESC cells in FIG. 11A and mouse ESC in FIG. 11B) formed on a NUNCLON SPHERA™ low binding surface, available from Nunc. The NUNCLON SPHERA™ low binding surface has a low cell binding surface treatment, but lacks the geometry disclosed herein to allow for the formation of uniform spheroids.

Figure 12:
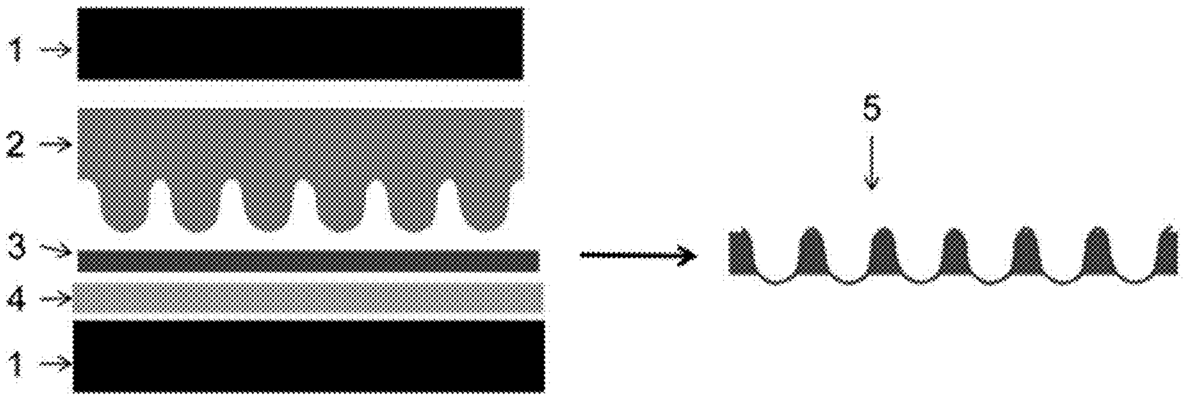
FIG. 12 is an illustration of a method of making a substrate having a multiwell array, according to embodiments.

FIG. 12 is an illustration of a method of making a multiwell array substrate, according to embodiments, and as described in Example 1 below. While FIG. 12 shows a hot embossing/thermoforming process, other methods of manufacturing microwell arrays according to embodiments are contemplated, including coining, injection molding, embossing and other methods known in the art.

FIGS. 13, FIG. 14A and FIG. 14B, and FIG. 15 are graphs comparing viable cell count (FIG. 13 and FIG. 14A) and cell productivity (FIG. 14B and FIG. 15) for substrates having arrays of microwells versus flat surfaces. The gas permeability of the wells may depend in part on the material of the substrate and the thickness of the substrate along the well. In embodiments, the thickness of the sidewalls and bottom of wells in a substrate having a microarray of wells may be constant and may be relatively thin. Or in embodiments, the walls of the wells in an array of microwells may be relatively thicker proximate to the opening into the well, and relatively thinner at the bottom of the well. Or, in embodiments, walls of the wells in an array of microwells may be relatively thinner proximate to the opening into the well, and relatively thicker at the bottom of the well. Depending on the material used and the thickness employed, substrates having an array of microwells may be gas permeable for purposes of the present disclosure.

Figure 15:
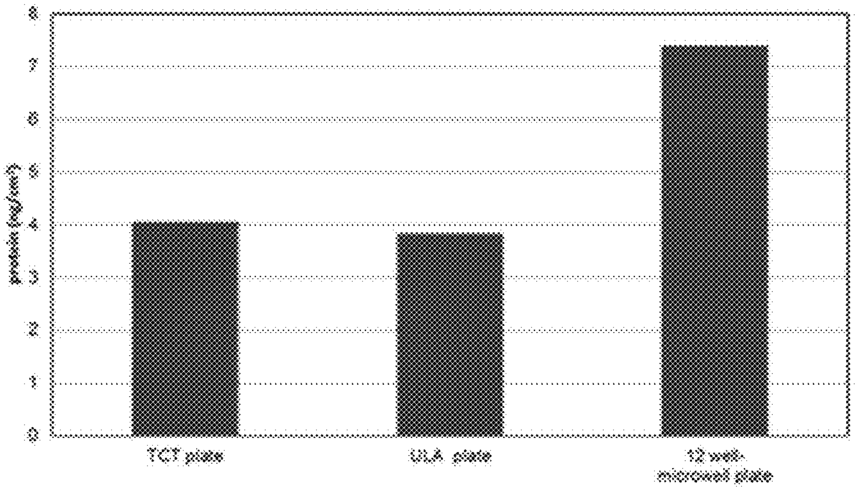
FIG. 15 shows a graph depicting total protein titer excreted from MH677 cells cultured on substrates having arrays of microwells versus flat surface.

FIG. 15 shows a graph depicting total protein titer excreted from MH677 cells cultured on substrates having arrays of microwells versus flat surface. These data are discussed below in Example 2.

While the apparatus depicted in FIG. 8 may be a hard-sided flask or a soft-sided cell culture flask, it will be understood that any other cell culture apparatus that includes a structured microwell array that has a surface that defines an exterior surface of the cell culture apparatus or that is in gaseous communication with an exterior of the apparatus may have a substrate having an array of microwells formed from gas permeable material as described herein.

A structured surface of a cell culture apparatus having an array of microwells as described herein may define any suitable number of wells that may have any suitable size or shape. The wells define a volume based on their size and shape. In many embodiments, one or more or all of the wells are symmetric and/or symmetrically rotatable around a longitudinal axis. In some embodiments, the longitudinal axes of one or more or all of the wells are parallel with one another. The wells may be uniformly or non-uniformly spaced. In some embodiments, the wells are uniformly spaced. One or more or all the wells can have the same size and shape or can have different sizes and shapes.

In some embodiments, the thickness and shape of the substrate around the well is configured to correct for refraction of light passing into the interior surface and out of the exterior surface. In some embodiments, the correction is achieved by adjusting the thickness of the substrate material forming the well. In some embodiments, the thickness of the substrate material proximate to the well-bottom (or nadir) is greater than the thickness of the substrate material in the sidewalls and/or proximate to the top aperture. In some embodiments, the thickness of the substrate material gradually decreases from a maximum at the nadir of the well-bottom to a minimum at the top aperture. For example, the shape and thickness may be as described in commonly-assigned U.S. provisional patent application No. 62/072,019, which provisional patent application is hereby incorporated herein by reference in its entirety to the extent that it does not conflict with the present disclosure.

The combination of, for example, non-adherent wells, spheroid inducing well geometry, and gravity can define a confinement volume in which growth of cells cultured in the wells is limited, which results in the formation of spheroids having dimensions defined by the confinement volume.

In some embodiments, the inner surface of the wells 2115 is non-adherent to cells. The wells may be formed from non-adherent material or may be coated with non-adherent material to form a non-adherent well. Examples of non-adherent material include perfluorinated polymers, olefins, or like polymers or mixtures thereof. Other examples include agarose, non-ionic hydrogels such as polyacrylamides, polyethers such as polyethylene oxide and polyols such as polyvinyl alcohol, or like materials or mixtures thereof. The combination of, for example, non-adherent wells, well geometry, and gravity can induce cells cultured in the wells to self-assembly into spheroids. Some spheroids can maintain differentiated cell function indicative of a more in vivo like response relative to cells grown in a monolayer.

In some embodiments, one or more wells have a concave surface, such as a hemi-spherical surface, a conical surface having a rounded bottom, and the like surface geometries or a combination thereof. The well and well bottom can ultimately terminate, end, or bottom-out in a spheroid conducive rounded or curved surface, such as a dimple, a pit, and like concave frusto-conical relief surfaces, or combinations thereof. Other shapes and construction of gas-permeable spheroid-conducive wells are described in commonly-assigned U.S. patent application Ser. No. 14/087,906, which application is hereby incorporated herein by reference in its entirety to the extent that it does not conflict with the present disclosure.

In some embodiments, well bottoms are flat or come to a point. Well bottoms may have any other suitable shape or dimension.

In some embodiments, the wells 115 described herein have a diametric dimension w in a range from about 200 micrometers to about 500 micrometers, e.g., 200, 250, 300, 350, 400, 450 or 500 micrometers, including ranges between any two of the foregoing values. Such diametric dimensions can control the size of a spheroid grown therein such that cells at the interior of the spheroid are maintained in a healthy state. In some embodiments, the wells 115 have a height H in a range from about 100 micrometers to about 500 micrometers, e.g., 100, 150, 200, 250, 300, 350, 400, 450 or 500 micrometers, including ranges between any two of the foregoing values. Of course, other suitable dimensions may also be employed.

Figure 16:
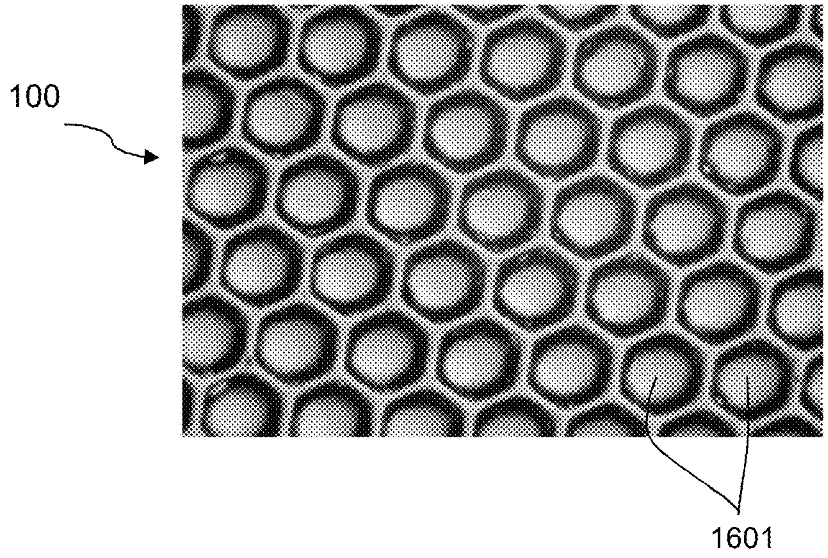
FIG. 16 is an image of an embodiment of a structured surface.
Figure 17:
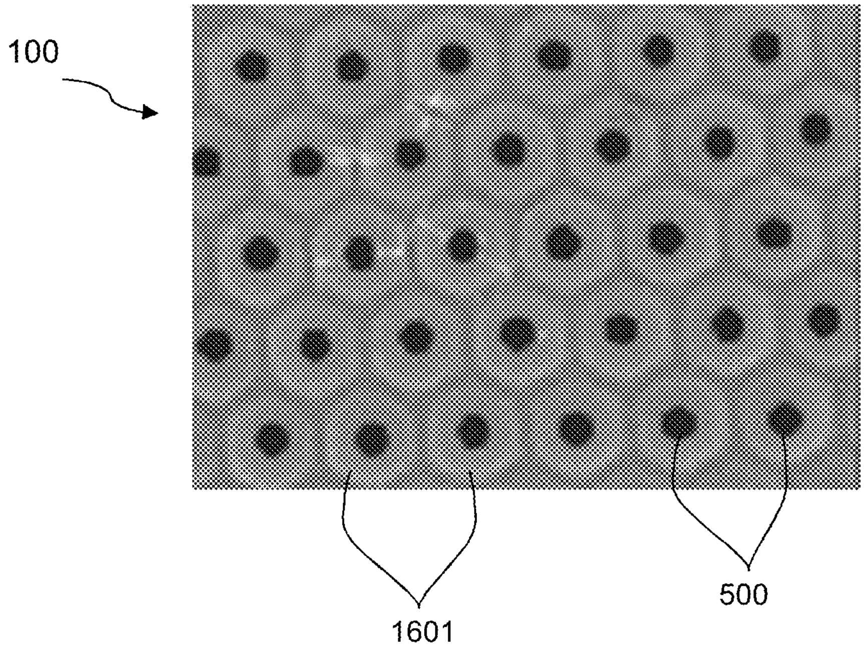
FIG. 17 is a photograph of cells grown in wells of an embodiment of a structured surface.

In some embodiments, the structured surface defining the wells includes an array of hexagonal close-packed well structures. An image of an embodiment of such a substrate having an array of hexagonal microwells 100 is shown in FIG. 16, showing the substrate having an array of hexagonal wells 1601. FIG. 17 is a schematic drawing showing cells (spheroids) 500 grown in wells 1601 of an embodiment of a substrate having an array of microwells 100 having a hexagonal close-packed well structure. In some embodiments, the cells within each well 1601 form a single spheroid 500, as depicted.

Figure 18:
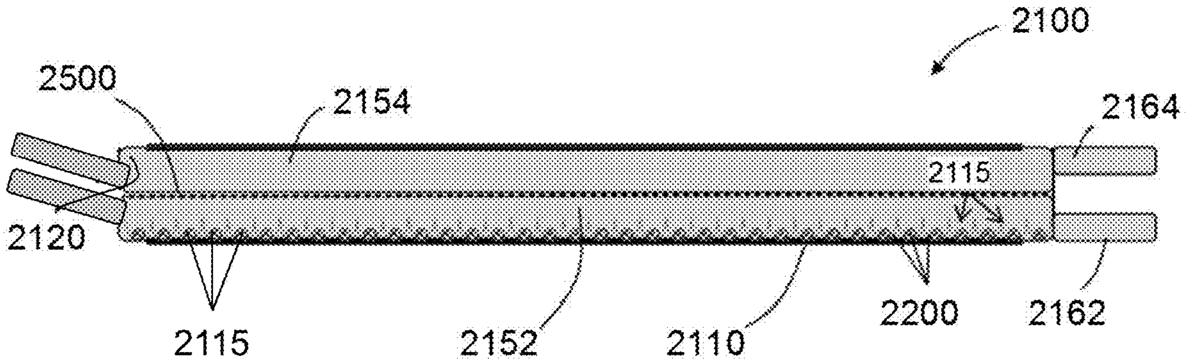
FIG. 18 is a side view illustrating an embodiment of a cell culture apparatus including a porous membrane support.
Figure 19:
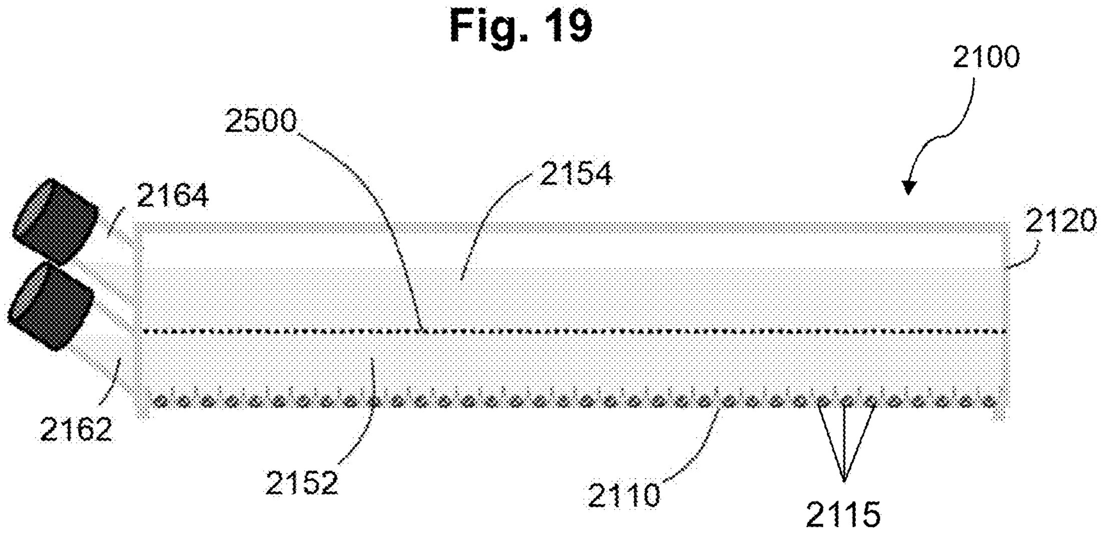
FIG. 19 is a side view illustrating an additional embodiment of a cell culture apparatus including a porous membrane support.
Figure 20:
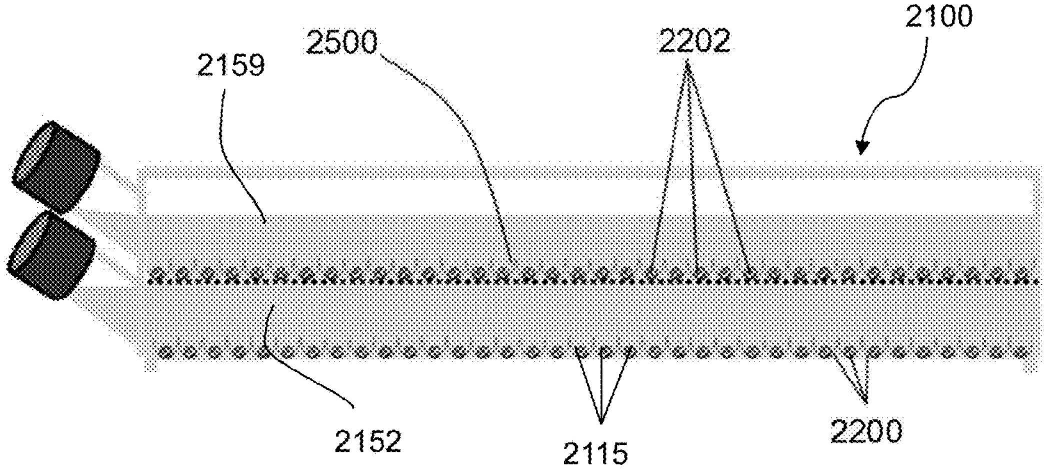
FIG. 20 is a side view illustrating an additional embodiment of a cell culture apparatus including a porous membrane support illustrating co-culture of cells.

FIG. 18 is a side view illustrating an embodiment of a cell culture apparatus including a porous membrane support. Various embodiments of cell culture apparatuses 2100 incorporating a porous membrane support 2500 are depicted in FIG. 18, FIG. 19 and FIG. 20. The porous membrane support 2500 is disposed across the housing to the apparatus (e.g., coupled to one or more sidewalls 2120) to compartmentalize the interior of the housing into separate culture chambers 2152 and 2154. A first culture chamber 2152 includes the substrate forming the structured surface defining gas permeable wells 2200 in gaseous communication with an exterior of the apparatus. The top of chamber 2152 is defined by porous membrane 2500. The bottom of the second culture chamber 2154 is defined by porous membrane 2500. Accordingly, a first population of cells 2200 can be cultured in the first chamber 2152 in wells 2115 of the structured surface formed by substrate 2110, and a second population of cells 2202 can be cultured in second chamber 2154 on porous membrane 2500.

The apparatuses depicted in FIG. 18, FIG. 19 and FIG. 20 include a first port 2162 in communication with the first chamber 2152 and a second port 2164 in communication with the second chamber 2154. In additional embodiments, the first chamber 2152 or the second chamber 2154 may optionally have an additional port (an exit port, not shown) to allow for flow of liquid through the chambers. The ports 2162, 2164 may be ports similar to ports (e.g., ports 2160) depicted in, and discussed with regard to, for example, FIG. 21, FIG. 22 and FIG. 23 below. Ports 2162, 2164 can be on the same side of the apparatus 2100, as depicted, can be on opposing sides, or can be oriented in any other suitable manner for providing separate access to the chambers or flow through the chambers 2152, 2154.

In FIG. 18, the apparatus is depicted as being operated with no headspace (filled to capacity with cell culture medium). In FIG. 19 and FIG. 20, the apparatuses are depicted as being operated with headspace (not filled to capacity with culture medium). Due to the porous nature of support 2500, chamber 2152 remains filled with culture medium while chamber 2154 can be operated with or without headspace. Due to the gas permeable nature of the wells 2115, height of medium above the cells 2200 may not be of a significant concern, e.g., as discussed above. However, if the housing is not otherwise gas permeable, it may be desirable to limit the height of medium above cells cultured on porous membrane support 2500. As depicted in FIG. 20, the porous membrane support 2500 can form a substrate having an array of microwells, e.g., as described above.

According to the embodiments shown in FIG. 18, FIG. 19 and FIG. 20, co-culture of more than one population of cells is contemplated. For example, a first population of cells may reside in the first chamber 2152 while a second population of cells may reside in the second chamber 2154. These populations of cells may be separated by a permeable membrane 2500. This allows for chemical communication between a first population of cells and a second population of cells. In embodiments one or both of these populations of cells may be spheroids. For example, as shown in FIG. 20, a first population of spheroid cells 2200 may grow in the first chamber 2152, forming spheroids due to the spheroid inducing geometry of the cell culture substrate, while a second population of spheroid cells 2202, also forming spheroids due to the spheroid inducing geometry of the cell culture substrate present in the second cell culture chamber, may grow in the second chamber 2154. Through the porous membrane 2500, the second population of spheroid cells 2202 is in chemical communication with the first population of spheroid cells 2200. In this way, it is possible to co-culture two separate populations of spheroid cells, while allowing the two separate populations of spheroid cells to be in chemical communication with each other. Or, in embodiments, as shown in FIG. 18, a first population of cells may be spheroid cells growing in a first cell culture chamber 2152 and a second population of cells that are not spheroid cells (because the second cell culture chamber does not have spheroid inducing geometry) may grow in a second cell culture chamber 2154, while the presence of a porous membrane 2500 allows the first and second populations of cells to be in chemical communication with each other. As shown in FIG. 19, the second population of cells may be grown in the presence of a head space, or as shown in FIG. 18, the second population of cells may be grown in the absence of a head space. Similarly, a head space may be present or absent from the first cell culture chamber. Or, spheroid inducing geometry may be present or absent in the first cell culture chamber. Those of ordinary skill in the art will recognize that many combinations of these features may be desirable, depending upon the cell culture requirements of the user.

In some embodiments, the housing of an apparatus is gas-permeable. By way of example a gas-permeable film or bag may form at least a portion of the housing.

In some embodiments, one or more of the wells are configured, based at least in part upon their defined size and shape, to grow a single spheroid of a defined size. Spheroids may expand to size limits imposed by the geometry of the wells in which they are cultured. For example, each well may include a microwell or cell culture volume that allows the spheroid to grow to a certain diameter. In other words, the geometrical dimensions of the microwell or cell culture volume may constrain the spheroid growth such that the spheroid diameter reaches a maximum value and stays at that maximum value. The production of consistently sized spheroids may lead to tissue-like, non-expanding spheroids that may be ideal for improving reproducibility of assay results. The production of consistent spheroids may be the result of a variety of shaped and dimensioned volumes (e.g., a microwell or cell culture volume) defined by the interior of the one or more wells. For example, the microwell or cell culture volume may have a diametric dimension in a range from about 100 micrometers to about 700 micrometers, such as from about 200 micrometers to 500 micrometers or any range within the aforementioned values (e.g., from 100 micrometers to 200 micrometers, from 100 micrometers to 500 micrometers, or from 200 micrometers to 700 micrometers). The microwell or cell culture volume may have a depth in a range from about 50 micrometers to about 700 micrometers, such as about 100 micrometers to 500 micrometers, or any range within the aforementioned values.

FIG. 19 is a side view illustrating an additional embodiment of a cell culture apparatus including a porous membrane support.

FIG. 20 is a side view illustrating an additional embodiment of a cell culture apparatus including a porous membrane support illustrating co-culture of cells.

Figure 21:
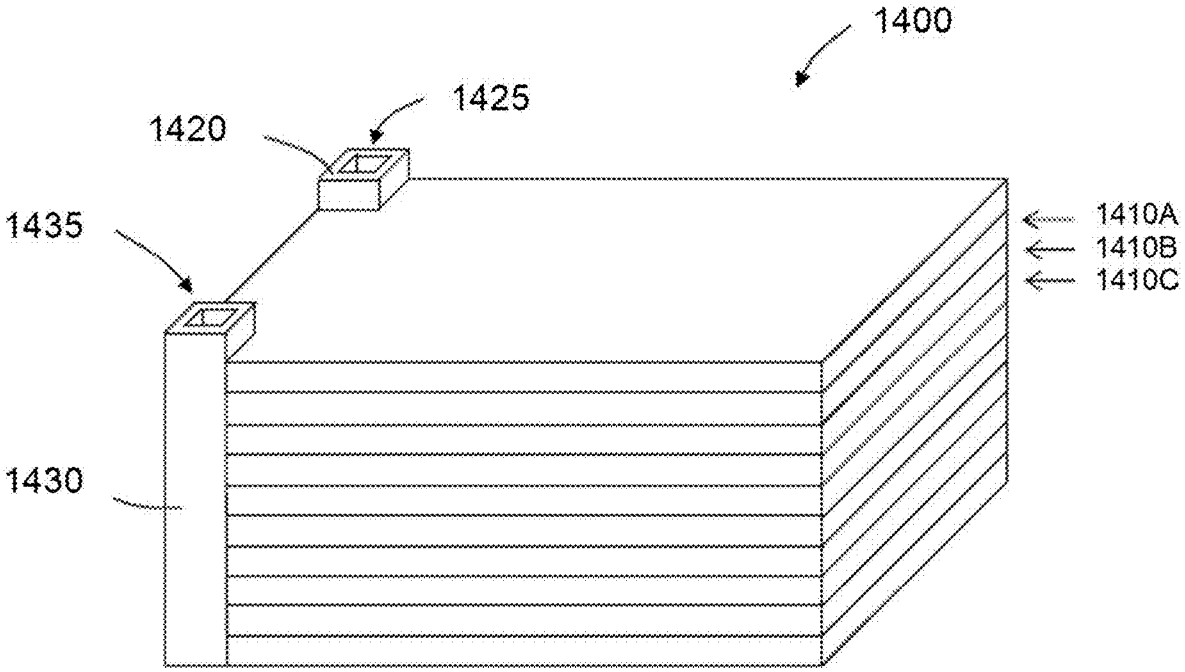
FIG. 21 is a schematic perspective view of an embodiment of a cell culture apparatus.

With reference to FIG. 21, an embodiment of cell culture apparatus 1400 having a plurality of stacked cell culture compartments 1410A, 1410B, 1410C is shown. Each cell culture compartment can include a substrate having an array of microwells as described herein. Apparatus 1400 includes a fill manifold 1430 having an opening 1435 through which cell culture media can be introduced or removed. Fill manifold 1430 includes a plurality of apertures (not shown). Each cell culture compartment 1410A, 1410B, 1410C has at least one aperture (not shown) in fluid communication with an aperture of manifold 1430 such that cell culture media introduced through opening 1435 can flow into cell culture compartments 1410A, 1410B, 1410C. Opening 1435 can be covered with a cap (not shown) or the like when apparatus 1400 is oriented in a cell culture position. Apparatus 1400 also optionally includes a vent manifold 1420 defining an opening 1425 through which air, metabolic gases, and the like can flow. Vent manifold 1420 includes a plurality of apertures (not shown). Each cell culture compartment 1410A, 1410B, 1410C has at least one aperture (not shown) in gaseous communication with an aperture of manifold 1420 such that cell culture metabolic gases can be exchanged between an interior of a cell culture chamber and an exterior of the apparatus 1400 via opening 1425. Opening 1425 can be covered with a vented cap (not shown), filter (not shown) or the like when apparatus 1400 is oriented in a cell culture position.

Figure 22:
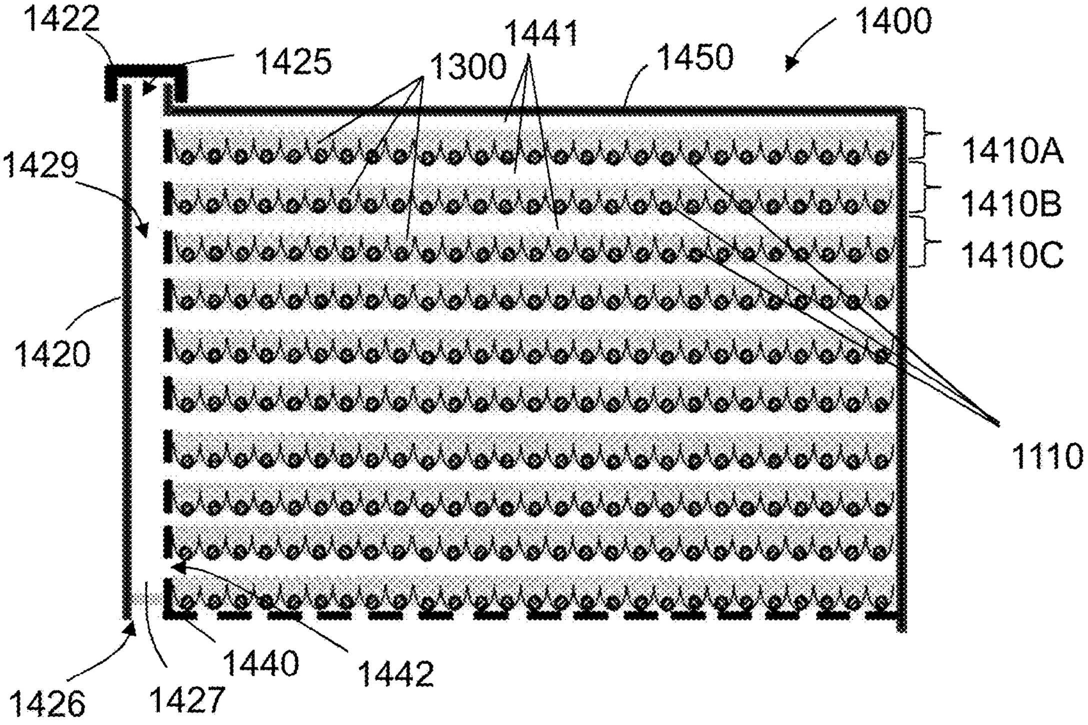
FIG. 22 is a schematic cross-sectional view of an embodiment of a cell culture apparatus.

Referring now to FIG. 22, a cross-sectional view of a cell culture apparatus 1400, which can be a type of apparatus depicted in FIG. 21, is shown. Apparatus 1400 has a plurality of stacked cell culture compartments 1410A, 1410B, 1410C, each having a substrate 1110 defining a structured surface having an array of gas permeable wells as described above. In the embodiment depicted in FIG. 22, each compartment (e.g., 1410B, 1410C), except for the top-most compartment 1410A in the stack, has a top surface 1450 defined by an second major surface of the structured of substrate 1110 of an adjacent compartment. For example, second major surface of substrate 1110 of compartment 1410B serves as the top interior surface of compartment 1410C. Accordingly, the interiors of adjacent compartments are in gaseous communication with each other through the common substrate 1110 that forms the bottom structured surface/top surface. The top-most compartment 1410 has a top inner surface formed by top 1450, which can be a plate.

The interiors of the compartments (e.g., compartments 1410A, 1410B, 1410C) are defined by a substrate having an array of microwells (e.g., array 100 depicted in FIG. 9 a top surface defined by exterior second major surface of the substrate of the compartment above, and one or more sidewalls 1440. The one or more side wall 1440 has an vent aperture 1442 in communication with a vent column 1429 defined by manifold 1420, which is in communication with an exterior of the apparatus via one or more openings 1425, 1426 defined by manifold 1420. Vent aperture 1442 defines a maximum volume of cell culture medium 1300 that can be present in the interior of a cell culture chamber when the apparatus is a cell culture orientation (e.g., as depicted in FIG. 22). The volume of cell culture medium in the compartment can be less than the maximum. Vent aperture 1442 also defines a minimum headspace volume in the interior of a cell culture compartment. The volume of headspace in the interior of the compartment can be greater than the minimum headspace volume (if the cell culture medium volume is less than the maximum medium volume).

Accordingly, cells cultured in wells of a structured surface defined by substrate 1110 of a chamber (e.g., chamber 1410B) above an adjacent chamber (e.g., chamber 1410C) are in gaseous communication with the headspace 1441 of the adjacent chamber (e.g., chamber 1410C) via the gas permeable wells. Headspace 1441 is in communication column 1429 defined by manifold, which is in communication with an exterior of the apparatus via one or more openings 1425, 1426.

An optional filter 1427 can be incorporated into the opening 1425, opening 1425, or in cap 1422 to vent metabolic gases. Having a vent on the bottom of the apparatus can be advantageous in some embodiments. For example, the metabolic waste gas carbon dioxide is more dense than atmospheric air and tends to form a gradient with highest concentrations on the bottom in culture apparatuses that do not have a bottom vent. Accordingly, the presence of a vent on the bottom of the apparatus (e.g., formed by vent column 1429 and opening 1426) can facilitate transfer of waste carbon dioxide out of the apparatus.

Figure 23:
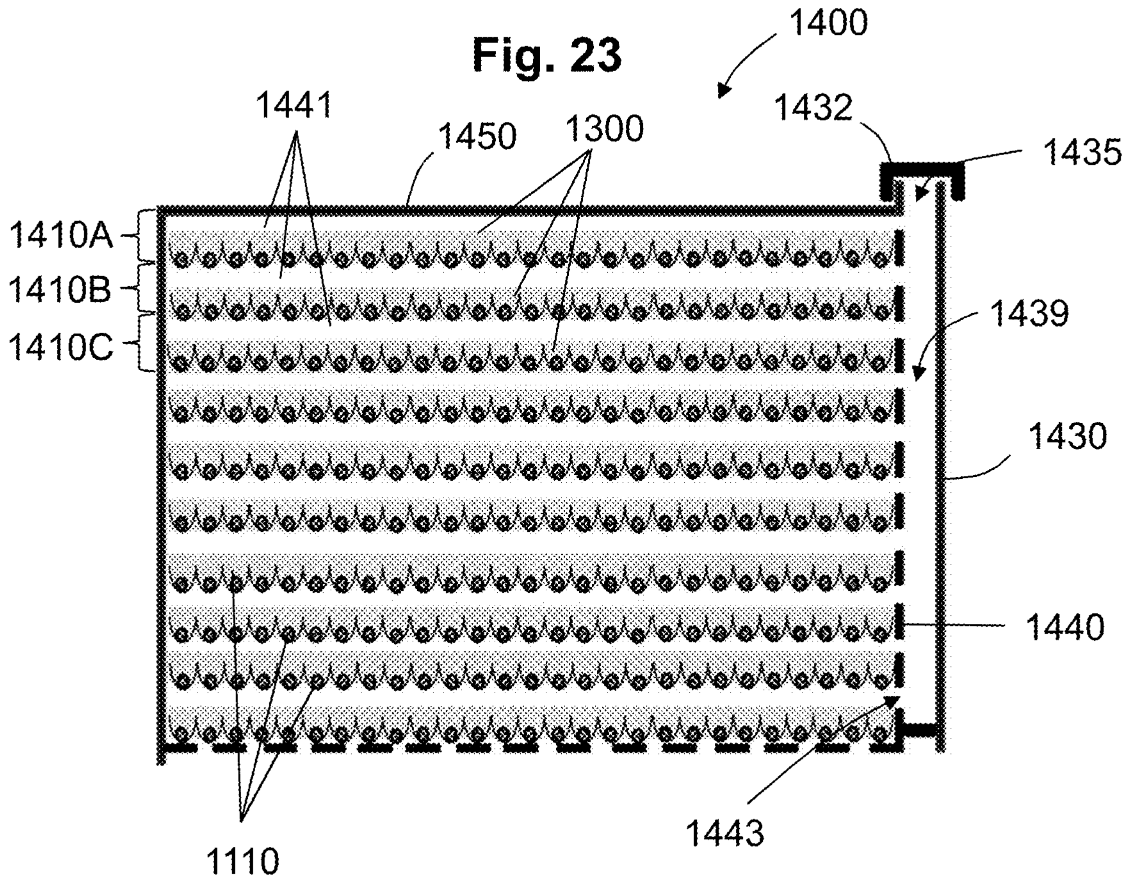
FIG. 23 is a schematic cross-sectional view of an embodiment of a cell culture apparatus.

Referring now to FIG. 23, a cross-sectional view of a cell culture apparatus 1400, which can be a type of apparatus depicted in FIG. 21 and may be a portion of the apparatus depicted in FIG. 22, is shown. To the extent that each reference numeral in FIG. 23 is not explicitly discussed, reference is made to the discussion of like numbered components described above with regard to FIG. 22. In the illustrated embodiment, interiors of the compartments (e.g., compartments 1410A, 1410B, 1410C) are defined by an interior structured surface of substrate 1110, a top surface defined by an exterior surface of the substrate of the compartment above, and one or more sidewalls 1440. The one or more side walls 1440 have an aperture 1443 in communication with column 1439 defined by fill manifold 1430, which is in communication with an exterior of the apparatus via opening 1435 defined by manifold 1430, which may be covered by a cap 1432 when the apparatus is in a cell culture orientation. Cell culture medium 1300 can be introduced into cell culture compartments (e.g., compartments 1410A, 1410B, 1410C) or removed from cell culture compartments via column 1439 and opening 1435 via manipulation of the apparatus.

Figure 24A:
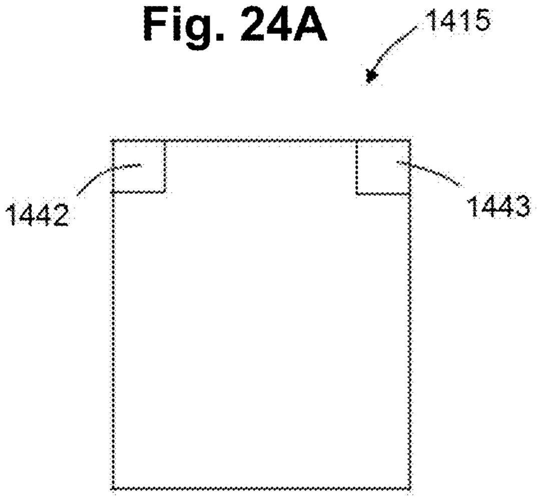
FIG. 24A is a schematic bottom view of an embodiment of a tray that can be used to form a part of an apparatus as depicted in any of FIGS. 21, 22 and 23.
Figure 24B:
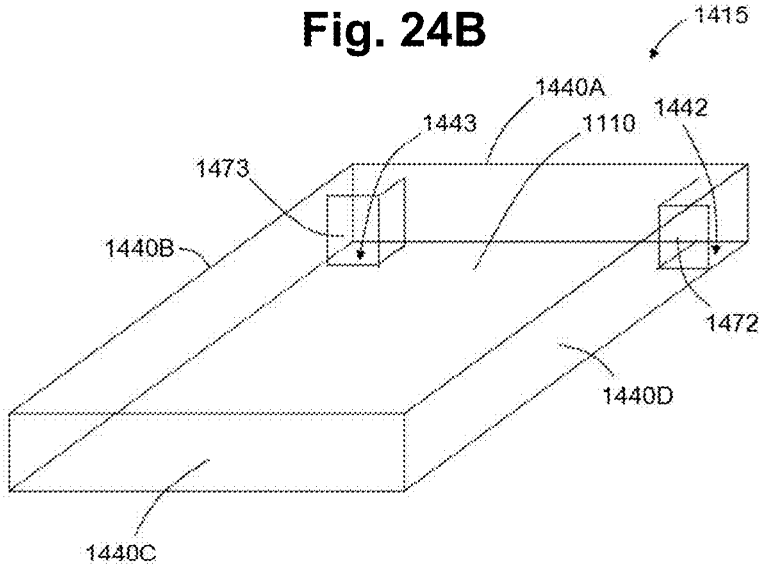
FIG. 24B is a schematic perspective view of an embodiment of the tray shown in FIG. 24A.

Referring now to FIGS. 24A and 24B, a schematic bottom view (FIG. 24A) and a schematic perspective view (FIG. 24B) are shown of a tray 1415 that can serve to form cell culture compartments (e.g., compartments 1410A, 1410B, 1410C as depicted in FIG. 21, FIG. 22 and FIG. 23) when a plurality of such trays are stacked on top of one another. The tray 1415 includes sidewalls 1440A, 1440B, 1440C, 1440D that extend from a substrate 1110 defining a substrate having an array of microwells. In some embodiments, tray includes a single enclosing sidewall (not shown). A partial height wall 1472 is coupled to sidewall 1440A and sidewall 1440D. Partial height wall 1472 and sidewalls 1440A, 1440D surround and define vent aperture 1442. When a cell culture apparatus is assembled from stacked trays, metabolic gases within an interior of a chamber formed by tray 1415 can flow over partial wall 1472 and through aperture 1442. Vent apertures 1442, partial walls 1472 and associated sidewalls of stacked trays 1415 can form at least a portion of a vent column (e.g., vent column 1429 depicted in FIG. 22).

Tray 1415 also includes a partial height wall 1473 coupled to sidewall 1440A and to sidewall 1440B. Partial height wall 1473 and sidewalls 1440A, 1440B surround and define fill aperture 1443. When a cell culture apparatus is assembled from stacked trays, culture media can be introduced to or removed from an interior of a chamber formed by tray 1415 over partial wall 1473 and through fill aperture 1443 via manipulation of the assembled apparatus. Fill apertures 1443, partial walls 1473 and associated sidewalls of stacked trays 1415 can form at least a portion of a fill column (e.g., fill column 1439 depicted in FIG. 23).

The height of partial wall 1473 defines a maximum height and volume of cell culture medium that can be contained within a cell culture compartment formed by tray 1415. The top of the partial wall 1473 can be any suitable distance from the substrate 1110 forming the structured surface. In some embodiments, the distance is 5 mm or greater, such as 6, 7, 8, 9, 10, 12, 15, or 20 mm, including ranges between any two of the foregoing. Because of the gas permeable wells of the structured surfaces of cell culture apparatuses assembled from such trays are in communication with an exterior of the apparatus, the height of the cell culture medium above the cells can be greater than available with conventional cell culture apparatuses in which gas exchange occurs primarily through the cell culture medium.

The distance from the top of partial wall 1472 to the substrate 1110 can be the same or greater than the distance from the top of partial wall 1473 to the substrate 1110. Accordingly, if the compartment is overfilled with culture medium, excess medium will drain through fill aperture 1443 rather than vent aperture 1442. In embodiments employing a bottom filter (such as filter 1427 in FIG. 22) in a vent column, the bottom filter will not be contaminated with medium. Of course, proper manipulation of an assembled apparatus should also prevent the bottom filter from being contaminated with medium.

Figure 25:
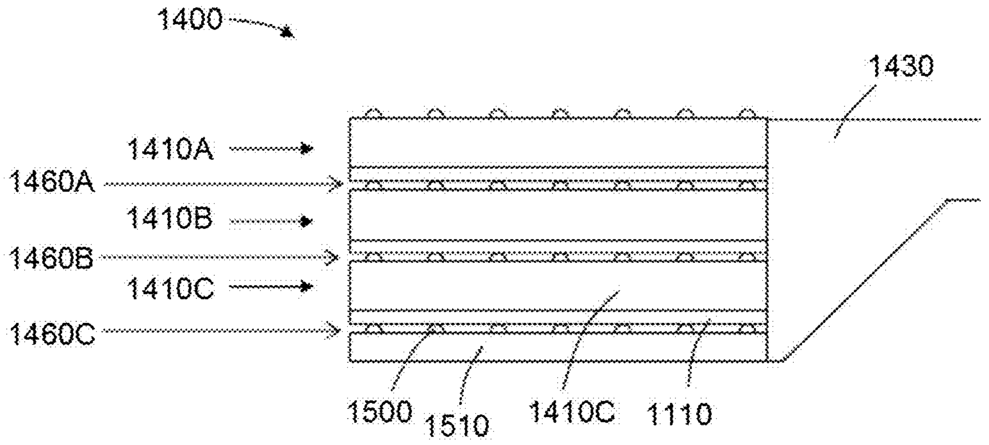
FIG. 25 is a schematic side view of an embodiment of a cell culture apparatus.

Referring now to FIG. 25, a schematic side view of an embodiment of a cell culture apparatus 1400 having a plurality of stacked cell culture compartments 1410A, 1410B, 1410C is shown. Each compartment can include a substrate 1110 defining a structured surface as described above. Apparatus 1400 includes spacers 1500 positioned adjacent the substrate 1110 forming the structured surface and, exterior to the chamber, providing a passageway for air flow, which passage way is referred to herein as a "tracheal space" (e.g., tracheal spaces 1460A, 1460B, 1460C). Because the structured surface defines gas permeable wells in which cells can be cultured, metabolic gases may be exchanged through the wells to a tracheal space 1460A, 1460B, 1460C defined by spacers 1500 to an exterior of the apparatus 1400. Apparatus 1400 also includes a manifold 1430 defining an opening through which cell culture media can be introduced or removed. Manifold 1430 includes a plurality of apertures (not shown). Each cell culture compartment 1410A, 1410B, 1410C has at least one aperture (not shown) in fluid communication with an aperture of manifold 1430 such that cell culture media introduced through manifold 1430 can flow into cell culture compartments 1410A, 1410B, 1410C.

The bottom of the cell culture apparatus 1400 in FIG. 25 includes a plate 1510 on which spacers 1500 are disposed. In embodiments, the plate 1510 and spacers 1500 are a singled part, such as a molded part. Such a plate may form the top surface of the other cell culture compartments (e.g., compartments 1410A, 1410B, 1410C). For each compartment, one or more sidewall 1440 extends from the substrate 1100 defining the structured surface to the top surface, which may be formed of a plate with spacers. Aperture (not shown) in communication with an aperture (not shown) of port 1430 can be defined by a sidewall.

Stacked cell culture trays or chamber can be assembled in any suitable manner. For example such components can be joined using welding techniques (e.g., thermal, laser, long IR or ultrasonic welding, or the like), adhering, solvent-bonding or the like In some embodiments, the structured surface is coupled to a bag. Bags suitable for cell culture can be formed from films by heat sealing, laser welding, application of adhesive, or any other method known in the art of inflatable bag making. Walls or portions thereof of a bag may have a thickness that allows for efficient transfer of gas across the wall. It will be understood that desired thickness may vary depending on the material from which the wall is formed. By way of example, the wall or film forming the wall may be between about 0.02 millimeters and 0.8 millimeters thick. A bag may be made of any material suitable for culturing cells. In various embodiments, the bag is formed of optically transparent material to allow visual inspection of cells cultured in the bag. Examples of optically transparent, gas permeable materials that may be used to form the bag include polystyrene, polycarbonate, poly(ethylene vinyl acetate), polysulfone, polymethylpentene, polytetrafluoroethylene (PTFE) or compatible fluoropolymer, a silicone rubber or copolymer, poly(styrene-butadiene-styrene), or polyolefin, such as polyethylene or polypropylene, or combinations of these materials.

The cell culture apparatuses described herein can be used to culture cells within wells of a structured surface. As described above, the cell culture medium in an apparatus can be any suitable height above the cells. In some embodiments, the height of the cell culture medium in the apparatus above the cells (e.g., above the top or the nadir of the wells is about 5 mm or greater. In some embodiments, the height of the cell culture medium in the apparatus above the cells (e.g., above the top or the nadir of the wells is about 6 mm or greater, about 7 mm or greater, about 8 mm or greater, about 9 mm or greater or about 10 mm or greater.

Because of the gas permeability of the wells, such heights of cell culture medium can be used to maintain the cells in a healthy state. Accordingly, cells cultured in the apparatuses described herein can be cultured for extended periods of time with such heights of cell culture medium. For example, the cells can be continuously cultured with such media heights for 24 hour or longer, for 48 hours or longer, for 72 hours or longer, for 96 hours or longer, or until the medium is exchanged.

In embodiments where the wells are non-adherent to cells, the cells may be harvested by inverting the apparatus to allow gravity to displace the cells from the wells.

In some embodiments, a porous membrane is disposed in a cell culture apparatus as described herein to support growth of a second cell-type within the same apparatus, but separated from a first cell type cultured on the structured surface in gaseous communication with the exterior of the apparatus (or to support growth of additional cells of the same type). In some embodiments, stem cells are cultured on the structure surface having the gas permeable wells in communication with an exterior of the apparatus and feeder cells are cultured on the porous membrane. Of course, any other desired combination of cells and compartmentalization can be employed using such an apparatus.

The porous membrane can be disposed within a housing of a cell culture apparatus to compartmentalize the housing into two growth chambers. Preferably the permeable membrane limits cell movement through the membrane but permits passage of biomolecules. Examples of materials that can be used to form a porous membrane include track-etched membranes or woven or non-woven porous materials. The material of the porous membrane may be treated or coated to make it more adherent or more non-adherent to cells. Treatment may be accomplished by any number of methods known in the art which include plasma discharge, corona discharge, gas plasma discharge, ion bombardment, ionizing radiation, and high intensity UV light. Coatings can be introduced by any suitable method known in the art including printing, spraying, condensation, radiant energy, ionization techniques or dipping. The coatings may then provide either covalent or non-covalent attachment sites. Such sites can be used to attach moieties, such as cell culture components (e.g., proteins that facilitate growth or adhesion). Further, the coatings may also be used to enhance the attachment of cells (e.g., polylysine). Alternatively, cell non-adherent coatings as described above can be used to prevent or inhibit cell binding. In some embodiments, the porous membrane can be fabricated to have a structured surface having a plurality of wells, such as described above with regard to the substrate forming the structured surface defining the plurality of gas permeable wells. However, in this case, the porous membrane material is formed to have the structured surface.

The gas permeable wells of the structured surface (e.g., as described above) permits control of oxygen tension by regulating gas concentration in an incubator where the apparatus is placed to permit cell growth. The permeable membrane support provides a method to physically separate different cell populations while permitting transfer of biologically active components.

The porous membrane may be attached to housing (e.g., sidewalls, etc.) of the apparatus in any suitable manner. For example, the porous membrane can be incorporated into the device in a similar manner to incorporation of the substrate forming the substrate defining the structured surface having the plurality of gas permeable wells, as described above.

Figure 26:
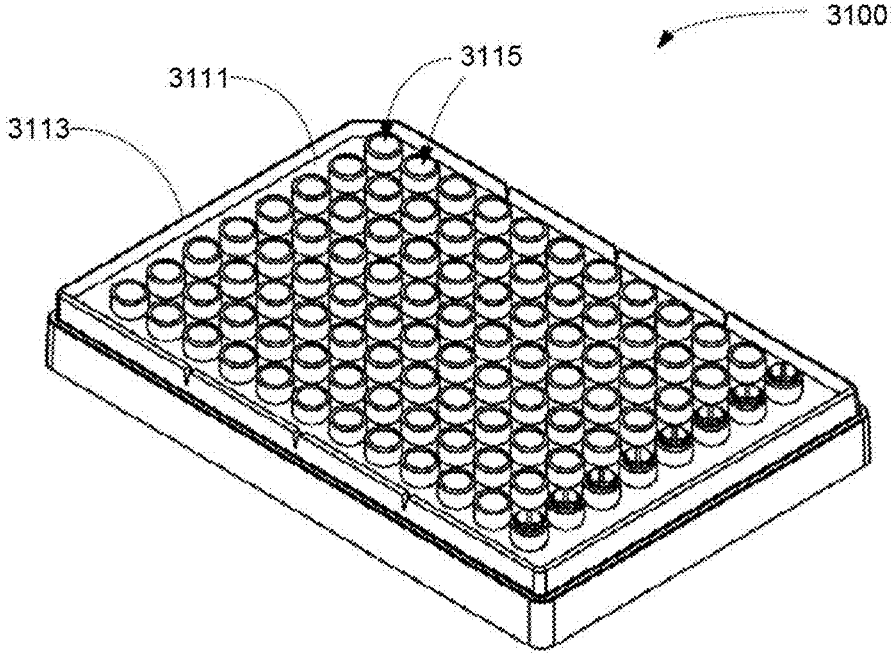
FIG. 26 is a perspective view of an embodiment of a cell culture apparatus having wells.

In the embodiment depicted in FIG. 26, the cell culture apparatus 3100 is a 96-well multiwell plate having wells 3115 in a plate 3111 surrounded by a frame 3113. However, as discussed above, a cell culture apparatus can have any suitable number of wells (for example, 3, 6, 12, 96, or any other number of wells may be provided). In the depicted embodiment, at least a portion of each of the plurality of wells 3115 contains a substrate having an array of microwells and provides a position to form spheroids, as described above. Nearly any type of cell culture apparatus having a well that is used to culture cells may be designed by employing a substrate having an array of microwells which can, in some embodiments, form the entire volume of the well or can, in some embodiments, form a cell culturing sub-volume of the well. In some embodiments, the cell culture apparatuses with which the microwell design may be implemented may be a multi-well plate, for example, a 96-well multiwell plate, a 384-well multiwell plate, a 1536-well multiwell plate, or the like. In some embodiments, at least a surface of the multiwell plate is gas-permeable.

The ability for the plurality of wells to allow cells to aggregate in such a way that spheroids form as well as the ability for the spheroids formed within each of the plurality of wells to maintain a consistent size across the plurality of wells can be accomplished in any suitable manner. For example, the plurality of wells 3115 may comprise an array of microwells structured and arranged like the microwells shown in FIG. 1A, FIG. 1B, FIG. 2A, FIG. 2B, FIG. 3A, FIG. 3B, FIG. 3C, FIG. 3D, FIG. 3E, FIG. 4A, FIG. 4B, FIG. 4C, FIG. 4D, FIG. 5A, FIG. 5B, FIG. 5C, FIG. 5D, FIG. 5E, or FIG. 16, in which cells grow as spheroids 500.

In some embodiments, one or more of the wells are configured, based at least in part upon their defined size and shape, to grow a single spheroid of a defined size. Spheroids may expand to size limits imposed by the geometry of the wells in which they are cultured. For example, each well may include a microwell or cell culture volume that allows the spheroid to grow to a certain diameter. In other words, the geometrical dimensions of the microwell or cell culture volume may constrain the spheroid growth such that the spheroid diameter reaches a maximum value and stays at that maximum value. The production of consistently sized spheroids may lead to tissue-like, non-expanding spheroids that may be ideal for improving reproducibility of assay results. The production of consistent spheroids may be the result of a variety of shaped and dimensioned volumes (e.g., a microwell or cell culture volume) defined by the interior of the one or more wells. For example, the microwell or cell culture volume may have a diametric dimension in a range from about 100 micrometers to about 700 micrometers, such as from about 200 micrometers to 500 micrometers or any range within the aforementioned values (e.g., from 100 micrometers to 200 micrometers, from 100 micrometers to 500 micrometers, or from 200 micrometers to 700 micrometers). The microwell or cell culture volume may have a depth in a range from about 50 micrometers to about 700 micrometers, such as about 100 micrometers to 500 micrometers, or any range within the aforementioned values.

Each of the plurality of wells described herein may assist cells deposited therein to form spheroids. Each of the plurality of wells may also limit or constrain a diameter of each of the spheroids to a value of about, e.g., less than or equal to 500 micrometers, less than or equal to 400 micrometers, less than or equal to 300 micrometers, less than or equal to 250 micrometers, less than or equal to 150 micrometers, etc. or any range within the aforementioned values (e.g., 150 to 250, 150 to 300, 150 to 400, 150 to 500, 250 to 300, 250 to 400, etc.). In some embodiments, each of the plurality of wells forms a spheroid defined by a diameter that differs from an average diameter of all the spheroids grown in the plurality of wells by about, e.g., less than or equal to 20%, less than or equal to 15%, less than or equal to 10%, less than or equal to 5%, less than or equal to 2%, etc. or any range within the aforementioned values.

Figure 29:
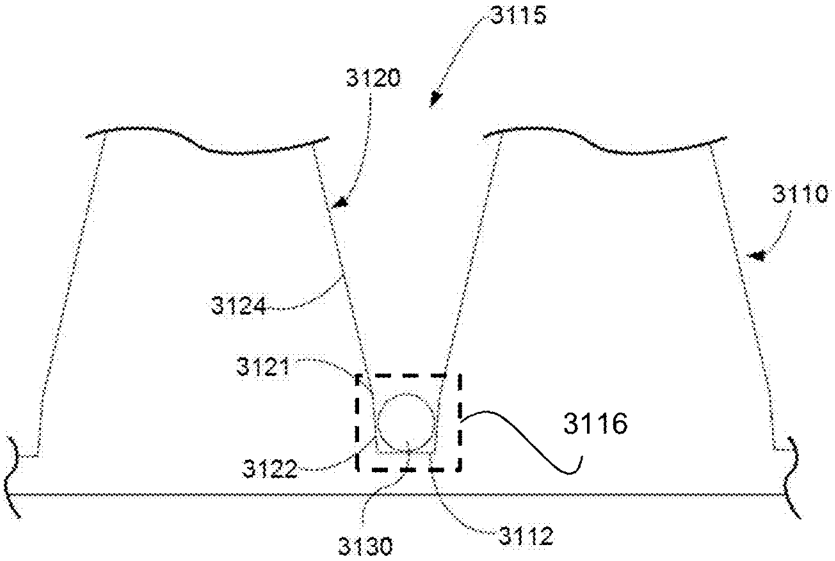
FIG. 29 is a magnified schematic cross-sectional view of an embodiment of a plurality of wells.

In embodiments shown in FIG. 27, FIG. 28 and FIG. 29, the array of microwells 3115 are formed in a substrate 3110. Each of the plurality of wells 3115 may have a top aperture 3118, a bottom surface 3112, and a sidewall surface 3120 extending from the top aperture 3118 to the bottom surface 3112. Additionally, the sidewall surface 3120 may define a pen tip area 3116 (see FIG. 29) between the top aperture 3118 and the bottom surface 3112, so named because the constricted area at the bottom of the well looks like the tip of a pen. The pen tip area is a spheroid-inducing geometry.

The top aperture 3118 of each of the plurality of wells 3115 may be used as an opening through which to seed cells into each of the plurality of wells 3115. The top aperture 3118 may have a variety of different shapes and sizes. For example, the top aperture 3118 may be defined by a shape that is circular, oval, square, rectangular, hexagonal, quadrilateral, etc. The top aperture 3118 may also be defined by a diametric dimension (e.g., diameter, width, etc., depending on shape). The diametric dimension of the top aperture 3118 may be defined as a distance across the top aperture at a widest point. The diametric dimension of the top aperture 3118 may be about, e.g., greater than or equal to 300 micrometers, greater than or equal to 500 micrometers, greater than or equal to 800 micrometers, greater than or equal to 1000 micrometers, greater than or equal to 1500 micrometers, greater than or equal to 2000 micrometers, etc. or, less than or equal to 7000 micrometers, less than or equal to 6000 micrometers, less than or equal to 4000 micrometers, less than or equal to 2500 micrometers, less than or equal to 1700 micrometers, less than or equal to 1200 micrometers, etc. or any range within the aforementioned values.

The bottom surface 3112 of each of the plurality of wells 3115 may be conducive to allowing cells to be cultured thereon or there-above. The bottom surface 3112 may have a variety of different shapes and sizes. For example, the bottom surface 3112 may be rounded, hemispherical, flat, conical, etc. By way of further example, the bottom surface 3112 may also be defined by a shape that is circular, oval, square, rectangular, hexagonal, quadrilateral, etc. As shown in FIGS. 27-29, the bottom surface 3112 is flat and is defined by a diametric dimension. The diametric dimension of the bottom surface may be about, e.g., greater than or equal to 0 micrometers, greater than or equal to 50 micrometers, greater than or equal to 75 micrometers, greater than or equal to 100 micrometers, greater than or equal to 200 micrometers, greater than or equal to 275 micrometers, etc. or, less than or equal to 700 micrometers, less than or equal to 500 micrometers, less than or equal to 400 micrometers, less than or equal to 300 micrometers, less than or equal to 250 micrometers, less than or equal to 150 micrometers, etc. or any range within the aforementioned values. For bottom surfaces 3112 that have a rounded bottom or similar surface (e.g., hemispherical, conical, etc.), with a nadir located at the lowest point, the diametric dimension of the bottom surface 112 is considered to be zero. In some embodiments, the diametric dimension of the top aperture 3118 is greater than the diametric dimension of the bottom surface 3112. In other embodiments, the diametric dimension of the top aperture 3118 is equal to the diametric dimension of the bottom surface 3112.

In some embodiments, the bottom surface 3112 of each of the plurality of wells 3115 may be uniformly constructed with the substrate having a microarray of wells (see also FIG. 29). In other embodiments, the bottom surface 3112 may be made from a material that is different from the material used to form substrate 3110. Various methods of manufacturing the plurality of wells will be described further below. The bottom surface 3112 or the sidewall surface 3120 may be gas permeable to help provide oxygen to the cells or spheroids 3130 cultured within the wells 3115. In some embodiments, the substrate 3150 that defines the bottom surface 3112 may be a gas permeable substrate. In some embodiments, the substrate 3150 may comprise a gas permeable film. The gas permeability of the bottom surface 3112 to an exterior will depend in part on the material of the bottom surface 3112 and the thickness of the bottom surface 3112. For example, the gas permeability of the wells may be as described in U.S. provisional patent application No. 62/072,088, filed on 29 Oct. 2014, and entitled "GAS PERMEABLE CULTURE FLASK," which provisional patent application is hereby incorporated herein by reference in its entirety to the extent that it does not conflict with the present disclosure.

The pen tip area 3116 (see FIG. 29) may be defined by the sidewall surface 3120 between the top aperture 3118 and the bottom surface 3112. A location of the pen tip area 3116 may be defined by other components of the well. For example, the pen tip area 3116 may be defined by a diametric dimension 3144 across the sidewall surface 3120. The diametric dimension 3144 of the pen tip area 3116 may be defined as a distance across the sidewall surface 3120 at the pen tip area 3116. The pen tip area 3116 may be defined by a diametric dimension 3144 of about, e.g., greater than or equal to 50 micrometers, greater than or equal to 100 micrometers, greater than or equal to 200 micrometers, greater than or equal to 300 micrometers, greater than or equal to 400 micrometers, greater than or equal to 550 micrometers, etc. or, less than or equal to 800 micrometers, less than or equal to 700 micrometers, less than or equal to 600 micrometers, less than or equal to 500 micrometers, less than or equal to 450 micrometers, less than or equal to 350 micrometers, etc. or any range within the aforementioned values. The pen tip area 3116 may also be defined by a height 3142 from the bottom surface 3112 of about, e.g., greater than or equal to 50 micrometers, greater than or equal to 100 micrometers, greater than or equal to 150 micrometers, greater than or equal to 250 micrometers, greater than or equal to 350 micrometers, greater than or equal to 450 micrometers, etc. or, less than or equal to 800 micrometers, less than or equal to 700 micrometers, less than or equal to 600 micrometers, less than or equal to 500 micrometers, less than or equal to 400 micrometers, less than or equal to 300 micrometers, etc. or any range within the aforementioned values. The height 3142 may be measured from a lowest point of the bottom surface 3112. In such embodiments, the entire volume of the well 3115 is the cell culturing volume 3140.

The diametric dimension of the top aperture 3118 may be greater or equal to the diametric dimension 3144 of the pen tip area 3116. The diametric dimension 3144 of the pen tip area 3116 may be greater than or equal to the diametric dimension of the bottom surface 3112. It may also be described that the diametric dimension of the bottom surface 3112 is less than or equal to the diametric dimension 3144 of the pen tip area 3116 or the diametric dimension 3144 of the pen tip area 3116 may be less or equal to the diametric dimension of the top aperture 3118. In some embodiments, the top aperture 3118 may be the pen tip area 3116.

The sidewall surface 3120 of each of the plurality of wells 3120 extends from the top aperture 3118 to the bottom surface 3112. The sidewall surface 3120 may include an upper sidewall surface 3124 and a lower sidewall surface 3122. The upper sidewall surface 3124 may be defined between the top aperture 3118 and the pen tip area 3116. The lower sidewall surface 3122 may be defined between the pen tip area 3116 and the bottom surface 3112. In some embodiments, the sidewall surface 3120 of each of the plurality of wells 3115 may define a cell non-adherent surface. The cell non-adherent surface facilitates growing the cells into spheroids 3130 in the cell culturing volume 3140 as described previously. Cell non-adherent upper sidewall surfaces 3124 can facilitate settling of seeded cells into the cell culture volume 3140. Regardless of whether the upper sidewall surfaces 3124 are cell non-adherent, the upper sidewall surfaces 3124, in some embodiments, are configured to cause cells seeded in the wells to settle into the pen tip area 3116 to form the cell culturing volume 3140 as a result of gravity.

In some embodiments, the upper sidewall surface 3124 and the lower sidewall surface 3122 may be defined by a shape that is, e.g., parabolic, conical, stepped, various angles, curved, etc. The upper and lower sidewall surfaces 3124, 3122 may have the same or different shapes. In some embodiments, the sidewall surface 3120 may have an inflection point 121 at a location where the upper and lower sidewall surfaces 3124, 3122 meet (e.g., as shown in FIG. 29). In other embodiments, the sidewall surface 3120 may have a continuous slope at the inflection point 3121 where the upper and lower sidewall 3124, 3122 surfaces meet.

In some embodiments, a portion of sidewall 3120 adjoining the bottom surface 112 may be normal to the bottom surface 3112 or at an angle to the bottom surface 3112. The portion of the sidewall 3120 adjoining the bottom surface 3112 may be described as the lower sidewall surface 3122. The angle at which the portion of the sidewall 3120 intersects the bottom surface 3112 may be defined relative to the bottom surface 3112 as, e.g., greater than or equal to 90 degrees, greater than or equal to 92 degrees, greater than or equal to 95 degrees, greater than or equal to 100 degrees, etc. or, less than or equal to 110 degrees, less than or equal to 105 degrees, less than or equal to 102 degrees, less than or equal to 97 degrees, etc. or any range within the aforementioned values. In some embodiments, the diametric dimension across the sidewall surface 3120 may be described as increasing from the bottom surface 3112 towards the top aperture 3118. The sidewall geometry may be any geometry that sufficiently allows the cells to settle into each of the plurality of wells 3115.

With regards to a bottom surface 3112 that does not have a flat surface, the angle of the sidewall 3120 is considered to be relative to an imaginary plane that is tangential to the nadir of the bottom surface 3112. In other embodiments, the imaginary plane may also be defined as being coplanar with the top aperture 3118 regardless of whether the imaginary plane is tangential to the nadir.

A combination of the bottom surface 3112, the pen tip area 3116 and a portion of the sidewall surface 3120 may define a cell culture volume 3140. The portion of the sidewall surface 3120 that defines the cell culture volume 3140 may also be described as the lower sidewall surface 3122. The cells are not restricted to being cultured only in the cell culture volume 3140. However, cells deposited within each of the plurality of wells 3115 may aggregate in the cell culture volume 3140 to form and grow a spheroid 3130. Also, the dimensions of the spheroid 3130 may be a result of the shape and size of the cell culture volume 3140. For example, the cell culture volume 3140 of each of the plurality of wells 3115 is configured to cause spheroids 3130 to grow to a diameter of about, e.g., less than or equal to 500 micrometers, less than or equal to 400 micrometers, less than or equal to 300 micrometers, less than or equal to 250 micrometers, less than or equal to 150 micrometers, etc. or any range within the aforementioned values. In some embodiments, the cell culture volume 3140 of each of the plurality of wells 3115 forms a spheroid 3130 defined by a diameter that differs from an average diameter of all the spheroids 3130 grown in the plurality of wells 3115 by about, e.g., less than or equal to 20%, less than or equal to 15%, less than or equal to 10%, less than or equal to 5%, less than or equal to 2%, etc. or any range within the aforementioned values.

A combination of the top aperture 3118, the pen tip area 3116 and a portion of the sidewall surface 3120 may define a second volume 3145. The portion of the sidewall surface 3120 that defines the second volume 3145 may also be described as the upper sidewall surface 3124. The second volume 3145 may be greater than the cell culture volume 3140. For example, the second volume 3145 may be about, greater than or equal to 100%, greater than or equal to 200%, greater than or equal to 500%, greater than or equal to 1,000%, greater than or equal to 10,000%, greater than or equal to 100,000%, greater than or equal to 200,000%, etc. of the cell culture volume 3140 or any range within the aforementioned values. By way of example, a 96-well plate may have a cell culture volume defined by a volume of 0.1 microliters and a second volume defined by a volume of 200 microliters, resulting in a second volume that is 2,000 times greater in volume than the cell culture volume.

One embodiment of the cell culture apparatus 3100 is illustrated in FIG. 27. As shown in FIG. 27, the sidewall surface 3120 of each of the plurality of wells 3115 tapers from the top aperture 3118 to the bottom surface 3112. Specifically, the sidewall surface 3120 is extending from the top aperture 3118 in a direction that is almost normal to the top aperture 3118 but at a slight angle that decreases a diametric dimension across the sidewall surface 3120 as the sidewall surface 3120 extends towards the bottom surface 3112. At a point 3123 along the sidewall surface 3120 that is between the top aperture 3118 and the pen tip area 3116, the angle of the sidewall surface 3120 changes to further decrease the diametric dimension across the sidewall surface 3120 as the sidewall surface 3120 extends towards the bottom surface 3112. At the pen tip area 3116, the angle of the sidewall surface 3120 changes yet again and extends towards the bottom surface 3112. This last portion of the sidewall surface 3120 is sometimes described as the lower sidewall surface 3122. As shown in FIG. 27, in embodiments, the lower sidewall surface 3122 may be slightly angled from being perpendicular to the bottom surface 3112 and the diametric dimension across the sidewall surface 3120 decreases as the sidewall surface 3120 extends towards the bottom surface 3112. A spheroid 3130 is depicted as positioned within the lower sidewall surface 3122 and against the bottom surface 3112 (i.e. in the pen tip area 3116). The lower sidewall surface 3122 may restrict or limit the size to which the spheroid 3130 can grow.

One embodiment of the cell culture apparatus 3100 is illustrated in FIG. 28. As shown in FIG. 28, the sidewall surface 3120 of each of the plurality of wells 3115 tapers from the top aperture 3118 to the bottom surface 3112. Specifically, the sidewall surface 3120 initially extends from the top aperture 3118 at an angle normal to the top aperture 3118 and then extends along a parabolic path towards the pen tip area 3116. At the pen tip area 3116, the angle of the sidewall surface 3120 changes and extends towards the bottom surface 3112. This last portion of the sidewall surface 3120 is sometimes described as the lower sidewall surface 3122. As shown in FIG. 29, the lower sidewall surface 3122 is slightly angled from being perpendicular to the bottom surface 3112 and the diametric dimension across the sidewall surface 3120 decreases as the sidewall surface 3120 extends towards the bottom surface 3112. A spheroid 3130 is depicted as positioned within the lower sidewall surface 3122 and against the bottom surface 3112, in the pen tip area 3116 The lower sidewall surface 3122 may restrict or limit the size to which the spheroid 3130 can grow. The pen tip area is a spheroid inducing geometry.

Figure 30:
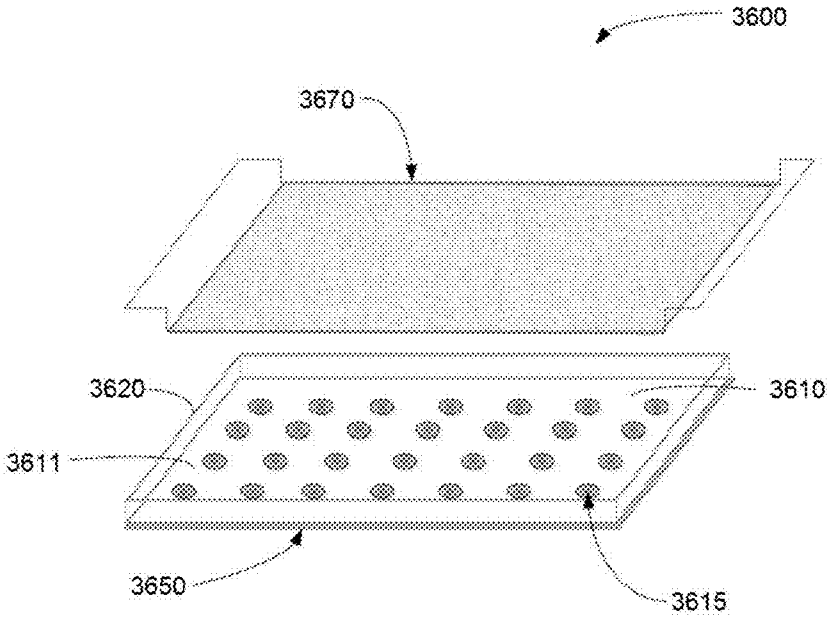
FIG. 30 is a schematic perspective view of an embodiment of a cell culture apparatus having a plate and wells.

Turning now to FIG. 30, in some embodiments, the cell culture apparatus 3650 may include a bottom plate 3610 and one or more sidewalls 3620, as shown in FIG. 30. The bottom plate 3610 may define a major surface 3611 and the one or more sidewalls 3620 may extend from the bottom plate 3610. The bottom plate 3610 may be formed, in whole or in part, from a substrate having an array of microwells 3615. FIG. 30 illustrates that the bottom plate may have an array of arrays of microwells 3615. That is, each of the areas identified as an array of microwells 3615 shown in FIG. 30 may contain an array of much smaller microwells. In embodiments, cell culture apparatus 3650 may also include a plurality of wells 3615 formed in the major surface 3611 of the bottom plate 3610. Each well of the plurality of arrays of microwells 3615 may define microwells or cell culture volumes, as described previously, that promote or induce the growth of spheroids. The major surface 3611 of the bottom plate 3610 and the one or more sidewalls 3620 define a reservoir volume. Reservoir plates described herein permit the addition of culture medium in excess of what would be typically used to fill individual shallow wells of a microwell plate and allows cells cultured in different wells to be in fluid communication.

In some embodiments, the one or more sidewalls 3620 may extend farther away (e.g., a sidewall height) from the bottom plate 3610 than some currently available cell culture apparatuses, allowing the reservoir to hold a larger than normal volume of medium. The larger capacity opportunity for the reservoir may allow an excess of culture medium to be added to the reservoir so that the spheroids may not need to rely only on the amount of medium in each individual well. In other words, the spheroids may not need to be fed with cell culture medium as frequently as spheroids growing in standard microplate wells. As shown in FIG. 30, nutrients and metabolites may be exchanged throughout the cell culture medium because the cell culture medium in the reservoir is in communication with all of the wells in the reservoir.

In some embodiments, a cell culture assembly 3600 may include a cell culture apparatus 3650 and a fluid permeable mesh 3670. The fluid permeable mesh 3670 can be placed on top of the wells 3615 after cells have been seeded into the wells. The cell culture medium that is in common communication among the plurality of wells 3615 can be isolated and replaced during a manual batch feeding process without disturbing the cells in the wells. Because the cells, in some embodiments, can be non-adherent to the surface of the wells, exchange of cell culture media without disturbing or losing the spheroid can be difficult. However, use of mesh 3670 as discussed above can mitigate such difficulties. For example, the combination of a cell culture apparatus and fluid permeable mesh may be as described in U.S. provisional patent application No. 62/072,103, filed on 29 Oct. 2014, and entitled "RESERVOIR SPHEROID PLATE," which provisional patent application is hereby incorporated herein by reference in its entirety to the extent that it does not conflict with the present disclosure.

It will be understood that the wells 3615 of a cell culture apparatus 3650 described herein can be of any size, shape or configuration. In some embodiments, the wells are formed from hexagonal close-packed well structures as depicted in FIG. 17. A reservoir plate apparatus having a structured surface with closely packed small volume wells may be particularly advantageous because the small volume of the wells would require frequent exchange of cell culture medium without the added reservoir volume.

Reservoir plates described herein permit, for example, the addition of culture medium in excess of what would be typically used to fill individual shallow wells of a microwell plate and allows cells cultured in different wells to be in fluid communication.

Figure 31:
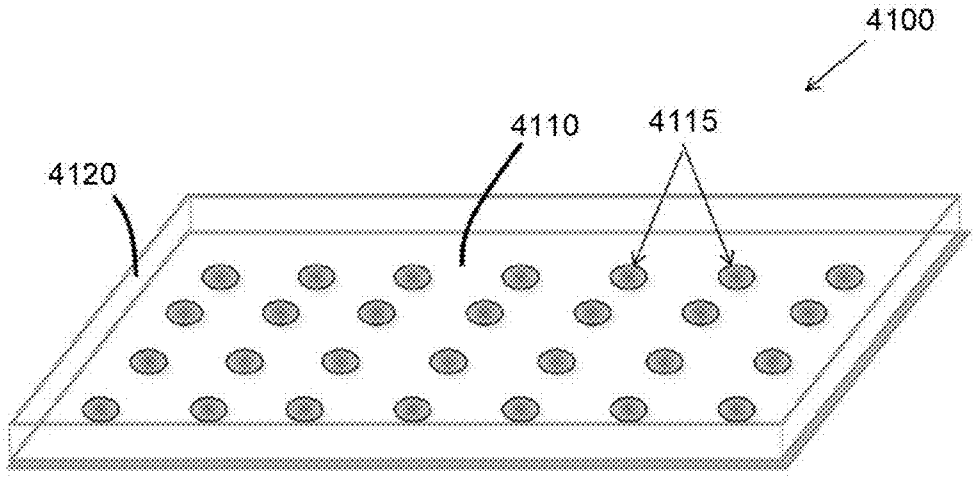
FIG. 31 is a schematic perspective view of an embodiment of a cell culture apparatus having a plate and wells.

As shown in FIG. 31, the cell culture apparatus 4100 may include a bottom plate 4110 and one or more sidewalls 4120. The bottom plate may define a major surface and the one or more sidewalls 4120 may extend from the bottom plate. The combination of the bottom plate and the one or more sidewalls may define a reservoir. The cell culture apparatus may also include, in whole or in part, substrates having an array of microwells 4115 formed in the major surface of the bottom plate. Each well of the plurality of wells in the microwell array may define an upper aperture and a nadir. The upper aperture may be co-planar with the major surface and the nadir may be positioned below the major surface, i.e., the nadir may be positioned a direction opposite that which the one or more sidewalls extend from the bottom plate. A top plate (not shown) may be disposed over the reservoir as desired while incubating cells.

In some embodiments, the one or more sidewalls may extend farther away from the bottom plate than typical, and therefore, allowing the reservoir to hold a larger than normal volume of medium. The larger capacity opportunity for the reservoir may allow an excess of culture medium to be added to the reservoir so that the spheroids may not need to rely only on the amount of medium in each individual well. In other words, the spheroids may not need to be fed with cell culture medium as frequently as spheroids growing in standard microplate wells. As shown in FIG. 31, nutrients and metabolites may be exchanged throughout the cell culture medium because the cell culture medium in the reservoir is in communication with all of the wells in the reservoir.

In some embodiments, a cell culture assembly 4200 is described herein. The assembly can include an apparatus 4100 (e.g., as depicted and discussed with regard to FIG. 31) and a fluid permeable mesh 4570. The fluid permeable mesh 4570 can be placed on top of the wells 4115 after cells have been seeded into the wells. The cell culture medium in common communication can be isolated and replaced during a manual batch feeding process without disturbing the cells in the wells.

Figure 32:
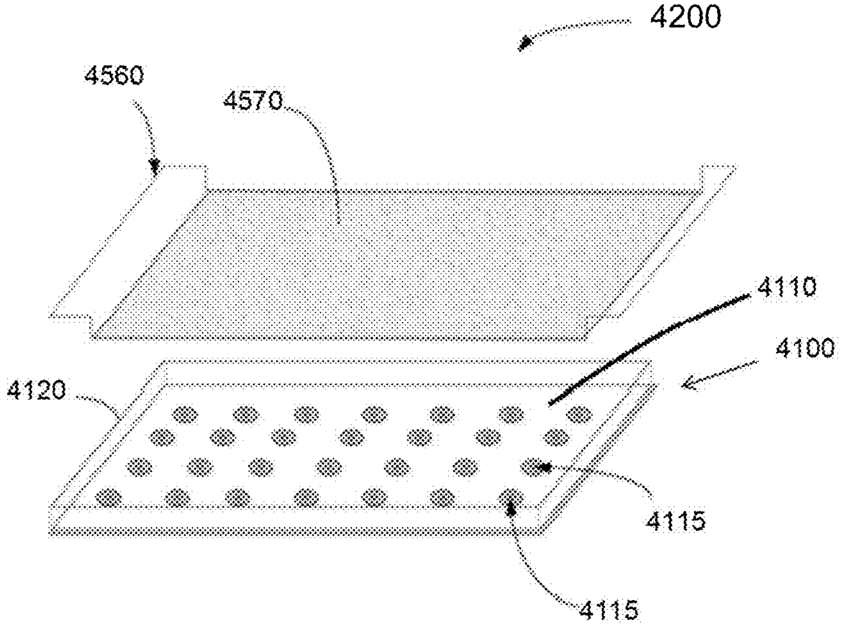
FIG. 32 is a schematic perspective view of an embodiment of a cell culture apparatus and an insert including a mesh.

In some embodiments (e.g., as depicted in FIG. 32), a frame 4560 can be coupled to the mesh 4570, as shown. The frame 4560 may be configured to maintain the mesh 4570 in place over the wells first well 4515. In some embodiments, the mesh 4570 is configured to be disposed over an upper edge of sidewall 4120 of apparatus 4100. The frame 4560 can engage one or more sidewall 4120 via interference fit, snap fit, or any other suitable mechanism to retain the mesh on the major surface of the plate 4110. In some embodiments, a user can manually retain the frame 4560 in place such that the mesh is retain on the major surface of the plate 4110 over the wells 4115.

Fluid permeable mesh 4570 may be formed of any suitable material. In some embodiments, fluid permeable mesh defines pores. The pores can be of any suitable size. In some embodiments the pores define an average pore size in a range from 10 micrometers to 100 micrometers. In some embodiments, the pores define an average pore size of less than or equal to 40 micrometers. Preferably, the pores of the mesh are of a sufficiently small size to prevent passage of a spheroid through the mesh.

In some embodiments, mesh can be as described in, for example, commonly-assigned U.S. provisional patent application Ser. No. 62/072,094, which provisional patent application is hereby incorporated herein by reference in its entirety to the extent that it does not conflict with the present disclosure.

In some embodiment, instead of manually replacing cell culture medium manually, a reservoir plate as described herein can be fabricated as a perfusion device in which cell culture medium can flow across the reservoir above the major surface of the wells.

Figure 33:
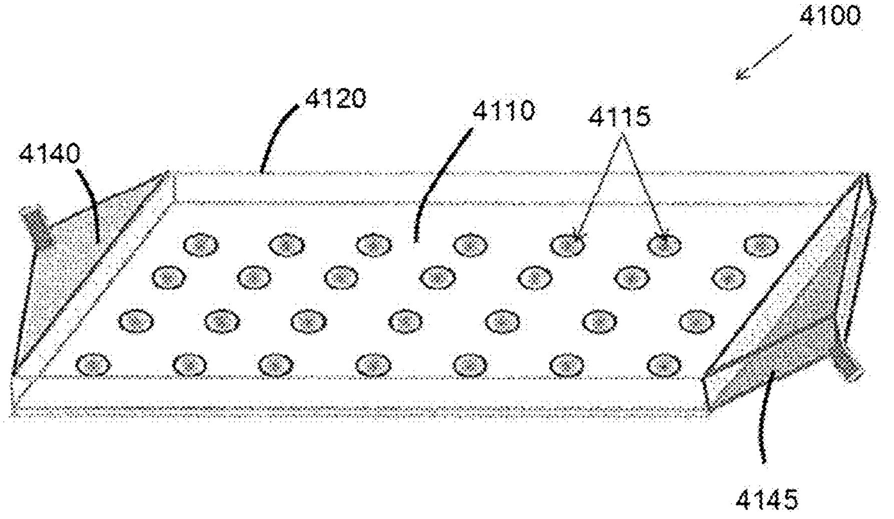
FIG. 33 is schematic a perspective view of an embodiment of an apparatus having an inlet and an outlet.

For example and with reference to FIG. 33, a cell culture apparatus as described in and discussed with regard to FIG. 31 4100 can be adapted such that one or more sidewall forms an inlet 4140 and one or more sidewalls forms an outlet 4145. Cell culture fluid can be perfused across the reservoir from the inlet to the outlet. The form factor of the apparatus depicted in FIG. 33 can be an open top form factor or can be closed top. If the form factor is open top, an insert including a frame and mesh as discussed with regard to FIG. 2A and FIG. 2B can be used to retain cells within wells 4115 if high perfusion rates that might otherwise dislodge cells, such as spheroids, from the wells.

A cell culture apparatus as described herein can be manufactured in any suitable manner. In various embodiments, a method of manufacturing a cell apparatus includes molding a polymeric material, or any other suitable material as described herein, to form the cell culture apparatus. The polymeric material may define a plurality of wells of the cell culture apparatus. Each of the plurality of wells may define a top aperture, a bottom surface, and a sidewall surface extending from the top aperture to the bottom surface. The sidewall surface may also define a pen tip area between the top aperture and the bottom surface. The polymeric material may be poured into a mold having pins that cause polymeric material molded around the pins to have the characteristics of the plurality of wells as described herein.

In some embodiments, a polymeric material is overmolded onto a substrate to form the cell culture apparatus. The substrate defines the bottom surface and the combination of the polymeric material and the substrate defines the plurality of wells. The polymeric material may be poured into a mold having pins that cause polymeric material molded around the pins to have the characteristics of the plurality of wells as described herein.

In some embodiments, regardless of how a cell culture apparatus described herein is manufactured, sidewall surfaces of each of a plurality of wells may be coated with a cell non-adherent material as further described herein.

In some embodiments, wells comprise various features that are part of, or appended to, the sidewalls. Such substrate features can be directly injection molded, or they can be embossed onto formed substrates. Materials of features can be any polymer, polymer blend, co-polymer, glass, metal, or any other material described herein or understood in the field.

The devices, wells, sidewalls, well-bottom, and other features described herein are formed of any suitable material. Preferably, materials intended to contact cells or culture media are compatible with the cells and the media. Typically, cell culture components are formed from polymeric material. Examples of suitable polymeric materials include polystyrene, polymethylmethacrylate, polyvinyl chloride, polycarbonate, polysulfone, polystyrene copolymers, fluoropolymers, polyesters, polyamides, polystyrene butadiene copolymers, fully hydrogenated styrenic polymers, polycarbonate PDMS copolymers, and polyolefins such as polyethylene, polypropylene, polymethyl pentene, polypropylene copolymers and cyclic olefin copolymers, and the like.

In embodiments, the inner surface of the wells is non-adherent to cells. The wells may be formed from non-adherent material or may be coated with non-adherent material to form a non-adherent surface. Example non-adherent materials include perfluorinated polymers, olefins, or like polymers or mixtures thereof. Other examples include agarose, non-ionic hydrogels such as polyacrylamides, polyethers such as polyethylene oxide, and polyols such as polyvinyl alcohol, or like materials or mixtures thereof. In some embodiments, the combination of, for example, two or more of non-adherent wells, well geometry, and/or gravity induces cells cultured in the wells to self-assembly into spheroids. Some spheroids maintain differentiated cell function indicative of a more in vivo like response relative to cells grown in a monolayer. In embodiments where the wells are non-adherent to cells, the cells may be harvested by inverting the apparatus to allow gravity to displace the cells from the wells.

In some embodiments, surface modification of materials is used to achieve desired properties. Such modifications include modification of surface chemistry and mechanical properties may utilize using biological coatings (e.g., Matrigel™, collagen, laminin, etc.) and synthetic coatings (e.g., Synthemax®, silicone hydrogels, etc.). Other surface modifications to materials (e.g., within wells or microstrucutres) is within the scope herein.

A substrate having a structured surface as described herein can be assembled into a cell culture chamber or tray in any suitable manner. For example, the structured surface and one or more other components of the cell culture chamber or tray may be molded as a single part. In some embodiments, the structured surface or a portion thereof overmolded to form the bottom and one or more components, the structured surface is welded (e.g., thermal, laser, long IR or ultrasonic welding, or the like), adhered, solvent-bonded or the like to one or more other components of the cell culture apparatus.

In various embodiments, a cell culture system can include more than one cell culture apparatus component described herein above. By way of example, the apparatus components can be stacked to form a cell culture system. Examples of stacked cell culture systems that can incorporate a cell culture apparatus component as described herein include those described in for example, (i) U.S. provisional patent application No. 62/072,015, filed on 29 Oct. 2014, entitled “MULTILAYER CULTURE VESSEL,”; (ii) U.S. provisional patent application No. 62/072,039, entitled “PERFUSION BIOREACTOR PLATFORM”, filed on 29 Oct. 2014, which provisional patent applications are each hereby incorporated herein by reference in their respective entireties to the extent that they do not conflict with the present disclosure.

The cell culture apparatuses described herein can be used to culture cells within wells of the apparatus in any suitable manner. For example, a method for culturing cells involves introducing cells and a cell culture medium into one or more of the plurality of wells of a cell culture apparatus as described herein. The cell culture medium may be contained in only the cell culture volume or the entirety of each of the plurality of wells including the cell culture volume and the second volume. The method also involves culturing cells in the medium in the one or more plurality of wells. Culturing the cells in the one or more of the plurality of wells may include forming a spheroid within the one or more wells. The spheroid cultured within the one or more wells may be defined by a diameter of about, e.g., less than or equal to 500 micrometers, less than or equal to 400 micrometers, less than or equal to 300 micrometers, less than or equal to 250 micrometers, less than or equal to 150 micrometers, etc. or any range within the aforementioned values The diameter of one spheroid may differ from an average diameter of all the spheroids grown in the plurality of wells by about, e.g., less than or equal to 20%, less than or equal to 15%, less than or equal to 10%, less than or equal to 5%, less than or equal to 2%, etc. or any range within the aforementioned values In some embodiments, the well-bottom comprises a concave arcuate surface or “cup” geometry, for example, a hemi-spherical surface, a conical surface having a rounded bottom, and like surface geometries, or a combination thereof. The well (e.g., microwell) and well-bottom ultimately terminates, ends, or bottoms-out in a spheroid “friendly” rounded or curved surface, such as a dimple, concave frusto-conicial relief surfaces, or combinations thereof.

In certain embodiments, portions of the sidewalls and/or well-bottom are of varying degrees of opaqueness/transparency to wavelengths within the visible and/or UV spectrum. For example, opaque sidewall may be combined with a transparent microwell-bottom. The transition from opaque to transparent portions may be gradual or immediate.

In some embodiments, the wells (e.g., microwells) comprise a low-adhesion, no-adhesion, or high adhesion coating on a portion of the well, such as on the at least one concave arcuate surface.

In some embodiments, the device further comprises, for example, a well annex, well extension area, or an auxiliary side chamber, for receiving a pipette tip for aspiration. In some embodiments, the well annex or well extension (e.g., a side pocket) is, for example, an integral surface adjacent to and in fluid communication with the well (e.g., microwell). In some embodiments, the well annex has a bottom spaced away from a gas-permeable, transparent bottom of the well. The well annex and the second bottom of the chamber well are, for example spaced away from the gas-permeable, transparent bottom such as at a higher elevation or relative altitude. In some embodiments, the second bottom of the well annex deflects fluid dispensed from a pipette away from the transparent bottom to avoid disrupting or disturbing the spheroid.

In certain embodiments, the device further comprises a porous membrane, such as a liner or membrane insert, situated within a portion of the well, situated within a portion of a well annex, or both the well and the well annex portion. The porous membrane can provide isolation or separation of a second cellular material, such as a different cell type or different cell state, situated in an upper portion of the well, in an upper portion of the well formed by the porous membrane, or both wells, from first cellular material in a lower portion of one or both wells near bottom.

Devices and well geometries are manufactured by any suitable techniques known in the field. In some embodiments, hot embossing, thermal deformation, and/or injection molding methods are used for the production of micropatterned surfaces in cell-culture-compatible plastics. FIG. 12 depicts schematics of a hot embossing/thermoforming fabrication process that finds use herein. In some embodiments, polystyrene film (or another suitable polymer film) of specific thickness is placed on heat a resistive silicone support.

Then the mold is placed on the film with microposts facing down. The whole assembly is pressed under 5N load between plates which are preheated to 130° C. for 10 min. After 10 min. plates are cooled below 100° C. and micropatterned embossed/thermoformed film is removed from the assembly and incorporated into regular cell culture vessels as a 3D aggregate promoting surface. Other temperatures, times, pressures, and materials may be within the scope herein.

To prevent cell attachment, in some embodiments, micropatterned surfaces are treated with polymers that inhibit cell attachment such as poly-HEMA, pluronic, or proprietary ULA treatment. Depending on the initial polymer film thickness and process parameters, surfaces with microwells that have different bottom thickness are generated. In some embodiments, polymer thickness of the microwell bottom has a direct impact on oxygen permeability. Thinner microwell bottoms allow better oxygen supply to cells located inside the microwells. The above fabrication method delivers a surface with highly oxygen permeable microwells.

In some embodiments, devices and systems herein comprise microfluidic elements for the movement of fluids (e.g., media) and cells (e.g., spheroids) into and out of various compartments, wells, etc. in such devices. Microfluidic elements may include channels, reservoirs, valves, pumps, etc.

In vitro 3D tumor cell cultures reflect more accurately complex in vivo microenvironment than simple two-dimensional cell monolayers. In some embodiments, a cell culture format with microwell patterned surface, as described herein, provides for generating 3D cultures (e.g., tumor spheroids) in large quantities, of uniform size that are compatible with routine high-throughput drug development and preclinical studies.

In some embodiments, culture vessels described herein find use in the formation of embryoid bodies (EBs) from induced pluripotent stem (iPS) cells and embryonic stem cells (ESCs), allowing for uniform and easy aggregate formation on a large scale. In some embodiments, media changes are performed such that EBs are grown continuously for weeks. In some embodiments, the size of each aggregate is controlled as size is dependent on the number of cells seeded and time of culture. In some embodiments, aggregates are transferred to a traditional well plate allowing for a greater volume of media or analysis of spheroids. In some embodiments, large numbers of formed EB's provide statistically important data from high throughput analysis of transfected targets or small molecules in a single plate. Ability to support formation of large number of 3D cell aggregates in one culture vessel makes these vessels, for example modified petri dishes, applicable for the selection of EB-forming clones for cell reprogramming. In some embodiments, vessels described herein also support formation of 3D cell aggregates in a variety of cell types related to toxicology, such as hepatocytes and embryonic stem cells. In some embodiments, microwell surface vessels are used for 3D aggregates cell culture with the purpose of, for example, protein production in the bioprocessing field. In some embodiments, a cell culture format with microwell patterned surface, as described herein, provides a means to enable stem cell niche co-culture, in particular, clonogenic culture, single stem cells and niche co-culture. Combining with staining protocol established for stem cell surface markers or stem cell differentiation markers as well as imaging, computational identification of single stem cells and niche co-culture can be performed.

Micropatterned vessels are also used for cell banking purposes to preserve cells in 3D format. In some embodiments, once the spheroids are grown to the specified size (typically at transitional state before stable state), they are dislodged from the microwells, and the collected spheroids are cryopreserved and banked for use at a later date. Transtional spheroids mean that the spheroids can continuously grow in size, while the stable spheroids means that the spheroids stop growing in size once reaching its intrinsic size limit. Various cryopreservation methods are within the scope herein, including, but not limited to dimethyl sulfoxide (DMSO), fetal bovine serum (FBS), etc.

EXAMPLES

Example 1: Substrate Manufacture

Substrates according to embodiments were manufactured using an embossing method, as illustrated in FIG. 12. FIG. 12 shows a hot embossing/thermoforming process of microwell formation in polymer film. Hot plates 1 are provided. Hot plates were preheated to 130° C. An embossing mold 2 was provided, reflecting the desired well profile. A layer of polymer film 3 was provided, and a silicone mat 4 was provided behind the polymer film. The hot plates were heated, and were pressed against the polymer film, backed by the silicone layer. When the hot plates were removed, a polymer film having an array of microwells having the desired well profile embossed therein was provided.

Example 2: Cell Culture

Experiments conducted during development of embodiments described herein demonstrate, for example, that 3D cell culture aggregates of uniform diameter are formed and cultured in an array of individual, spatially separated microwells each having hemispherical round bottoms and rounded tops, with a diameter (D) that is about 1 to 3 times of the desired diameter of 3D cellular aggregate. The microwell height (H) is equal to about 0.7 to 1.3 times of the diameter of round bottom part, and the diameter of upper opening of the microwell ($D_{top}$) is equal to about 1.5 to 2.5 times of the round bottom diameter.

Figure 13:
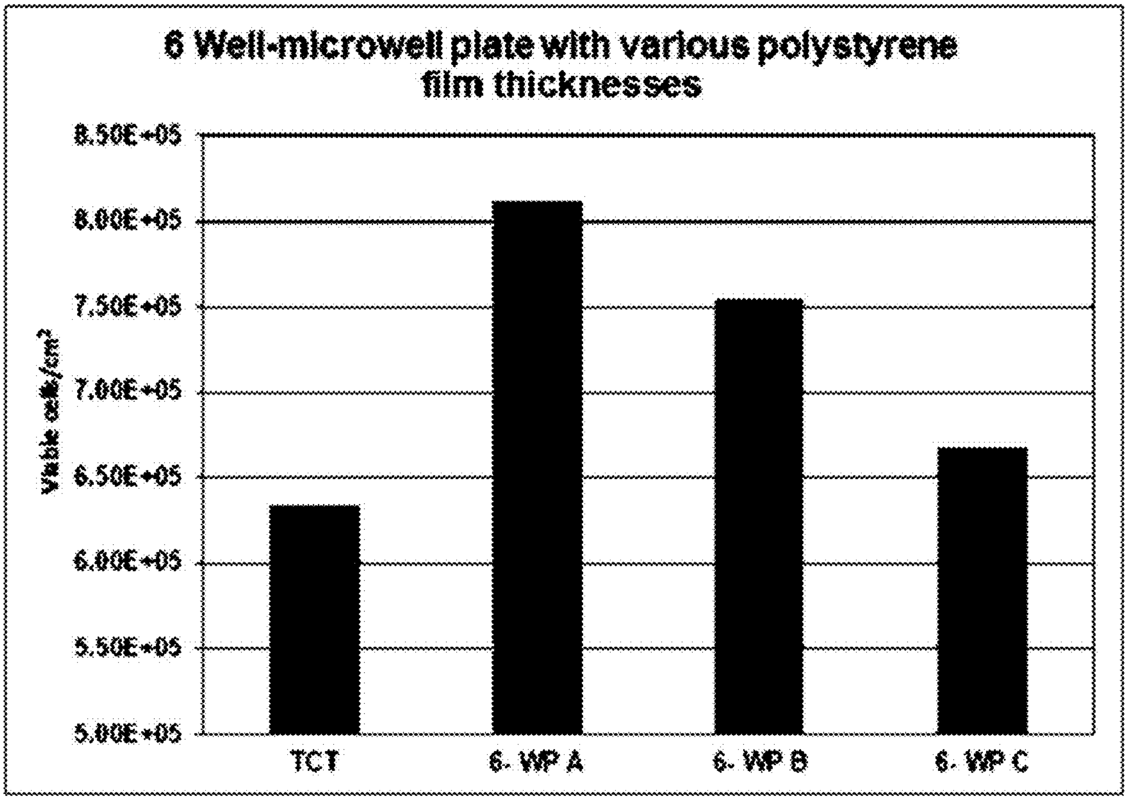
FIG. 13 shows a graph demonstrating viable cell counts measured after growing cells in 6 well plates having substrates having an array of microwells (as described in Example 1), in microwells with different bottom thickness.

Experiments were conducted in which a T25 cell culture flask prototype with a microwell patterned surface was fabricated and tested in cell culture applications to verify uniformity of spheroid formation and retention/harvesting benefits of proposed design. FIG. 8 contains an image of reverse replica of T25 prototype microwell cross-resections with round bottom geometry. Images of spheroids formed by HT29 cells in prototype T25 flask are shown in FIG. 10A. FIG. 10B depicts spheroids harvested from the flask, which can be compared to those grown using with commercially available NUNCLON SPHERA™ low binding surface flask, available from Nunc Nunc/Thermo Fisher, which are depicted in FIG. 11A and FIG. 11B, the superior performance of the wells described herein is evident in the uniformity of the spheroids produced in embodiments compared to the commercially available control, which has a low binding surface but no wells to define and control spheroid production. The round bottom geometry is a spheroid inducing geometry. Experiments were conducted during development of embodiments herein to demonstrate the impact of oxygen permeability of microwells on cell culture performance. 6 and 12 well plates were manufactured,, as described above in Example 1, having microwells of different thicknesses. FIG. 13 shows a graph demonstrating viable cell counts measured after growing cells in 6 well plates having substrates containing an array of microwells (as described in Example 1), in microwells with different bottom thicknesses. As shown in FIG. 13, A is 70 μm thickness, B is 120 μm thickness and C is 320 μm. Controls was TCT-treated 1 mm thick flat polystyrene. As can be seen from the results presented in FIG. 13, thinner material (which exhibits more gas permeability) supported more robust cell growth, in embodiments.

Figure 14A:
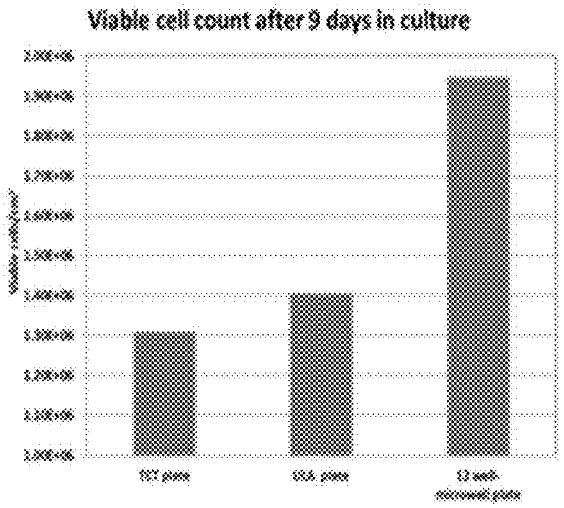
FIG. 14A and FIG. 14B show graphs comparing viable cell count (FIG. 14A) and cell productivity (FIG. 14B) for substrates having arrays of microwells versus flat surfaces.
Figure 14B:
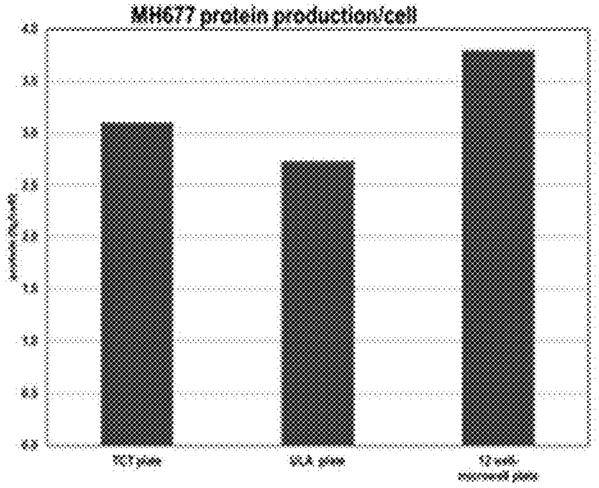

FIG. 13 shows a graph demonstrating viable cell counts measured after growing cells in 6 well plates having substrates containing an array of microwells (as described in Example 1), inmicrowells with different bottom thickness. FIG. 14A and FIG. 14B show graphs comparing viable cell count and cell productivity for substrates having arrays of microwells versus flat surfaces. FIG. 15 shows a graph depicting total protein titer excreted from MH677 cells cultured on substrates having arrays of microwells versus flat surface.

Culture of MH677 cells was performed for the duration of 7 or 9 days with media exchange every 2 days. Results presented in FIG. 13 demonstrate dependence of total viable cell counts on microwell bottom thickness. Cells cultured in oxygen permeable microwells (column A, 70 um thick bottom) yielded an 82% higher viable cell count in comparison to less oxygen permeable column C, 320 um thick bottom. Overall, culture on a microwell patterned surface yields higher a viable cell count (FIG. 14A) and higher productivity per cell (FIG. 14B) in comparison to regular flat non-adherent surfaces (FIG. 14A and FIG. 14B). This produces 85% higher protein yield (FIG. 15).

Figure 34A:
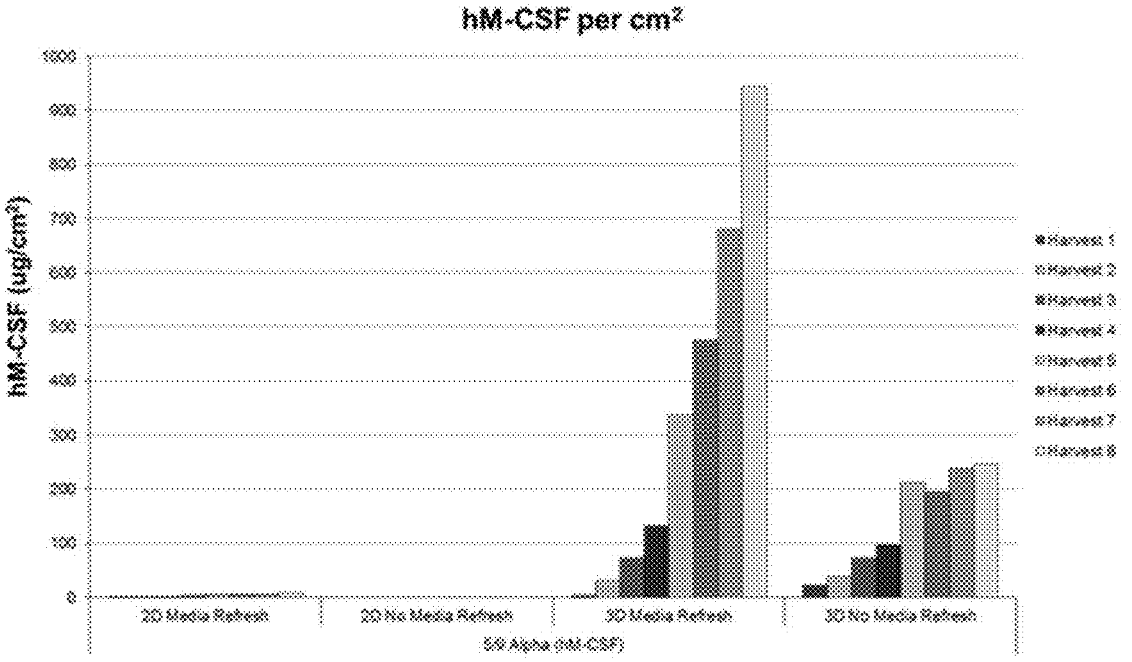
FIG. 34A and FIG. 34B show graphs depicting Protein production per cm2 in 96-well spheroid micro-well plates (FIG. 34A) in CHO 5/9 alpha cells, and (FIG. 34B) in BHK-21 pc.DNA3-1HC cells.
Figure 34B:
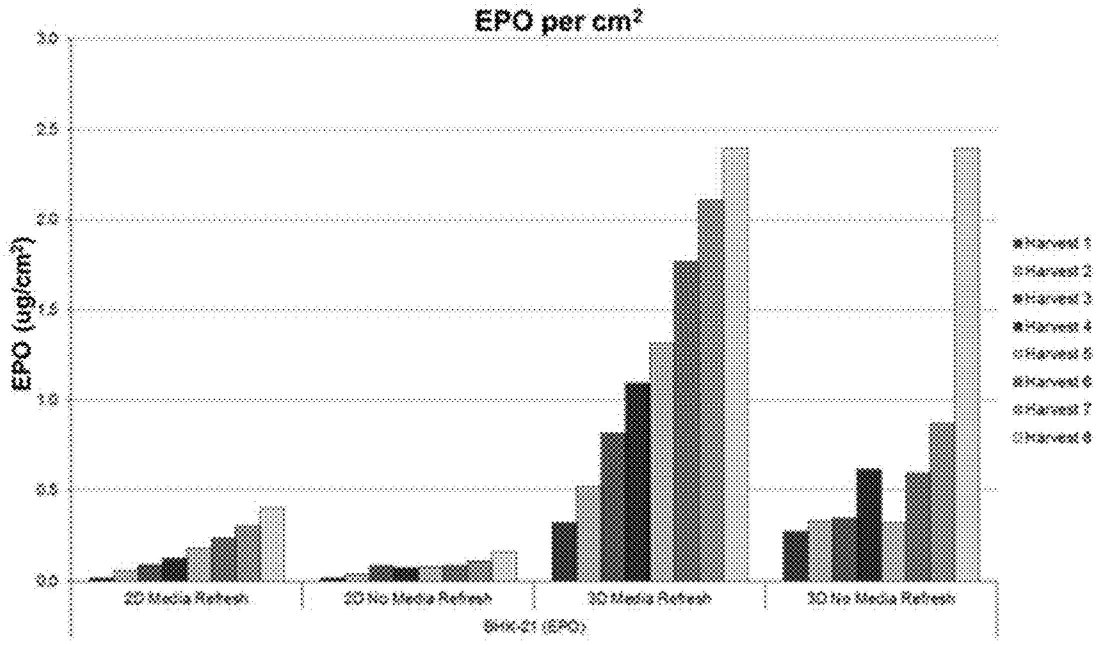

Experiments were conducted during development of embodiments herein to demonstrate the advantageous growth of cells in 3D culture vs. 2D culture using cell culture devices and wells described herein. In both CHO 5/9 alpha cells (FIG. 34A) and BHK-21 cells (FIG. 34B), vastly more protein (hm-CSF in FIG. 34A; EPO in FIG. 34B) was produced per $cm^2$ in 3D culture when compared to 2D.

All publications and patents mentioned in the present application and/or listed below are herein incorporated by reference. Various modification, recombination, and variation of the described features and embodiments will be apparent to those skilled in the art without departing from the scope and spirit of the invention. Although specific embodiments have been described, it should be understood that the invention as claimed should not be unduly limited to such specific embodiments. Indeed, various modifications of the described modes and embodiments that are obvious to those skilled in the relevant fields are intended to be within the scope of the following claims.

REFERENCES

1. H. Dolznig, A. Walzl, Organotypic spheroid cultures to study tumor-stroma interactions during cancer development. Drug discovery today, V 8., No 2-3, 2011, 113-118
2. J. Engelberg, G. Ropella, Essential operating principles for tumor spheroid grwth. BMC Systems Biology 2008, 2, 110
3. Y. Tung, A. Hsiao, S. Alen. High-throughput 3D spheroid culture and drug testing using 384 hanging drop array. Analyst, 2011, 136, 473-478
4. J. Friedrich, C. Seidel, R. Ebner. Spheroid-based drug screen: considerations and practical approach. Nature protocols, 2009, vol 4 no 3, 309-323
5. F. Hirschhaeuser, H. Menne, C. Dittfeld, Multicellular tumor spheroids: An underestimated tool is catching up again. Journal of Biotechnology, 2010, 148, 3-15
6. T. Bartosh, J. Ylostalo, A. Mohammadipoor. Aggregation of human mesenchymal stromal cells into 3D spheroids enhances their antiinflammatory properties. PNAS, 2010, 107, no 31, 13724-13729
7. J. Frith, M. Res, B. Thomson. Dynamic three-dimensional culture methods enhance mesenchymal stem cell properties and increase therapeutic potential. Tissue engineering, 2010, 16, no 4, 735-749
8. S. Sart, A. Tsai, Y. Li. Three-dimensional aggregates of mesenchymal stem cells: cellular mechanisms, biological properties and applications. Tissue engineering, 2013, Part B, 00, no 00, 1-16

What is claimed is:

1. A cell culture substrate, comprising:

an array of microwells, each microwell comprising:

an opening into the microwell defined by a top well edge;

a rounded well-bottom; and corrugated sidewalls positioned above the array of microwells, which extend along rows in the array and are configured such that a gap between any two corrugated sidewalls widens and narrows with each corrugation, wherein each microwell is fluidly connected to at least one other microwell by the gap between the corrugated sidewalls, wherein the corrugated sidewalls do not have any polygonal angles.

2. The cell culture substrate of claim 1 wherein at least the rounded well-bottom comprises a non-adherent surface.

3. The cell culture substrate of claim 1 wherein at least the rounded well-bottom comprises gas permeable material.

4. The cell culture substrate of claim 1 wherein the cell culture substrate comprises at least a portion of a cell culture container.

5. The cell culture substrate of claim 4 wherein the cell culture container is selected from the group consisting of a multiwell plate, a dish, a flask, a tube, a multi-layer flask, a soft-sided flask and a bag.

6. The cell culture substrate of claim 1, wherein microwells are configured to allow fluid communication between at least one of said microwells and a single liquid reservoir.

7. A method of culturing spheroids comprising: charging the cell culture container of claim 1 with culture media and spheroid forming cells.

8. The cell culture substrate of claim 1, wherein the microwell sidewalls are corrugated from the opening of the microwell to the bottom of the microwell.

9. The cell culture substrate of claim 1, wherein the microwell sidewalls are corrugated with a planar periodicity having regions where the sidewalls are far apart and then come closer together.

10. The cell culture substrate of claim 9, wherein the planar periodicity has regions where the sidewalls are far apart and then come closer together without contact.

11. The cell culture substrate of claim 9, wherein the planar periodicity has regions where the sidewalls are far apart and then come closer together with contact.

12. The cell culture substrate of claim 1, wherein each of the corrugated sidewalls includes opposing terminal ends and a length extending between the terminal ends, and wherein each of the corrugated sidewalls has a uniform cross-sectional profile along an entirety of the length.

13. The cell culture substrate of claim 1, wherein the microwells are treated with an ultra-low binding material to make the microwells non-adherent to cells.

14. A cell culture device, comprising:

a plurality of microwells disposed therein, each microwell comprising:

an upper portion, and a lower portion, wherein the lower portion is a rounded well bottom;

wherein the plurality of microwells is arranged in rows;

wherein each row is defined by two corrugated sidewalls that extend along each row and above each microwell's lower portion, and are aligned such that a continuous gap exists along each row that is between the sidewalls and widens and narrows with each corrugation; and wherein an upper portion of each microwell comprises part of each of the two corrugated sidewalls and is in fluid communication with adjacent microwells through the continuous gap;

wherein the two corrugated sidewalls do not have any polygonal angles.

15. The cell culture device of claim 14, wherein the microwell sidewalls are corrugated from the opening of the microwell to the bottom of the microwell.

16. The cell culture device of claim 14, wherein the corrugated sidewalls are enclosed by a frame.

17. The cell culture device of claim 14, wherein at least the rounded well-bottom comprises a non-adherent surface and gas permeable material.

18. The cell culture device of claim 14, wherein each of the two corrugated sidewalls includes opposing terminal ends and a length extending between the terminal ends, and wherein each of the two corrugated sidewalls has a uniform cross-sectional profile along an entirety of the length.

19. The cell culture device of claim 14, wherein the microwells are treated with an ultra-low binding material to make the microwells non-adherent to cells.

* * * * *